US010004803B2

(12) United States Patent
Mannick et al.

(10) Patent No.: US 10,004,803 B2
(45) Date of Patent: Jun. 26, 2018

(54) LOW, IMMUNE ENHANCING, DOSE MTOR INHIBITORS AND USES THEREOF

(71) Applicant: Novartis AG, Basel (CH)

(72) Inventors: Joan Mannick, Cambridge, MA (US); David Glass, Cambridge, MA (US); Leon Murphy, Cambridge, MA (US)

(73) Assignee: Novartis AG, Basel (CH)

( * ) Notice: Subject to any disclaimer, the term of this patent is extended or adjusted under 35 U.S.C. 154(b) by 0 days. days.

(21) Appl. No.: 15/292,088

(22) Filed: Oct. 12, 2016

(65) Prior Publication Data

US 2017/0281753 A1    Oct. 5, 2017

Related U.S. Application Data

(63) Continuation of application No. 14/540,867, filed on Nov. 13, 2014, now abandoned.

(60) Provisional application No. 62/052,629, filed on Sep. 19, 2014, provisional application No. 62/027,121, filed on Jul. 21, 2014, provisional application No. 61/903,636, filed on Nov. 13, 2013, provisional application No. 62/076,142, filed on Nov. 6, 2014.

(51) Int. Cl.
| | |
|---|---|
| *A61K 39/39* | (2006.01) |
| *A61K 39/12* | (2006.01) |
| *A61K 39/00* | (2006.01) |
| *A61K 31/519* | (2006.01) |
| *A61K 31/4745* | (2006.01) |
| *A61K 31/436* | (2006.01) |
| *A61K 39/09* | (2006.01) |
| *G01N 33/68* | (2006.01) |
| *A61K 39/145* | (2006.01) |
| *C12N 7/00* | (2006.01) |
| *A61K 45/06* | (2006.01) |

(52) U.S. Cl.
CPC ............ *A61K 39/39* (2013.01); *A61K 31/436* (2013.01); *A61K 31/4745* (2013.01); *A61K 31/519* (2013.01); *A61K 39/00* (2013.01); *A61K 39/09* (2013.01); *A61K 39/092* (2013.01); *A61K 39/12* (2013.01); *A61K 39/145* (2013.01); *A61K 45/06* (2013.01); *C12N 7/00* (2013.01); *G01N 33/6854* (2013.01); *A61K 2039/55511* (2013.01); *C12N 2760/16034* (2013.01)

(58) Field of Classification Search
CPC .......... A61K 2300/00; A61K 2039/505; A61K 39/00; A61K 39/39; A61K 2039/55511; A61K 39/12; A61K 39/145; A61K 38/00; C07K 16/2863; C12N 7/00; G01N 33/6854

See application file for complete search history.

(56) References Cited

U.S. PATENT DOCUMENTS

| | | |
|---|---|---|
| 2007/0265294 A1 | 11/2007 | Kleinman |
| 2009/0088373 A1 | 4/2009 | Gallo et al. |
| 2010/0129357 A1 | 5/2010 | Garcia-Martinez |
| 2010/0150829 A1 | 6/2010 | Garcia-Martinez |
| 2010/0196311 A1 | 8/2010 | Kim et al. |
| 2011/0129496 A1 | 6/2011 | Ahmed et al. |
| 2012/0148552 A1 | 6/2012 | Jensen |
| 2013/0309258 A1 | 11/2013 | June |
| 2015/0051266 A1 | 2/2015 | Kochenderfer |
| 2015/0079155 A1 | 3/2015 | Jensen |
| 2016/0046724 A1 | 2/2016 | Brogdon |
| 2016/0051651 A1 | 2/2016 | Brogdon |
| 2016/0068601 A1 | 3/2016 | Brogdon |
| 2016/0096892 A1 | 4/2016 | Brogdon |

FOREIGN PATENT DOCUMENTS

WO    WO 2014/0191128 A1    12/2014

OTHER PUBLICATIONS

McMichael AJ, Haynes BF. Influenza vaccines: mTOR inhibition surprisingly leads to protection. Nat Immunol. Dec. 2013;14(12):1205-7.*
Keating R, Hertz T, Wehenkel M, Harris TL, Edwards BA, McClaren JL, Brown SA, Surman S, Wilson ZS, Bradley P, Hurwitz J, Chi H, Doherty PC, Thomas PG, McGargill MA. Nat Immunol. Dec. 2013;14(12):1266-76. Epub Oct. 20, 2013.*
Zhou H, Luo Y, Huang S. Updates of mTOR inhibitors. Anticancer Agents Med Chem. Sep. 2010;10(7):571-81.*
Ballou LM, Lin RZ. Rapamycin and mTOR kinase inhibitors. J Chem Biol. Nov. 2008;1(1-4):27-36. doi: 10.1007/s12154-008-0003-5. Epub May 15, 2008.*
Huye LE, Nakazawa Y, Patel MP, Yvon E, Sun J, Savoldo B, Wilson MH, Dotti G, Rooney CM. Combining mTor inhibitors with rapamycin-resistant T cells: a two-pronged approach to tumor elimination. Mol Ther. Dec. 2011;19(12):2239-48. Epub Aug. 30, 2011.*
Clegg A, Young J, Iliffe S, Rikkert MO, Rockwood K. Frailty in elderly people. Lancet. Mar. 2, 2013;381(9868):752-62. doi: 10.1016/S0140-6736(12)62167-9. Epub Feb. 8, 2013. Review. Erratum in: Lancet. Oct. 19, 2013;382(9901):1328.*
Lievesley N, ed. Ageism and age discrimination in secondary health care in the United Kingdom: A review of the literature. Department of Health, Centre for Policy on Ageing. Dec. 2009.*
Withers DJ, Kennedy B. S6 Kinase and Ageing. Abstract, British Society for Research on Ageing, Annual Scientific Meeting. Sep. 2-4, 2013. University of East Anglia, Norwich.*
Youngblood et al., Immunol Rev., 235(1):234-243 (2010).
Murray et al., Antivir Chem Chemother., 22(5):205-215 (2012).
Chen et al., Sci Signal, 2(98):ra75 (2009).

* cited by examiner

*Primary Examiner* — Rachel B Gill
(74) *Attorney, Agent, or Firm* — Andrea L. C. Reid; Dechert LLP

(57) ABSTRACT

The present invention relates, in part, to compositions and methods for enhancement of an immune response by partial mTOR inhibition, for example, with low, immune enhancing, doses of an mTOR inhibitor, such as RAD001.

11 Claims, 8 Drawing Sheets

LOW, IMMUNE ENHANCING, DOSE MTOR INHIBITORS AND USES THEREOF

This application is a continuation of U.S. Ser. No. 14/540,867, filed Nov. 13, 2014 which claims priority to U.S. Ser. No. 61/903,636, filed Nov. 13, 2013, U.S. Ser. No. 62/027,121, filed Jul. 21, 2014, U.S. Ser. No. 62/052,629, filed Sep. 19, 2014, and U.S. Ser. No. 62/076,142, filed Nov. 6, 2014, the entire contents of each of these applications are incorporated herein by reference.

BACKGROUND

Functional and effective T-cell responses play an important role in effective immune responses, for example, against infectious diseases and cancer. However, under certain conditions, such as chronic infection or cancer, effector T cells can be suppressed by various immunosuppressive mechanisms, including programmed death ligand-1 (PD-L1)/programmed death-1 (PD-1) interaction, leading to T-cell exhaustion (Pen et al. Gene Therapy 21, 262-271, 2014). It is thought that PD-L1 is normally expressed by most cell types, while its receptor PD-1 is only present on certain immune cells, such as activated T cells and regulatory T (Treg) cells. It is also thought that PD-L1/PD-1 binding is important in the maintenance of peripheral T-cell tolerance, preventing auto immune responses. On the other hand, high levels of PD-1 expression generally correlate with loss of T cell function, leading to increased viral load in cases of viral infection (Pen et al. Gene Therapy 21, 262-271, 2014).

SUMMARY OF THE INVENTION

Methods and compositions disclosed herein are based, at least in part, on the discovery that partial mTOR inhibition, e.g., with low, immune enhancing, doses of an mTOR inhibitor, e.g., an allosteric mTOR inhibitor, such as RAD001, is effective to improve immune function in a subject. While not wishing to be bound by theory, it is believed that treatment with a low, immune enhancing, dose (e.g., a dose that is insufficient to completely suppress the immune system but sufficient to improve immune function) of an mTOR inhibitor is accompanied by a decrease in PD-1 positive immune effector cells, e.g., T cells, an increase in PD-1 negative immune effector cells, e.g., T cells, or an increase in the ratio of in PD-1 negative immune effector cells, e.g., T cells/PD-1 positive immune effector cells, e.g., T cells. PD-1 positive T cells, but not PD-1 negative T cells, can be exhausted by engagement with cells which express a PD-1 ligand, e.g., PD-L1 or PD-L2. Thus, embodiments of the invention are based, at least in part, on the recognition that partial mTOR inhibition, e.g., with low, immune enhancing, dose of an mTOR inhibitor, is associated with a reduction in the percentage of programmed death (PD)-1 positive CD4 and CD8 T lymphocytes.

Accordingly, in one aspect, the present invention relates to a method of promoting an immune response in a subject, e.g., a human subject, comprising, administering to the subject a low, immune enhancing, dose of an mTOR inhibitor, e.g., RAD001 or rapamycin, thereby enhancing or promoting an immune response in the subject.

In an embodiment, a low, immune enhancing, dose of an mTOR inhibitor, e.g., RAD001 or rapamycin and an antigen are administered as a vaccine.

In an embodiment, a low, immune enhancing, dose of an mTOR inhibitor, e.g., RAD001 or rapamycin is administered as an adjuvant composition or compound.

Exemplary mTOR inhibitors are described herein, e.g., in the section below entitled "MTOR INHIBITORS."

In an embodiment, the mTOR inhibitor is an allosteric mTOR inhibitor. In an embodiment, the mTOR inhibitor is a RAD001. In an embodiment, the mTOR inhibitor is rapamycin.

In an embodiment, the mTOR inhibitor is a catalytic inhibitor, e.g., a kinase inhibitor. In an embodiment, the kinase inhibitor is selective for mTOR. In an embodiment, the kinase inhibitor is selected from BEZ235 and CCG168.

In an embodiment, the low, immune enhancing, dose comprises a plurality of mTOR inhibitors. In an embodiment, the low, immune enhancing, dose comprises an allosteric and a catalytic mTOR inhibitor.

In an embodiment, the low, immune enhancing, dose of an mTOR inhibitor is administered for an amount of time sufficient for one or more of the following to occur:
  i) a decrease in the number of PD-1 positive immune effector cells;
  ii) an increase in the number of PD-1 negative immune effector cells;
  iii) an increase in the ratio of PD-1 negative immune effector cells/PD-1 positive immune effector cells;
  iv) an increase in the number of naive T cells;
  v) an increase in the expression of one or more of the following markers: $CD62L^{high}$, $CD127^{high}$, $CD27^+$, and BCL2, e.g., on memory T cells, e.g., memory T cell precursors;
  vi) a decrease in the expression of KLRG1, e.g., on memory T cells, e.g., memory T cell precursors; or
  vii) an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein i), ii), iii), iv), v), vi), or vii) occurs e.g., at least transiently, e.g., as compared to a non-treated subject.

In an embodiment, the method of treating, e.g., promoting an immune response in, a subject, e.g., a human subject, comprises inhibiting a negative immune response mediated by the engagement of PD-1 with PD-L1 or PD-L2.

In an embodiment, the method of treating, e.g., promoting an immune response in, a subject, e.g., a human subject, comprises increasing the number of T cells capable of proliferation.

In an embodiment, the method of treating, e.g., promoting an immune response in, a subject, e.g., a human subject, comprises increasing the number of T cells capable of cytotoxic function, secreting cytokines, or activation.

In an embodiment, the method of treating, e.g., promoting an immune response in, a subject, e.g., a human subject, comprises increasing the number of T cells capable of providing T cell help to B cells.

In an embodiment, the administering of the low, immune enhancing, dose of an mTOR inhibitor results in the partial, but not total, inhibition of mTOR for at least 1, 5, 10, 20, 30, or 60 days.

In an embodiment, the administering of the low, immune enhancing, dose of an mTOR inhibitor results in the partial, but not total, inhibition of mTOR as long as enhancement of the immune response is needed.

In an embodiment, the low, immune enhancing, dose of an mTOR inhibitor is associated with mTOR inhibition of at least 5% but no more than 90%, e.g., as measured by p70

S6K inhibition. In an embodiment, the mTOR inhibitor comprises RAD001. (Methods for evaluation of the level of inhibition of mTOR are described herein, e.g., in the section below entitled "EVALUATION OF MTOR INHIBITION.")

In an embodiment, the low, immune enhancing, dose of an mTOR inhibitor is associated with mTOR inhibition of at least 10% but no more than 80%, e.g., as measured by p70 S6K inhibition. In an embodiment, the mTOR inhibitor comprises RAD001.

In an embodiment, the low, immune enhancing, dose of an mTOR inhibitor is associated with mTOR inhibition of at least 10% but no more than 40%, e.g., as measured by p70 S6K inhibition. In an embodiment, the mTOR inhibitor comprises RAD001.

In an embodiment, administering to the subject a low, immune enhancing, dose of an mTOR inhibitor comprises administering, e.g., once per week, e.g., in an immediate release dosage form, 0.1 to 20, 0.5 to 10, 2.5 to 7.5, 3 to 6, or about 5, mgs of RAD001.

In an embodiment, administering to the subject a low, immune enhancing, dose of an mTOR inhibitor comprises administering, once per week, in an immediate release dosage form, about 5 mgs of RAD001.

In an embodiment, administering to the subject a low, immune enhancing, dose of an mTOR inhibitor comprises administering, e.g., once per week, e.g., in an immediate release dosage form, an amount of an mTOR inhibitor other than RAD001, that is bioequivalent to a one per week, immediate release dosage form of 0.1 to 20, 0.5 to 10, 2.5 to 7.5, 3 to 6, or about 5 mgs of RAD001.

In an embodiment, administering to the subject a low, immune enhancing, dose of an mTOR inhibitor comprises administering, once per week, in an immediate release dosage form, an amount of an mTOR inhibitor other than RAD001, that is bioequivalent to a once per week, immediate release dosage form of about 5 mgs of RAD001.

In an embodiment, administering to the subject a low, immune enhancing, dose of an mTOR inhibitor comprises administering, e.g., once per week, e.g., in a sustained release dosage form, 0.3 to 60, 1.5 to 30, 7.5 to 22.5, 9 to 18, or about 15 mgs of RAD001.

In an embodiment, administering to the subject a low, immune enhancing, dose of an mTOR inhibitor comprises administering, once per week, in a sustained release dosage form, about 15 mgs of RAD001.

In an embodiment, administering to the subject a low, immune enhancing, dose of an mTOR inhibitor comprises administering, e.g., once per week, e.g., in a sustained release dosage form, an amount of an mTOR inhibitor other than RAD001, that is bioequivalent to a once per week, sustained release dosage form of 0.3 to 60, 1.5 to 30, 7.5 to 22.5, 9 to 18, or about 15 mgs of RAD001.

In an embodiment, administering to the subject a low, immune enhancing, dose of an mTOR inhibitor comprises administering, once per week, in a sustained release dosage form, an amount of an mTOR inhibitor other than RAD001, that is bioequivalent to a once per week sustained release dosage form of about 15 mgs of RAD001.

In an embodiment, administering to the subject a low, immune enhancing, dose of an mTOR inhibitor comprises administering, e.g., once per day, e.g., in an immediate release dosage form, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001.

In an embodiment, administering to the subject a low, immune enhancing, dose of an mTOR inhibitor comprises administering once per day, in an immediate release dosage form, about 0.5 mgs of RAD001.

In an embodiment, administering to the subject a low, immune enhancing, dose of an mTOR inhibitor comprises administering, e.g., once per day, e.g., in an immediate release dosage form, an amount of an mTOR inhibitor other than RAD001, that is bioequivalent to a once per day, immediate release dosage form of 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001.

In an embodiment, administering to the subject a low, immune enhancing, dose of an mTOR inhibitor comprises administering, once per day, in an immediate release dosage form, an amount of an mTOR inhibitor other than RAD001, that is bioequivalent to a once per day, immediate release dosage form of about 0.5 mgs of RAD001.

In an embodiment, administering to the subject a low, immune enhancing, dose of an mTOR inhibitor comprises administering, e.g., once per day, e.g., in a sustained release dosage form, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001.

In an embodiment, administering to the subject a low, immune enhancing, dose of an mTOR inhibitor comprises administering, e.g., once per day, e.g., in a sustained release dosage form, an amount of an mTOR inhibitor other than RAD001, that is bioequivalent to a once per day, sustained release dosage form of 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001.

In an embodiment, administering to the subject a low, immune enhancing, dose of an mTOR inhibitor comprises administering, e.g., once per week, e.g., in a sustained release dosage form, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001.

In an embodiment, administering to the subject a low, immune enhancing, dose of an mTOR inhibitor comprises administering, e.g., once per week, e.g., in a sustained release dosage form, an amount of an mTOR inhibitor other than RAD001, that is bioequivalent to a once per week, sustained release dosage form of 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001.

In an embodiment, the mTOR inhibitor is RAD001 and the dose provides for a trough level of RAD001 in a range of between about 0.1 and 3 ng/ml, between 0.3 or less and 3 ng/ml, or between 0.3 or less and 1 ng/ml.

In an embodiment, the mTOR inhibitor is other than RAD001 and the dose is bioequivalent to a dose of RAD001 that provides for a trough level of RAD001 in a range of between about 0.1 and 3 ng/ml, between 0.3 or less and 3 ng/ml, or between 0.3 or less and 1 ng/ml.

In an embodiment the subject has cancer. Exemplary cancers are described herein, e.g., in the section below entitled "DISORDERS Cancer." In an embodiment, the subject has cancer, but is not otherwise immunocompromised, e.g, is not HIV+, does not have AIDS, or is not immunoscenescent. In an embodiment, the subject has cancer, but, except for that due to any anti-cancer treatment, is not otherwise immunocompromised, e.g., is not HIV+, does not have AIDS, or is not immunoscenescent.

In an embodiment, the subject has cancer and the method comprises promoting the subject's immune response to the cancer. In an embodiment, the subject was selected on the basis of having cancer. In an embodiment, the subject was selected on the basis of being in need of, or likely to benefit from, promotion of the immune response. In an embodiment, a cell of the cancer expresses PD-L1 or PD-L2. In an embodiment, a cell in the cancer microenvironment expresses PD-L1 or PD-L2.

In an embodiment, the cancer comprises a solid tumor. In an embodiment, the cancer is a hematological cancer. In an embodiment, the cancer is a leukemia. In an embodiment, the cancer is melanoma.

In an embodiment, promoting an immune response in a subject comprises preparing the subject, e.g., a subject having cancer, for an additional treatment that suppresses the immune system or kills T cells, e.g., administration of a drug, e.g., a chemotherapeutic, or radiation. In an embodiment, the low, immune enhancing dose, of an mTOR inhibitor, e.g., RAD001, reduces immune suppression associated with the additional treatment.

In an embodiment, the method further comprises administering an additional treatment, e.g., a chemotherapeutic, radiation, a cellular therapy, bone marrow transplant to the subject. Inan embodiment the additional treatment comprises a combination of drugs or treatments as described herein, see, e.g., the section below entitled "COMBINATION TREATMENTS." In an embodiment, the method further comprises administering an additional treatment that kills T cells, e.g., radiation or cytotoxic chemotherapy. In an embodiment, the low, immune enhancing, dose of mTOR inhibitor is administered prior to, with, or after the initiation of the additional treatment. In an embodiment, the method further comprises administering an additional treatment for the cancer.

In an embodiment, the method further comprises administering an additional treatment that suppresses the immune system, e.g., administration of a drug, e.g., a chemotherapeutic, or radiation. In an embodiment, the low, immune enhancing, dose of mTOR inhibitor, e.g., RAD001, is administered prior to, with, or after the initiation of the additional treatment that suppresses the immune system. While not wishing to be bound by theory, it is believed that the low, immune enhancing dose of an mTOR inhibitor, allows for a broader range of therapeutic options. Without wishing to be bound by theory, it is believed that this is due to the improvement in the subject's immune responsiveness. In an embodiment, the low, immune enhancing dose of an mTOR inhibitor, can allow for more aggressive administration of the additional treatment. Thus, in an embodiment, the unit dosage, total dosage, frequency of administration, or number of administrations, is increased. In an embodiment, the increase is relative to a reference administration, e.g., the standard of care that is provided in the absence of a low, immune enhancing, dose of mTOR inhibitor. In an embodiment, the increase is relative to an administration that would give the maximum tolerable or acceptable levels of immune suppression, in the absence of a low, immune enhancing, dose of mTOR inhibitor. In another embodiment, the immune enhancing dose of an mTOR inhibitor, can allow for less aggressive administration of the additional treatment. Thus, in an embodiment, the unit dosage, total dosage, frequency of administration, or number of administrations, is decreased. In an embodiment, the decrease is relative to a reference administration, e.g., the standard of care that is provided in the absence of a low, immune enhancing, dose of mTOR inhibitor. In an embodiment, the decrease is relative to an administration that would give the maximum tolerable or acceptable levels of immune suppression, in the absence of a low, immune enhancing, dose of mTOR inhibitor.

In an embodiment, the subject is immunocompromised. In an embodiment, the subject is HIV+ or has AIDs.

Thus, in an embodiment, promoting an immune response in a subject comprises promoting the immune response of an immunocompromised subject, e.g., a subject having an immunodeficiency, e.g., a hereditary or acquired immunodeficiency, e.g., a virally-mediated immunodeficiency, e.g., a subject that is HIV+, or a subject having AIDS. In an embodiment, the method further comprises administering an additional treatment for the immunodeficiency, e.g., an antiviral agent. In an embodiment, the subject is HIV+ or has AIDS and the additional treatment comprises administering an anti-viral agent, e.g., a nucleoside reverse transcriptase inhibitor, e.g., abacavir, didanosine, emtricitabine, lamivudine, stavudine, tenofovir, zalcitabine, or zidovudine, or combinations thereof, e.g. combivir (zidovudine and lamivudine), trizivir (zidovudine, lamivudine and abacavir), epzicom (abacavir and lamivudine) and truvada (tenofovir and lamivudine). In an embodiment, the additional treatment comprises administering a protease inhibitor, e.g., amprenavir, agenerase, atazanavir, fosamprenavir, indinavir, lopinavir, ritonavir, or saquinavir, or a combination thereof. In an embodiment, the low, immune enhancing, dose of mTOR inhibitor, e.g., RAD001, is administered prior to, with, or after the initiation of the additional treatment. While not wishing to be bound by theory, it is believed that the low, immune enhancing dose of an mTOR inhibitor, allows for a broader range of therapeutic options. Without wishing to be bound by theory, it is believed that this is due to the improvement in the subject's immune responsiveness. In an embodiment, the low, immune enhancing dose of an mTOR inhibitor, can allow for more aggressive administration of the additional treatment. Thus, in an embodiment, the unit dosage, total dosage, frequency of administration, or number of administrations, is increased. In an embodiment, the increase is relative to a reference administration, e.g., the standard of care that is provided in the absence of a low, immune enhancing, dose of mTOR inhibitor. In an embodiment, the increase is relative to an administration that would give the maximum tolerable or acceptable levels of a side effect, in the absence of a low, immune enhancing, dose of mTOR inhibitor. In another embodiment, the immune enhancing dose of an mTOR inhibitor, can allow for less aggressive administration of the additional treatment. Thus, in an embodiment, the unit dosage, total dosage, frequency of administration, or number of administrations, is decreased. In an embodiment, the decrease is relative to a reference administration, e.g., the standard of care that is provided in the absence of a low, immune enhancing, dose of mTOR inhibitor. In an embodiment, the decrease is relative to an administration that would give the maximum tolerable or acceptable levels of a side effect, in the absence of a low, immune enhancing, dose of mTOR inhibitor.

In an embodiment, the subject has an infectious disease, e.g., hepatitis, e.g., hepatitis A, B or C, or other pathogenic infection. Exemplary pathogenic infections are described herein, e.g., in the section below entitled "DISORDERS Pathogenic Infections." In an embodiment, the subject has an infectious disease or has a pathogenic infection, but is not otherwise immunocompromised, e.g, is not immunosenescent.

In an embodiment, the subject has an impaired immune response. In an embodiment, the subject is immunosenescent.

In an embodiment, the subject has an age related condition. In an embodiment, the age related condition is selected from the group consisting of sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes.

In an embodiment, the method comprises enhancing an immune response to an antigen in the subject. In an embodiment the method comprises providing or administering to the subject a low, immune enhancing, dose of an mTOR inhibitor, e.g., RAD001 or rapamycin as an adjuvant composition or compound. In an embodiment the method comprises providing or administering to the subject a low, immune enhancing, dose of an mTOR inhibitor, e.g., RAD001 or rapamycin, and the antigen, as a, or in combination with a vaccine. In an embodiment the antigen is a cancer antigen. In an embodiment the antigen is an infectious disease-, viral, bacterial, protozoan, microbial, pathogen-, or parasite-, antigen. In an embodiment, the method further comprises administering an antigen or a vaccine to the subject. In an embodiment, prior to the step of administering, the method comprises a step of identifying a subject having an impaired immune response to an antigen.

In an embodiment, a relatively low baseline or pre-immunization level or titer of antibody to the antigen is predictive of a greater mTOR inhibitor-, e.g., RAD001-, associated increase in antibody titer for an antigen. In an embodiment, the subject is evaluated for level or titer of antibody to the antigen prior to administration of an antigen or vaccine. In an embodiment evaluation comprises acquiring, e.g., directly or indirectly acquiring, a measurement of titer or level of antibody. The titer or level of antibody can be compared with a reference value. Relatively low titer, e.g., titer below or equal to a reference value, is indicative of a greater mTOR inhibitor-, e.g., RAD001-, associated increase in antibody titer. Thus, baseline or pre-immunization titer can be used to select patients for low, immune enhancing, dose of mTOR inhibitor, e.g., in combination with vaccination or administration of antigen to stimulate an immune response. In an embodiment, responsive to a determined level or titer of antibody, a subject is classified as to the likelihood of benefiting from administration of a low, immune enhancing, dose of mTOR inhibitor, e.g., prior to or with administration of a vaccine or antigen. In an embodiment, responsive to a determined level or titer of antibody, e.g., a level or titer that is at or below a reference value, a subject is selected for, or administered, a low, immune enhancing, dose of mTOR inhibitor, prior to or with administration of a vaccine or antigen. In an embodiment, responsive to a determined level or titer of antibody, e.g., a level or titer that is above a reference value, a subject is selected for, or administered an alternative therapy, e.g., administration of a vaccine or antigen, without the administration of a low, immune enhancing, dose of mTOR inhibitor.

In an embodiment, the subject is infected with, or at risk for infection with, an influenza virus, e.g., an influenza A or B virus.

In an embodiment, the method comprises enhancing an immune response to an influenza virus, e.g., an influenza A or B virus. Influenza A viruses are characterized by one or both of two glycoproteins, a hemagglutinin (HA) polypeptide and a neuraminidase (NA) polypeptide, which are displayed on the surface of the virus. There are 17 HA antigens, denoted H1-17, and nine different NA antigens, denoted N1-9.

In such embodiments the antigen or vaccine comprises an influenza antigen, e.g., an influenza A or B antigen. In an embodiment the antigen comprises an HA antigen, e.g., any of H1-17. In an embodiment the antigen is selected from H1N1, H2N2, H3N2, H5N1, H7N7, H1N2, H9N2, H7N2H7N3, H10N7, or H7N9.

In an embodiment, the antigen is selected from H1N1, H2N3, and B influenza subtypes. In an embodiment, the antigen is a pneumococcal antigen.

In an embodiment, the antigen and the mTOR inhibitor are co-administered. In an embodiment, the antigen and the mTOR inhibitor are administered sequentially. In an embodiment, the subject is less than 65 years old.

In an embodiment, a relatively low baseline or pre-immunization level or titer of influenza antibody is predictive of a greater mTOR inhibitor-, e.g., RAD001-, associated increase in antibody titer for the influenza virus, e.g., an influenza A virus. In an embodiment, the subject is evaluated for anti-influenza antibody titer prior to administration of an antigen or vaccine. In an embodiment, evaluation comprises acquiring, e.g., directly or indirectly acquiring, a measurement of anti-influenza antibody titer. The titer of antibody can be compared with a reference value. Relatively low titer, e.g., titer at or below a reference value, e.g., less than or equal to a titer of 1:40 (e.g., as measured herein), is indicative of a greater mTOR inhibitor-, e.g., RAD001-, associated increase in antibody titer. Thus, baseline or pre-immunization titer can be used to select patients for low, immune enhancing, dose of mTOR inhibitor, e.g., in combination with vaccination or administration of antigen to protect against influenza, e.g., influenza A. In an embodiment, responsive to a determined antibody titer, a subject is classified as to the likelihood of benefiting from administration of a low, immune enhancing, dose of mTOR inhibitor, e.g., prior to or with administration of a vaccine or antigen. In an embodiment, responsive to a determined antibody titer, e.g., a titer that is at or below a reference value, a subject is selected for, or administered, a low, immune enhancing, dose of mTOR inhibitor, prior to or with administration of a vaccine or antigen. In an embodiment, responsive to a determined antibody titer, e.g., a titer that is above a reference value, a subject is selected for, or administered an alternative therapy, e.g., administration of a vaccine or antigen without the administration of a low, immune enhancing, dose of mTOR inhibitor.

In an embodiment, the subject does not receive a vaccine, e.g., does not receive a vaccine while the mTOR inhibitor is present at levels which promote the immune response. In an embodiment, the vaccine is an anti-cancer vaccine or a vaccine against an infectious agent. In an embodiment the vaccine is a therapeutic vaccine for a neurological disorder, e.g., Alzheimers.

In an embodiment, the subject does not receive a vaccine, e.g., a cancer vaccine, within 10, 20, 30, 40, 50, 60, 70, 80, or 90 days prior to initiation of the low, immune enhancing, dose of the mTOR inhibitor.

In an embodiment, the subject does not receive a vaccine, e.g., a cancer vaccine, within 10, 20, 30, 40, 50, 60, 70, 80, or 90 days after initiation of the low, immune enhancing, dose of the mTOR inhibitor.

In an embodiment, the low, immune enhancing, dose of a mTOR inhibitor is administered at the time of, or after vaccination. In an embodiment, the low, immune enhancing, dose of a mTOR inhibitor is administered within 24, 10, 5, 4, 3, 2, or 1 hour, prior to, at the time of, or after the vaccination.

In another aspect, the invention features, a method of evaluating a subject for treatment with a low, immune enhancing, dose of mTOR inhibitor, e.g., to promote or enhance an immune response to an influenza vaccine or antigen, comprising:

determining if the baseline or pre-immunization titer of anti-influenza antibody of the subject is equal to or less than 1:40; and responsive to the determination, classifying the subject, e.g., as to the likelihood of benefiting from a low, immune enhancing, dose of RAD001, or selecting a course of therapy for said subject.

In an embodiment, determining comprises directly acquiring the antibody titer.

In an embodiment, determining comprises indirectly acquiring the antibody titer.

In an embodiment, the antibody titer is equal to or less than 1:40 and the subject is classified as likely to benefit from a low, immune enhancing, dose of RAD001.

In an embodiment the antibody titer is equal to or less than 1:40 and the subject is administered a low, immune enhancing, dose of RAD001.

In an embodiment the subject is administered an influenza vaccine or antigen.

In an embodiment the antibody titer is greater than 1:40 and the subject is classified as not likely to benefit from a low, immune enhancing, dose of RAD001.

In another aspect, the invention features a vaccine or vaccine composition comprising a low, immune enhancing, dose of an mTOR inhibitor described herein, e.g., RAD001 or rapamycin, and an antigen.

In an embodiment, the vaccine or vaccine composition comprises a vaccine antigen, and about 0.005 mg to 1.5 mg of the mTOR inhibitor RAD001, or a bioequivalent dose of a different mTOR inhibitor.

In an embodiment, the vaccine or vaccine composition comprises about 0.01-1 mg, about 0.01-0.7 mg, about 0.01-0.5 mg, or about 0.1-0.5 mg of RAD001, or a bioequivalent dose of a different mTOR inhibitor.

In an embodiment, the composition comprises about 0.5 mg of RAD001 or a bioequivalent dose of a different mTOR inhibitor.

In an embodiment, the composition comprises an amount of an mTOR inhibitor sufficient to inhibit P70 S6 kinase activity by no greater than 80% in a subject to which said composition is administered.

In an embodiment, the composition comprises an amount of an mTOR inhibitor sufficient to inhibit P70 S6 kinase activity by no greater than 38% in a subject to which said composition is administered.

In an embodiment, the composition produces at least a 1.2 fold increase in immune response as compared to placebo in a subject to which said composition is administered.

In an embodiment, the mTOR inhibitor is a rapamycin.

In an embodiment, the mTOR inhibitor is a rapalog.

In an embodiment, the vaccine antigen is derived from influenza.

In an embodiment, the vaccine antigen is selected from the group consisting of H1N1, H2N3, and B influenza subtypes.

In an embodiment, the vaccine antigen is derived from pneumococcus.

In another aspect, the invention features, an adjuvant, or adjuvant composition or compound, comprising a low, immune enhancing, dose of an mTOR inhibitor described herein, e.g., RAD001 or rapamycin.

In an embodiment, a vaccine adjuvant comprises about 0.005 mg to 1.5 mg of the mTOR inhibitor RAD001, or a bioequivalent dose of a different mTOR inhibitor.

In an embodiment, a vaccine adjuvant comprises an amount of an mTOR inhibitor sufficient to inhibit P70 S6 kinase activity in a cell by no greater than 80%. In another embodiment, a vaccine adjuvant comprises an amount of an mTOR inhibitor sufficient to inhibit P70 S6 kinase activity in a cell by no greater than 38%.

In an embodiment, the vaccine adjuvant comprises an mTOR inhibitor, wherein the mTOR inhibitor is a rapamycin.

In an embodiment, the vaccine adjuvant comprises an mTOR inhibitor, wherein the mTOR inhibitor is a rapalog.

In an embodiment, the vaccine adjuvant comprises about 0.01-1 mg, 0.01-0.7 mg, 0.01-0.5 mg, or 0.1-0.5 mg of RAD001 or a bioequivalent dose of a different mTOR inhibitor.

In an embodiment, the vaccine adjuvant comprises about 0.5 mg of RAD001 or a bioequivalent dose of a different mTOR inhibitor.

In an aspect, the invention features a method of collecting immune effector cells, e.g., T cells, or preparing a mammal, e.g., a primate, e.g., a human, for collection of T cells to form a preparation of immune effector cells, T cells, wherein the method comprises: administering to the subject a low, immune enhancing dose, of an mTOR inhibitor, e.g., RAD001, or rapamycin, for an amount of time sufficient to decrease the proportion of PD-1 positive immune effector cells, e.g., T cells or increase the proportion of PD-1 negative immune effector cells, e.g., T cells, in the mammal or in a preparation of immune effector cells, e.g., T cells, collected from the mammal.

In an embodiment the method comprises collecting the immune effector cells, e.g., T cells. In an embodiment the method comprises forming an immune effector cell preparation, e.g., a T cell preparation.

In an embodiment, the immune effector cells are T cells. In an embodiment, the T cells are CD4-expressing (CD4+ or CD4) T cells. In an embodiment, the T cells are CD8-expressing (CD8+ or CD8) T cells. In an embodiment, the T cells comprise a plurality of CD4+ T cells and CD8+ T cells.

In an embodiment, the method of collecting immune effector cells further comprises evaluating the level of PD1 negative or PD1 positive immune effector cells, e.g., T cells, in the subject or in T cells taken from the subject.

In an embodiment, the method of collecting immune effector cells further comprises collecting T cells to form the preparation of T cells.

In an embodiment, the method of collecting immune effector cells further comprises providing a preparation of T cells.

In an embodiment, the administering to the subject a low, immune enhancing dose, of an mTOR inhibitor is initiated at least 1, 2, 3, 4, 5, 10, 15, 20, 25, or 30 days prior to collection of T cells.

In an embodiment, the administering to the subject a low, immune enhancing dose, of an mTOR inhibitor is initiated at least 30, 60, 90 or 120 days prior to collection of T cells.

In an embodiment, collection of the T cells is performed within 1, 2, 3, 4, 5, 6, 7, 8, 9, 10, 20, 30, 60, or 90, days after the last administration of a low, immune enhancing dose, of an mTOR inhibitor.

In an embodiment, the administering to the subject a low, immune enhancing dose, of an mTOR inhibitor results in the partial, but not total, inhibition of mTOR for at least at least 1, 2, 3, 4, 5, 10, 15, 20, 25, or 30 days prior to collection of T cells to form a preparation of T cells from the mammal.

In an embodiment, collection of the T cells is performed within 1, 2, 3, 4, 5, 6, 7, 8, 9, 10, 20, 30, 60, or 90, days after a determination has been made that there is partial inhibition of mTOR in the subject.

In an embodiment, collection of the T cells is performed within 1, 2, 3, 4, 5, 6, 7, 8, 9, 10, 20, 30, 60, or 90, days after onset of partial mTOR inhibition in the subject.

In an embodiment, the preparation of T cells comprises a PD-1 negative T cell.

In an embodiment, at least 80-90% of the T cells collected are PD-1 negative.

In an embodiment, no more than 10-20% of the T cells collected are PD-1 positive.

In an embodiment, the mTOR inhibitor is an allosteric mTOR inhibitor. In an embodiment, the mTOR inhibitor is a RAD001. In an embodiment, the mTOR inhibitor is rapamycin.

In an embodiment, the mTOR inhibitor is a catalytic inhibitor, e.g., a kinase inhibitor. In an embodiment, the kinase inhibitor is selective for mTOR. In an embodiment, the kinase inhibitor is selected from BEZ235 and CCG168.

In an embodiment, the low, immune enhancing, dose comprises a plurality of mTOR inhibitors. In an embodiment, the dose comprises an allosteric and a catalytic mTOR inhibitor.

In an embodiment, the low, immune enhancing, dose of an mTOR inhibitor is administered for an amount of time sufficient for one or more of the following to occur:
  i) a decrease in the number of PD-1 positive immune effector cells;
  ii) an increase in the number of PD-1 negative immune effector cells;
  iii) an increase in the ratio of PD-1 negative immune effector cells/PD-1 positive immune effector cells;
  iv) an increase in the number of naive T cells;
  v) an increase in the expression of one or more of the following markers: $CD62L^{high}$, $CD127^{high}$, $CD27^+$, and BCL2, e.g., on memory T cells, e.g., memory T cell precursors;
  vi) a decrease in the expression of KLRG1, e.g., on memory T cells, e.g., memory T cell precursors; or
  vii) an increase in the number of memory T cell precursors, e.g., cells with any one or combination of the following characteristics: increased $CD62L^{high}$, increased $CD127^{high}$, increased $CD27^+$, decreased KLRG1, and increased BCL2;
and wherein i), ii), iii), iv), v), vi), or vii) occurs e.g., at least transiently, e.g., as compared to a non-treated subject.

In an embodiment, the method of treating, e.g., promoting an immune response in, a subject, e.g., a human subject, comprises inhibiting a negative immune response mediated by the engagement of PD-1 with PD-L1 or PD-L2.

In an embodiment, the method of treating, e.g., promoting an immune response in, a subject, e.g., a human subject, comprises increasing the number of T cells capable of proliferation.

In an embodiment, the method of treating, e.g., promoting an immune response in, a subject, e.g., a human subject, comprises increasing the number of T cells capable of cytotoxic function, secreting cytokines, or activation.

In an embodiment, the method of treating, e.g., promoting an immune response in, a subject, e.g., a human subject, comprises increasing the number of T cells capable of providing T cell help to B cells.

In an embodiment, the administering of the low, immune enhancing, dose of an mTOR inhibitor results in the partial, but not total, inhibition of mTOR for at least 1, 5, 10, 20, 30, or 60 days.

In an embodiment, the administering of the low, immune enhancing, dose of an mTOR inhibitor results in the partial, but not total, inhibition of mTOR as long as enhancement of the immune response is needed.

In an embodiment, the low, immune enhancing, dose of an mTOR inhibitor is associated with mTOR inhibition of at least 5 but no more than 90%, e.g., as measured by p70 S6K inhibition. In an embodiment, the mTOR inhibitor comprises RAD001.

In an embodiment, the low, immune enhancing, dose of an mTOR inhibitor is associated with mTOR inhibition of at least 10% but no more than 80%, e.g., as measured by p70 S6K inhibition. In an embodiment, the mTOR inhibitor comprises RAD001.

In an embodiment, the low, immune enhancing, dose of an mTOR inhibitor is associated with mTOR inhibition of at least 10% but no more than 40%, e.g., as measured by p70 S6K inhibition. In an embodiment, the mTOR inhibitor comprises RAD001.

In an embodiment, administering to the subject a low, immune enhancing, dose of an mTOR inhibitor comprises administering, e.g., once per week, e.g., in an immediate release dosage form, 0.1 to 20, 0.5 to 10, 2.5 to 7.5, 3 to 6, or about 5, mgs of RAD001.

In an embodiment, administering to the subject a low, immune enhancing, dose of an mTOR inhibitor comprises administering, once per week, in an immediate release dosage form, about 5 mgs of RAD001.

In an embodiment, administering to the subject a low, immune enhancing, dose of an mTOR inhibitor comprises administering, e.g., once per week, e.g., in an immediate release dosage form, an amount of an mTOR inhibitor other than RAD001, that is bioequivalent to a one per week, immediate release dosage form of 0.1 to 20, 0.5 to 10, 2.5 to 7.5, 3 to 6, or about 5 mgs of RAD001.

In an embodiment, administering to the subject a low, immune enhancing, dose of an mTOR inhibitor comprises administering, once per week, in an immediate release dosage form, an amount of an mTOR inhibitor other than RAD001, that is bioequivalent to a once per week, immediate release dosage form of about 5 mgs of RAD001.

In an embodiment, administering to the subject a low, immune enhancing, dose of an mTOR inhibitor comprises administering, e.g., once per week, e.g., in a sustained release dosage form, 0.3 to 60, 1.5 to 30, 7.5 to 22.5, 9 to 18, or about 15 mgs of RAD001.

In an embodiment, administering to the subject a low, immune enhancing, dose of an mTOR inhibitor comprises administering, once per week, in a sustained release dosage form, about 15 mgs of RAD001.

In an embodiment, administering to the subject a low, immune enhancing, dose of an mTOR inhibitor comprises administering, e.g., once per week, e.g., in a sustained release dosage form, an amount of an mTOR inhibitor other than RAD001, that is bioequivalent to a once per week, sustained release dosage form of 0.3 to 60, 1.5 to 30, 7.5 to 22.5, 9 to 18, or about 15 mgs of RAD001.

In an embodiment, administering to the subject a low, immune enhancing, dose of an mTOR inhibitor comprises administering, once per week, in a sustained release dosage form, an amount of an mTOR inhibitor other than RAD001, that is bioequivalent to a once per week sustained release dosage form of about 15 mgs of RAD001.

In an embodiment, administering to the subject a low, immune enhancing, dose of an mTOR inhibitor comprises administering, e.g., once per day, e.g., in an immediate release dosage form, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001.

In an embodiment, administering to the subject a low, immune enhancing, dose of an mTOR inhibitor comprises administering once per day, in an immediate release dosage form, about 0.5 mgs of RAD001.

In an embodiment, administering to the subject a low, immune enhancing, dose of an mTOR inhibitor comprises administering, e.g., once per day, e.g., in an immediate release dosage form, an amount of an mTOR inhibitor other than RAD001, that is bioequivalent to a once per day, immediate release dosage form of 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001.

In an embodiment, administering to the subject a low, immune enhancing, dose of an mTOR inhibitor comprises administering, once per day, in an immediate release dosage form, an amount of an mTOR inhibitor other than RAD001, that is bioequivalent to a once per day, immediate release dosage form of about 0.5 mgs of RAD001.

In an embodiment, administering to the subject a low, immune enhancing, dose of an mTOR inhibitor comprises administering, e.g., once per day, e.g., in a sustained release dosage form, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001.

In an embodiment, administering to the subject a low, immune enhancing, dose of an mTOR inhibitor comprises administering, e.g., once per day, e.g., in a sustained release dosage form, an amount of an mTOR inhibitor other than RAD001, that is bioequivalent to a once per day, sustained release dosage form of 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001.

In an embodiment, administering to the subject a low, immune enhancing, dose of an mTOR inhibitor comprises administering, e.g., once per week, e.g., in a sustained release dosage form, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001.

In an embodiment, administering to the subject a low, immune enhancing, dose of an mTOR inhibitor comprises administering, e.g., once per week, e.g., in a sustained release dosage form, an amount of an mTOR inhibitor other than RAD001, that is bioequivalent to a once per week, sustained release dosage form of 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001.

In an embodiment, the mTOR inhibitor is RAD001 and the dose provides for a trough level of RAD001 in a range of between about between 0.3 or less and 3 ng/ml, or between 0.3 or less and 1 ng/ml.

In an embodiment, the mTOR inhibitor is other than RAD001 and the dose is bioequivalent to a dose of RAD001 that provides for a trough level of RAD001 in a range of between about between 0.3 or less and 3 ng/ml, or between 0.3 or less and 1 ng/ml.

In an embodiment, the subject has cancer and the method comprises promoting the subject's immune response to the cancer. In an embodiment, the subject was selected on the basis of having cancer. In an embodiment, a cell of the cancer expresses PD-L1 or PD-L2. In an embodiment, a cell in the cancer microenvironment expresses PD-L1 or PD-L2.

In an embodiment, the cancer comprises a solid tumor. In an embodiment, the cancer is a hematological cancer. In an embodiment, the cancer is a leukemia. In an embodiment, the cancer is melanoma. In an embodiment, the cancer is selected from Table 1.

In an embodiment, the subject is immunocompromised. In an embodiment, the subject is HIV+ or has AIDs. In an embodiment, the subject has an infectious disease.

In an embodiment, the subject has an infectious disease, e.g., hepatitis, e.g., hepatitis A, B or C. In an embodiment, the subject has an infectious disease, but is not otherwise immunocompromised, e.g, is not immunosenescent.

In an embodiment, the subject has an impaired immune response. In an embodiment, the subject is immunoscenescent.

In an embodiment, the subject is infected with a virus, bacteria, protozoan, microbe, pathogen, or parasite.

In an embodiment, the subject has an age related condition.

In an embodiment, the subject is less than 65 years old.

In an embodiment, the subject does not receive a vaccine, e.g., does not receive a vaccine while the mTOR inhibitor is present at levels which promote the immune response. In an embodiment, the vaccine is an anti-cancer vaccine or a vaccine against an infectious agent. In an embodiment the vaccine is a therapeutic vaccine for a neurological disorder, e.g., Alzheimers disease.

In an embodiment, the subject does not receive a vaccine, e.g., a cancer vaccine, within 10, 20, 30, 40, 50, 60, 70, 80, or 90 days prior to initiation of the low, immune enhancing, dose of the mTOR inhibitor.

In an embodiment, the subject does not receive a vaccine, e.g., a cancer vaccine, within 10, 20, 30, 40, 50, 60, 70, 80, or 90 days after initiation of the low, immune enhancing, dose of the mTOR inhibitor.

In an embodiment, the low, immune enhancing, dose of an mTOR inhibitor is administered at the time of, or after vaccination.

In an aspect, a preparation of human T cells, e.g., as made by a method described herein, enriched for PD-1 negative T cells is provided herein. In an embodiment, the subject has cancer or is immunocompromised.

In another aspect, the invention features, a preparation of T cells, e.g., human T cells, achievable by, or which could be made by, practice of a method described herein.

In another aspect, the invention features a unit dosage form, composition, or formulation, of an mTOR inhibitor, e.g., RAD001, e.g., a dosage form suitable for oral administration. Embodiments are described herein, e.g., in the section below entitled "Low-Dose mTOR Inhibitors". Unit dosage forms or compositions can be provided as immediate or sustained release formulations, se, e.g., the sections below entitled "Pharmaceutical Compositions" and "Sustained Release."

BRIEF DESCRIPTION OF THE DRAWINGS

1A, the increase above baseline in influenza geometric mean titers to each of the 3 influenza vaccine strains (H1N1 A/California/07/2009, H3N2 A/Victoria/210/2009, B/Brisbane/60/2008) relative to the increase in the placebo cohort 4 weeks after vaccination is shown for each of the RAD001 dosing cohorts in the intention to treat population. The bold black line indicates the 1.2 fold increase in titers relative to placebo that is required to be met for 2 out of 3 influenza vaccine strains to meet the primary endpoint of the study. The star "*" indicates that the increase in GMT titer relative to placebo exceeds 1 with posterior probability of at least 80%. FIG. 1B is a graph of the same data as in FIG. 1A for the subset of subjects with baseline influenza titers <=1:40.

FIG. 5A shows there was a significant decrease (−37.1-−28.5%) in PD-1-positive CD4 T cells at week 12 in cohorts receiving RAD001 at dose levels 0.5 mg/Day (n=25), 5 mg/Week (n=29) and 20 mg/Week (n=30) as compared to the placebo cohort (n=25) with p=0.002 (0.02), p=0.003 (q=0.03), and p=0.01 (q=0.05) respectively. FIG. 5B shows there was a significant decrease (−43.3-−38.5%) in PD-1-positive CD8 T cells at week 12 in cohorts receiving RAD001 (n=109) at dose levels 0.5 mg/Day (n=25), 5 mg/Week (n=29) and 20 mg/Week (n=30) as compared to the placebo cohort (n=25) with p=0.01 (0.05), p=0.007 (q=0.04), and p=0.01 (q=0.05) respectively.

FIG. 5C shows was a significant increase (3.0-4.9%) in PD-1-negative CD4 T cells at week 12 in cohorts receiving RAD001 (n=109) at dose levels 0.5 mg/Day (n=25), 5 mg/Week (n=29) and 20 mg/Week (n=30) as compared to the placebo cohort (n=25) with p=0.0007 (0.02), p=0.03 (q=0.07), and p=0.03 (q=0.08) respectively.

FIG. 6A shows a significant decrease of 30.2% in PD-1+CD4 T cells at week 6 in the pooled RAD cohort (n=84) compared to placebo cohort (n=25) with p=0.03 (q=0.13). The decrease in PD-1-positive CD4 T cells at week 12 in the pooled RAD as compared to the placebo cohort is 32.7% with p=0.05 (q=0.19). FIG. 6B shows a significant decrease of 37.4% in PD-1-positive CD8 T cells at week 6 in the pooled RAD001 cohort (n=84) compared to placebo cohort (n=25) with p=0.008 (q=0.07). The decrease in PD-1-positive CD8 T cells at week 12 in the pooled RAD001 as compared to the placebo cohort is 41.4% with p=0.066 (q=0.21). FIGS. 6A and 6B represent the data in FIGS. 5A, 5B, and 5C but with the different RAD001 dosage groups of FIGS. 5A, 5B, and 5C pooled into the single RAD001-treated group in FIGS. 6A and 6B.

FIG. 8A depicts P70 S6 kinase inhibition with higher doses of weekly and daily RAD001; FIG. 8B depicts P70 S6 kinase inhibition with lower doses of weekly RAD001.

DETAILED DESCRIPTION

Definitions

Figure 1A:
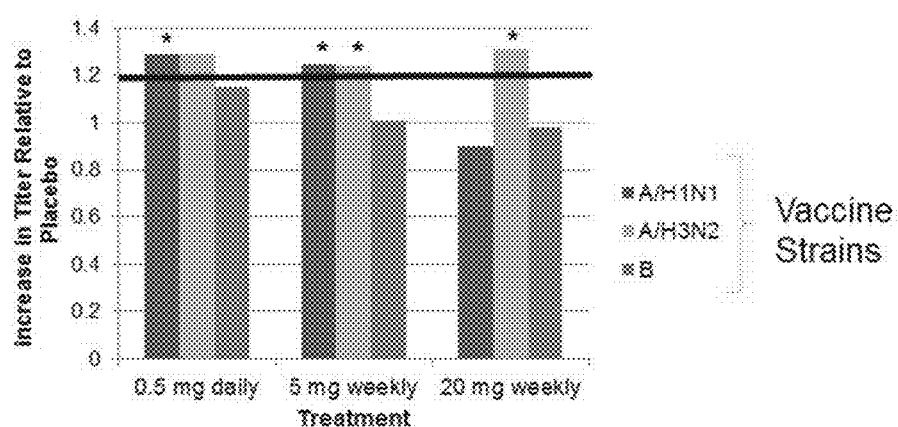
FIGS. 1A and 1B are graphs showing an increase in titers to influenza vaccine strains as compared to placebo. In FIG.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, refers to variations of ±20% or in some instances ±10%, or in some instances ±5%, or in some instances ±1%, or in some instances ±0.1% from the specified value, as such variations are appropriate to perform the disclosed methods.

The term "adjuvant" refers to a compound that, when used in combination with a specific immunogen, e.g., a vaccine immunogen, in a formulation, augments or otherwise alters, modifies or enhances the resultant immune responses.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the compounds (e.g., mTOR inhibitors), peptides, polynucleotides, cells and antibodies of the invention in prevention of the occurrence of tumor in the first place.

The term "antibody," refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "antigen presenting cell" or "APC" refers to an immune system cell such as an accessory cell (e.g., a B-cell, a dendritic cell (DC), and the like) that displays a foreign antigen complexed with major histocompatibility complexes (MHC's) on its surface. T-cells may recognize these complexes using their T-cell receptors (TCRs). APCs process antigens and present them to T-cells.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In an embodiment, a cancer is characterized by expression of a PD-1 ligand, e.g., PD-L1 or PD-L2, on a cancer cell or in a tumor microenvironment. The term "cancer" is refers to all types of cancerous growths or oncogenic processes, metastatic tissues or malignantly transformed cells, tissues, or organs, irrespective of histopathologic type or stage of invasiveness.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. In one aspect of the methods described herein, an mTOR inhibitor and an antigen may be co-administered.

The term "effective amount" or "therapeutically effective amount" are used interchangeably herein, and refer to an amount of a compound, formulation, material, or composition, as described herein effective to achieve a particular biological result.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "fully human" refers to an immunoglobulin, such as an antibody or antibody fragment, where the whole molecule is of human origin or consists of an amino acid sequence identical to a human form of the antibody or immunoglobulin.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules being compared is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

The terms "immunosenescence or immunosenescent" refer to a decrease in immune function resulting in impaired immune response, e.g., to cancer, vaccination, infectious pathogens, among others. It involves both the host's capacity to respond to infections and the development of long-term immune memory, especially by vaccination. This immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria. Immunosenescence is a multifactorial condition leading to many pathologically significant health problems, e.g., in the aged population. Age-dependent biological changes such as depletion of hematopoietic stem cells, an increase in PD1+ lymphocytes, a decline in the total number of phagocytes and NK cells and a decline in humoral immunity contribute to the onset of immunosenescence. In one aspect, immunosenescence can be measured in an individual by measuring telomere length in immune cells (See, e.g., U.S. Pat. No. 5,741,677). Immunosenescence can also be determined by documenting in an individual a lower than normal number of naïve CD4 and/or CD8 T cells, T cell repertoire, the number of PD1-expressing T cells, e.g., a lower than normal number of PD-1 negative T cells, or response to vaccination in a subject greater than or equal to 65 years of age.

The term "impaired immune response" refers to a state in which a subject does not have an appropriate immune response, e.g., to cancer, vaccination, pathogen infection, among others. In some embodiments, a subject having an impaired immune response is predicted not to get protective antibody titer levels following prophylactic vaccination, or in which a subject does not have a decrease in disease burden after therapeutic vaccination. A subject can also have an impaired immune response if the subject is a member of a population known to have decreased immune function or that has a history of decreased immune function such as the elderly, subjects undergoing chemotherapy treatment, asplenic subjects, immunocompromised subjects, or subjects having HIV/AIDS. Methods described herein allow for the treatment of an impaired immune response by administration of a low, immune enhancing, dose of an mTOR inhibitor, e.g., an allosteric mTOR inhibitor, such as RAD001.

The term "isolated" refers to altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^+$, decreased KLRG1, and increased BCL2; wherein any of the changes described above occurs, e.g., at least transiently, e.g., as compared to a non-treated subject.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, or at least 70 but no more than 90%.

In an embodiment, a dose of an mTOR inhibitor is associated with, or provides, mTOR inhibition of at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, or at least 60 but no more than 80%.

In an embodiment, a dose of an mTOR inhibitor is associated with, or provides, mTOR inhibition of at least 5 but no more than 70%, at least 10 but no more than 70%, at least 15, but no more than 70%, at least 20 but no more than 70%, at least 30 but no more than 70%, at least 40 but no more than 70%, or at least 50 but no more than 70%.

In an embodiment, a dose of an mTOR inhibitor is associated with, or provides, mTOR inhibition of at least 5 but no more than 60%, at least 10 but no more than 60%, at least 15, but no more than 60%, at least 20 but no more than 60%, at least 30 but no more than 60%, or at least 40 but no more than 60%.

In an embodiment, a dose of an mTOR inhibitor is associated with, or provides, mTOR inhibition of at least 5 but no more than 50%, at least 10 but no more than 50%, at least 15, but no more than 50%, at least 20 but no more than 50%, at least 30 but no more than 50%, or at least 40 but no more than 50%.

In an embodiment, a dose of an mTOR inhibitor is associated with, or provides, mTOR inhibition of at least 5 but no more than 40%, at least 10 but no more than 40%, at least 15, but no more than 40%, at least 20 but no more than 40%, at least 30 but no more than 40%, or at least 35 but no more than 40%.

In an embodiment, a dose of an mTOR inhibitor is associated with, or provides, mTOR inhibition of at least 5 but no more than 30%, at least 10 but no more than 30%, at least 15, but no more than 30%, at least 20 but no more than 30%, 30%, or at least 25 but no more than 30%.

In an embodiment, a dose of an mTOR inhibitor is associated with, or provides, mTOR inhibition of at least 1, 2, 3, 4 or 5 but no more than 20%, at least 1, 2, 3, 4 or 5 but no more than 30%, at least 1, 2, 3, 4 or 5, but no more than 35, at least 1, 2, 3, 4 or 5 but no more than 40%, or at least 1, 2, 3, 4 or 5 but no more than 45%.

In an embodiment, a dose of an mTOR inhibitor is associated with, or provides, mTOR inhibition of at least 1, 2, 3, 4 or 5 but no more than 90%.

As is discussed herein, the extent of mTOR inhibition can be expressed as the extent of P70 S6K inhibition, e.g., the extent of mTOR inhibition can be determined by the level of decrease in P70 S6K activity, e.g., by the decrease in phosphorylation of a P70 S6K substrate. The level of mTOR inhibition can be evaluated by a method described herein, e.g. by the Boulay assay.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The terms "acquire" or "acquiring" as used herein, refer to obtaining possession of a physical entity (e.g., a sample), or a value, e.g., a numerical value, or image, by "directly acquiring" or "indirectly acquiring" the physical entity or value. "Directly acquiring" means performing a process (e.g., performing a synthetic or analytical method, contacting a sample with a detection reagent, or capturing a signal from a sample) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; inducing or collecting a signal, e.g., a light based signal, e.g., a fluorescent signal, or by changing the structure of a reagent, or a fragment or other derivative thereof, e.g., by breaking or forming a covalent or non-covalent bond, between a first and a second atom of the reagent. Directly acquiring a value includes methods in which a computer or detection device, e.g, a scanner is used, e.g., when a change in electronic state responsive to impingement of a photon on a detector. Directly acquiring a value includes capturing a signal from a sample.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "parenteral" administration of an immunogenic composition includes, e.g., subcutaneous (s.c.), intravenous (i.v.), intramuscular (i.m.), or intrasternal injection, intratumoral, or infusion techniques.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

"Prodrug", or "pro-drug" refers to a compound that is processed, in the body of a subject, into a drug. In an embodiment the processing comprises the breaking or formation of a bond, e.g., a covalent bond. Typically, breakage of a covalent bond releases the drug.

The term "promote" or "enhance" in the context of an immune response refers to an increase in immune response, such as an increase in the ability of immune cells to target and/or kill cancer cells, to target and/or kill pathogens and pathogen infected cells, and protective immunity following vaccination, among others. In some embodiments, protective immunity refers to the presence of sufficient immune response (such as antibody titers) to protect against subsequent infection by a pathogen expressing the same antigen.

The term "prophylaxis" refers to the prevention of or protective treatment for a disease or disease state. Prevention may be complete, e.g., the total absence of a disease or disease state. The prevention may also be partial, such that the likelihood of the occurrence of the disease or disease state in a subject is less likely to occur than had the subject not received the prophylactic treatment.

As used herein, the term "rapalog" refers to a small molecule analog of rapamycin.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "specifically binds," refers to an antibody, or a ligand, which recognizes and binds with a cognate binding partner (e.g., a molecule present on a T cell) protein present in a sample, but the antibody or ligand does not substantially recognize or bind other molecules in the sample.

The term "subject", refers to any living organisms in which an immune response can be elicited (e.g., mammals, human). In an embodiment the subject is a human. A subject may be of any age. In an embodiment the subject is an elderly human subject, e.g., 65 years of age or older. In an embodiment, a subject is a human subject who is not an elderly, e.g., less than 65 years of age. In an embodiment, a subject is a human pediatric subject, e.g., 18 years of age or less. In an embodiment, a subject is an adult subject, e.g., older than 18 years of age.

The term "therapeutic" refers to a treatment. A therapeutic effect is obtained by reduction, suppression, remission, or eradication of a disease state.

The term "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, non-Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

"Unit dosage form" as the term is used herein refers to a dosage suitable for one administration. By way of example a unit dosage form can be a tablet, a capsule, or an amount of therapeutic disposed in a delivery device, e.g., a syringe or intravenous drip bag. In an embodiment a unit dosage form is administered in a single administration. In an embodiment more than one unit dosage form, e.g., two tablets, can be administered simultaneously. The term "vaccine" refers to a composition, such as a suspension or solution of antigen or antigenic moieties, usually containing an antigen (e.g., an inactivated infectious agent, or some part of the infectious agent, a tumor antigen, among others) that is injected or otherwise introduced into the body to produce active immunity. The antigen or antigenic moiety making up the vaccine can be a live or killed microorganism, or a natural product purified from a microorganism or other cell including, but not limited to tumor cells, a synthetic product, a genetically engineered protein, peptide, polysaccharide or similar product or an allergen. The antigen or antigenic moiety can also be a subunit of a protein, peptide, polysaccharide or similar product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

The term "preparation of T cells," refers to a preparation that comprises at least one T cell. In an embodiment it is enriched for T cell as compared to peripheral blood.

The term a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

mTOR Inhibitors

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

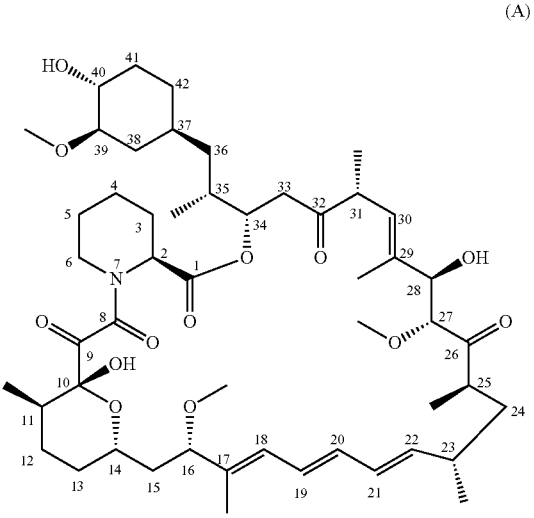 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

(A)

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-0-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. Pat. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

In mammalian cells, the target of rapamycin (mTOR) kinase exists as a multiprotein complex described as the mTORC1 complex or mTORC2 complex, which senses the availability of nutrients and energy and integrates inputs from growth factors and stress signaling. The mTORC1 complex is sensitive to allosteric mTOR inhibitors such as rapamycin, is composed of mTOR, GβL, and regulatory associated proteins of mTOR (raptor), and binds to the peptidyl-prolyl isomerase FKBP12 protein (a FK506-binding protein 1A, 12 kDa). In contrast, the mTORC2 complex is composed of mTOR, GβL, and rapamycin-insensitive companion proteins of mTOR (rictor), and does not bind to the FKBP12 protein in vitro.

The mTORC1 complex has been shown to be involved in protein translational control, operating as a growth factor and nutrient sensitive apparatus for growth and proliferation regulation. mTORC1 regulates protein translation via two key downstream substrates: P70 S6 kinase, which in turn phosphorylates ribosomal protein P70 S6, and eukaryotic translation initiation factor 4E binding protein 1 (4EBP1), which plays a key role in modulating eIF4E regulated cap-dependent translation. The mTORC1 complex regulates cell growth in response to the energy and nutrient homeostasis of the cell, and the deregulation of mTORC1 is common in a wide variety of human cancers. The function of mTORC2 involves the regulation of cell survival via phosphorylation of Akt and the modulation of actin cytoskeleton dynamics.

The mTORC1 complex is sensitive to allosteric mTOR inhibitors such as rapamycin and derivatives in large part due to rapamycin's mode of action, which involves the formation of an intracellular complex with the FKBP12 and binding to the FKBP12-rapamycin binding (FRB) domain of mTOR. This results in a conformational change in mTORC1 which is believed to alter and weaken the interaction with its scaffolding protein raptor, in turn impeding substrates such as P70 S6K1 from accessing mTOR and being phosphorylated. Rapamycin and rapalogues such as RAD001 have gained clinical relevance by inhibiting hyperactivation of mTOR associated with both benign and malignant proliferation disorders.

RAD001, otherwise known as everolimus (Afinitor®), has the chemical name (1R,9S,12S,15R,16E,18R,19R,21R,23 S,24E,26E,28E,30S,32S,35R)-1,18-dihydroxy-12-{(1R)-2-[(1 S,3R,4R)-4-(2-hydroxyethoxy)-3-methoxycyclohexyl]-1-methyl ethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone and the following chemical structure

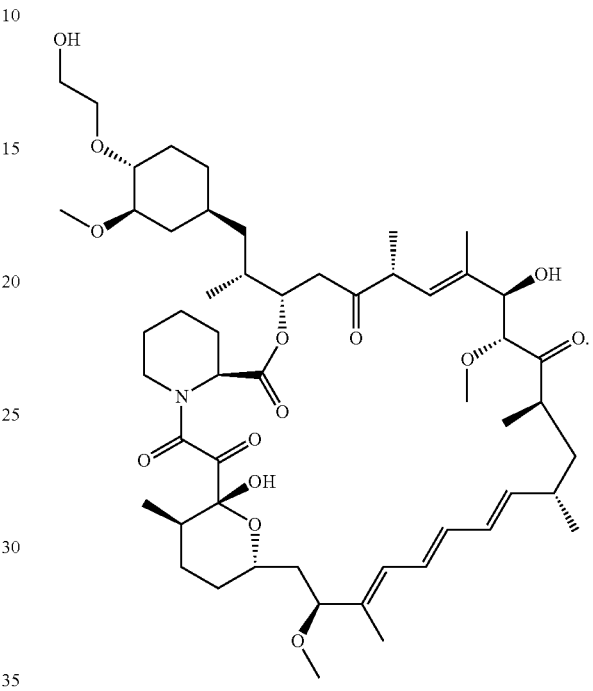

Everolimus is an FDA approved drug for the treatment of advanced kidney cancer and is being investigated in several other phase III clinical trials in oncology. Preclinical studies have shown that Everolimus is able to inhibit the proliferation of a wide variety of tumor cell lines both in vitro and in vivo, presumably through the suppression of rapamycin sensitive mTORC1 function. Everolimus, as a derivative of rapamycin, is an allosteric mTOR inhibitor that is highly potent at inhibiting part of the mTORC1 function, namely P70 S6 kinase (P70 S6K) and the downstream P70 S6K substrate P70 S6. Allosteric mTOR inhibitors like everolimus (and other rapamycin analogs) have little or no effect at inhibiting the mTORC2 pathway, or its resulting activation of Akt signaling. Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTOR inhibitors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more complete inhibitors of mTORC1 than such allosteric mTOR inhibitors as rapamycin, because they modulate rapamycin-resistant mTORC1 outputs such as 4EBP1-T37/46 phosphorylation and cap-dependent translation.

BEZ235 is a catalytic mTOR inhibitor, having the chemical name 2-methyl-2-[4-(3-methyl-2-oxo-8-quinolin-3-yl-2,3-dihydro-imidazo[4,5-c]quinolin-1-yl)-phenyl]-propionitrile and the following chemical structure

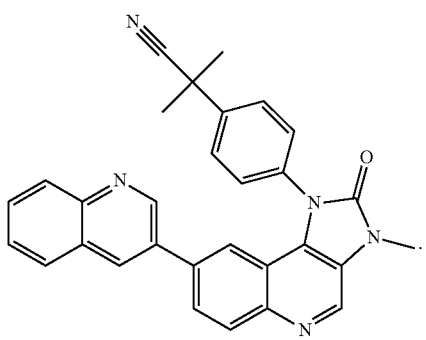 [SMILES: Cn1c(=O)n(-c2ccc(C(C)(C)C#N)cc2)c2c3cc(-c4cnc5ccccc5c4)ccc3ncc21]

BEZ235 may also be used in its monotosylate salt form. The synthesis of BEZ235 is described in WO2006/122806.

As a catalytic mTOR inhibitor BEZ235 is capable of shutting down the complete function of mTORC1 complex, including both the rapamycin sensitive (phosphorylation of P70 S6K, and subsequently phosphorylation of P70 S6) and rapamycin insensitive (phosphorylation of 4EBP1) functions. BEZ235 has a differential effect according to the drug concentration used, whereby mTOR inhibition predominates at a low concentration (less than 100 nmol/L) but dual PI3K/mTOR inhibition at relatively higher concentrations (approximately 500 nmol/L), Serra et al., 2008.

Another catalytic mTOR inhibitor described in the literature is CCG168 (otherwise known as AZD-8055, Chresta, C. M., et al., Cancer Res, 2010, 70(1), 288-298) which has the chemical name {5-[2,4-bis-((S)-3-methyl-morpholin-4-yl)-pyrido[2,3d]pyrimidin-7-yl]-2-methoxy-phenyl}-methanol and the following chemical structure

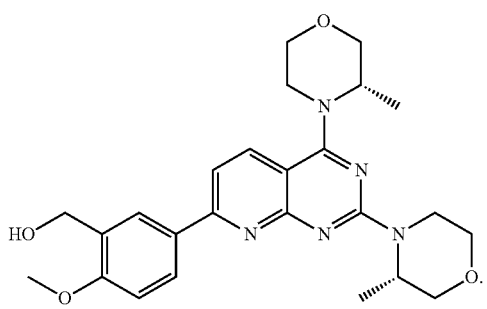 [SMILES: COc1ccc(-c2ccc3c(N4CCOC[C@@H]4C)nc(N4CCOC[C@@H]4C)nc3n2)cc1CO]

Another catalytic mTOR inhibitor described in the literature is 3-[2,4-bis[(3S)-3-methylmorpholin-4-yl]pyrido[2,3-d]pyrimidin-7-yl]-N-methylbenzamide (WO09104019) having the following chemical structure:

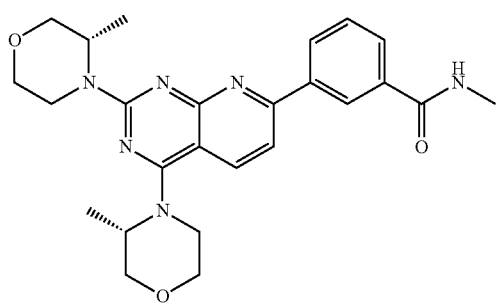 [SMILES: CNC(=O)c1cccc(-c2ccc3c(N4CCOC[C@@H]4C)nc(N4CCOC[C@@H]4C)nc3n2)c1]

Another catalytic mTOR inhibitor described in the literature is 3-(2-aminobenzo[d]oxazol-5-yl)-1-isopropyl-1H-pyrazolo[3,4-d]pyrimidin-4-amine (WO10051043 and WO2013023184) having following chemical structure:

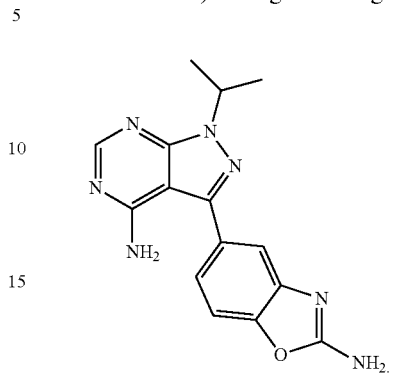

Another catalytic mTOR inhibitor described in the literature is N-(3-(N-(3-((3,5-dimethoxyphenyl)amino)quinoxaline-2-yl)sulfamoyl)phenyl)-3-methoxy-4-methylbenzamide (WO07044729 and WO12006552) having the following chemical structure:

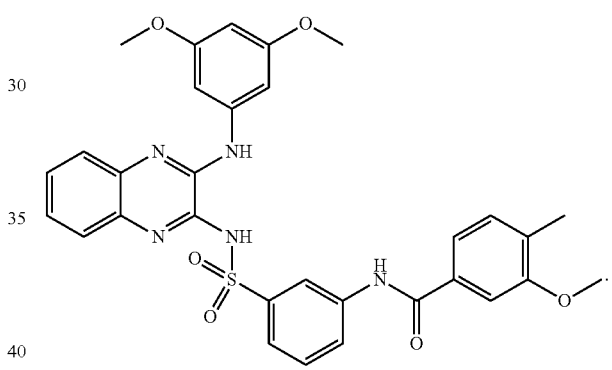

Another catalytic mTOR inhibitor described in the literature is PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea and having the following chemical structure:

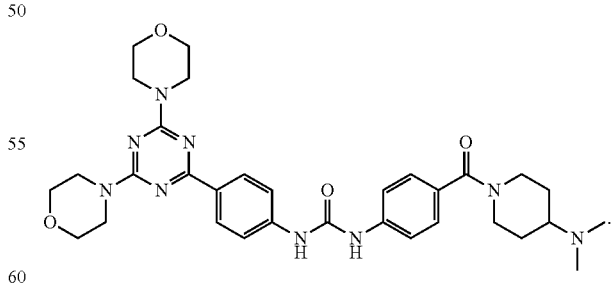

Another catalytic mTOR inhibitor described in the literature is GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide and having the following chemical structure:

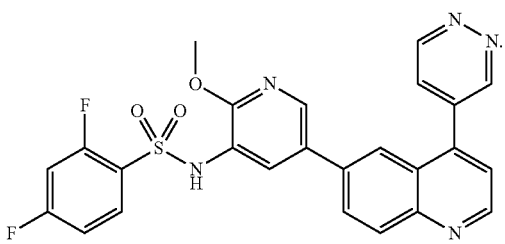 [SMILES: COc1ncc(-c2ccc3nccc(-c4ccnnc4)c3c2)cc1NS(=O)(=O)c1ccc(F)cc1F]

Another catalytic mTOR inhibitor described in the literature is 5-(9-isopropyl-8-methyl-2-morpholino-9H-purin-6-yl)pyrimidin-2-amine (WO10114484) having the following chemical structure:

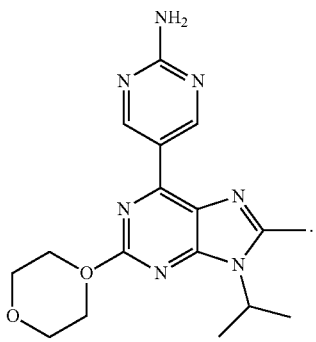

Another catalytic mTOR inhibitor described in the literature is (E)-N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (WO12007926) having the following chemical structure:

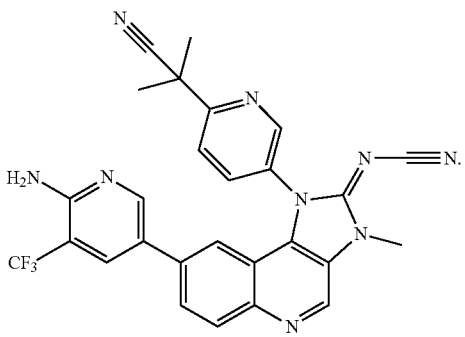 [SMILES: Cn1/c(=N\C#N)n(-c2ccc(C(C)(C)C#N)nc2)c2c3cc(-c4cnc(N)c(C(F)(F)F)c4)ccc3ncc21]

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTor inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing. mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Downstream Inhibitors

Many of the methods described herein rely on the use of a low, immune enhancing, dose of an mTOR inhibitors, e.g., to increase the level of PD1 negative immune effector cells, e.g., T cells, to decrease the level of PD1 positive immune effector cells, e.g., T cells, to increase the ratio of PD1 negative immune effector cells, e.g., T cells/PD1 positive immune effector cells, e.g., T cells, to increase the level of naive T cells, or to increase the number of memory T cell precursors or the expression level of memory T cell precursor markers. Any of these methods can also be practiced with, in place of the low, immune enhancing, dose of an mTOR inhibitors, the administration of an inhibitor of a downstream element in the pathway, e.g., P70 S6K or mTORC1. Examples of inhibitors of P70 S6K include PF-4708671 (Pfizer) or LY2584702 tosylate (Eli Lilly). Examples of inhibitors of mTORC1 include allosteric mTOR inhibitors that specifically inhibit mTORC1, but do not inhibit mTORC2. In an embodiment, a downstream inhibitor is administered at a dose effective to increase the level of PD1 negative immune effector cells, e.g., T cells, to decrease the level of PD1 positive immune effector cells, e.g., T cells, to increase the ratio of PD1 negative immune effector cells, e.g., T cells/PD1 positive immune effector cells, e.g., T cells, to increase the level of naive T cells, or to increase the number of memory T cell precursors or the expression level of memory T cell precursor markers.

Evaluation of mTOR Inhibition mTOR phosphorylates the kinase P70 S6, thereby activating P70 S6K and allowing it to phosphorylate its substrate. The extent of mTOR inhibition can be expressed as the extent of P70 S6K inhibition, e.g., the extent of mTOR inhibition can be determined by the level of decrease in P70 S6K activity, e.g., by the decrease in phosphorylation of a P70 S6K substrate. One can determine the level of mTOR inhibition, by measuring P70 S6K activity (the ability of P70 S6K to phsophorylate a substrate), in the absence of inhibitor, e.g., prior to administration of inhibitor, and in the presence of inhibitor, or after the administration of inhibitor. The level of inhibition of P70 S6K gives the level of mTOR inhibition. Thus, if P70 S6K is inhibited by 40%, mTOR activity, as measured by P70 S6K activity, is inhibited by 40%. The extent or level of inhibition referred to herein is the average level of inhibition over the dosage interval. By way of example, if the inhibitor is given once per week, the level of inhibition is given by the average level of inhibition over that interval, namely a week.

Boulay et al., *Cancer Res,* 2004, 64:252-61, hereby incorporated by reference, teaches an assay that can be used to assess the level of mTOR inhibition (referred to herein as the Boulay assay). In an embodiment, the assay relies on the measurement of P70 S6 kinase activity from biological samples before and after administration of an mTOR inhibitor, e.g., RAD001. Samples can be taken at preselected times after treatment with an mTOR inhibitor, e.g., 24, 48, and 72 hours after treatment. Biological samples, e.g., from skin or peripheral blood mononuclear cells (PBMCs) can be used. Total protein extracts are prepared from the samples. P70 S6 kinase is isolated from the protein extracts by immunoprecipitation using an antibody that specifically recognizes the P70 S6 kinase. Activity of the isolated P70 S6 kinase can be measured in an in vitro kinase assay. The isolated kinase can be incubated with 40S ribosomal subunit substrates (which is an endogenous substrate of P70 S6K) and gamma-$^{32}$P under conditions that allow phosphorylation of the substrate. Then the reaction mixture can be resolved on an SDS-PAGE gel, and $^{32}$P signal analyzed using a PhosphorImager. A $^{32}$P signal corresponding to the size of the 40S ribosomal subunit indicates phosphorylated substrate and the activity of P70 S6K. Increases and decreases in kinase activity can be calculated by quantifying the area and intensity of the $^{32}$P signal of the phosphorylated substrate (e.g., using ImageQuant, Molecular Dynamics), assigning arbitrary unit values to the quantified signal, and comparing the values from after administration with values from before administration or with a reference value. For example, percent inhibition of kinase activity can be calculated with the following formula: 1-(value obtained after administration/value obtained before administration)×100. As described above, the extent or level of inhibition referred to herein is the average level of inhibition over the dosage interval.

Methods for the evaluation of kinase activity, e.g., P70 S6 kinase activity, are also provided in U.S. Pat. No. 7,727,950, hereby incorporated by reference.

The level of mTOR inhibition can also be evaluated by a change in the ration of PD1 negative to PD1 positive T cells. T cells from peripheral blood can be identified as PD1 negative or positive by art-known methods.

Low-Dose mTOR Inhibitors

Methods described herein use low, immune enhancing, dose mTOR inhibitors, doses of mTOR inhibitors, e.g., allosteric mTOR inhibitors, including rapalogs such as RAD001. In contrast, levels of inhibitor that fully or near fully inhibit the mTOR pathway are immunosuppressive and are used, e.g., to prevent organ transplant rejection. In addition, high doses of rapalogs that fully inhibit mTOR also inhibit tumor cell growth and are used to treat a variety of cancers (See, e.g., Antineoplastic effects of mammalian target of rapamycine inhibitors. Salvadori M. World J Transplant. 2012 October 24; 2(5):74-83; Current and Future Treatment Strategies for Patients with Advanced Hepatocellular Carcinoma: Role of mTOR Inhibition. Finn R S. Liver Cancer. 2012 November; 1(3-4):247-256; Emerging Signaling Pathways in Hepatocellular Carcinoma. Moeini A, Cornelia H, Villanueva A. Liver Cancer. 2012 September; 1(2):83-93; Targeted cancer therapy—Are the days of systemic chemotherapy numbered? Joo W D, Visintin I, Mor G. Maturitas. 2013 Sep. 20.; Role of natural and adaptive immunity in renal cell carcinoma response to VEGFR-TKIs and mTOR inhibitor. Santoni M, Berardi R, Amantini C, Burattini L, Santini D, Santoni G, Cascinu S. Int J Cancer. 2013 Oct. 2).

The present invention is based, at least in part, on the surprising finding that doses of mTOR inhibitors well below those used in current clinical settings had a superior effect in increasing an immune response in a subject and increasing the ratio of PD-1 negative T cells/PD-1 positive T cells. It was surprising that low doses of mTOR inhibitors, producing only partial inhibition of mTOR activity, were able to effectively improve immune responses in human subjects and increase the ratio of PD-1 negative T cells/PD-1 positive T cells.

Alternatively, or in addition, without wishing to be bound by any theory, it is believed that low, a low, immune enhancing, dose of an mTOR inhibitor can increase naive T cell numbers, e.g., at least transiently, e.g., as compared to a non-treated subject. Alternatively or additionally, again while not wishing to be bound by theory, it is believed that treatment with an mTOR inhibitor after a sufficient amount of time or sufficient dosing results in one or more of the following:

an increase in the expression of one or more of the following markers: CD62L$^{high}$, CD127$^{high}$, CD27$^+$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased CD62L$^{high}$, increased CD127$^{high}$, increased CD27$^+$, decreased KLRG1, and increased BCL2;

and wherein any of the changes described above occurs, e.g., at least transiently, e.g., as compared to a non-treated subject (Araki, K et al. (2009) *Nature* 460:108-112). Memory T cell precursors are memory T cells that are early in the differentiation program. For example, memory T cells have one or more of the following characteristics: increased CD62L$^{high}$, increased CD127$^{high}$, increased CD27$^+$, decreased KLRG1, and/or increased BCL2.

Accordingly, in one aspect, the present invention provides compositions, e.g., provides as a unit dosage form, comprising an mTOR inhibitor, e.g., a allosteric mTOR inhibitor, e.g., RAD001, at a concentration of about 0.005-1.5 mg, about 0.005-1.5 mg, about 0.01-1 mg, about 0.01-0.7 mg, about 0.01-0.5 mg, or about 0.1-0.5 mg. In a further aspect the present invention provides compositions comprising an mTOR inhibitor, e.g., RAD001, at a concentration of 0.005-1.5 mg, 0.005-1.5 mg, 0.01-1 mg, 0.01-0.7 mg, 0.01-0.5 mg, or 0.1-0.5 mg. More particularly, in one aspect, the invention provides compositions comprising an mTOR inhibitor, e.g., RAD001, at a dose of about 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, or 1.0 mg. In one aspect, the mTOR inhibitor, e.g., RAD001, is at a dose of 0.5 mg or less. In a still further aspect, the mTOR inhibitor, e.g., RAD001, is at a dose of about 0.5 mg. In a further aspect, the invention provides compositions comprising an mTOR inhibitor, e.g., RAD001, at a dose of 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, or 1.0 mg. In one aspect, the mTOR inhibitor, e.g., RAD001, is at a dose of 0.5 mg or less. In a still further aspect, the mTOR inhibitor, e.g., RAD001, is at a dose of 0.5 mg.

In a further aspect, the invention relates to compositions comprising an mTOR inhibitor that is not RAD001, in an amount that is bioequivalent to the specific amounts or doses specified for RAD001.

In a further aspect, the invention relates to compositions comprising an mTOR inhibitor in an amount sufficient to inhibit P70 S6 kinase by no greater than 80%. In a further aspect the compositions described herein comprise an mTOR inhibitor in an amount sufficient to inhibit P70 S6 kinase by no greater than 38%.

In an embodiment, the invention relates to a composition, or dosage form, of an mTOR inhibitor, e.g., an allosteric mTOR inhibitor, e.g., a rapalog, rapamycin, or RAD001, or a catalytic mTOR inhibitor, which, when administered on a selected dosing regimen, e.g., once daily or once weekly, is associated with: a level of mTOR inhibition that is not associated with complete, or significant immune suppression, but is associated with enhancement of the immune response.

In a further aspect, the invention provides methods for enhancing immune response, e.g., treating immunosenescence, comprising a step of administering to a subject an mTOR inhibitor. In some embodiments, an mTOR inhibitor, e.g., an allosteric mTOR inhibitor, e.g., RAD001, can be administered at a dose of about 0.005-1.5 mg daily, about 0.01-1 mg daily, about 0.01-0.7 mg daily, about 0.01-0.5 mg daily, or about 0.1-0.5 mg daily. In a further aspect, an mTOR inhibitor, e.g., RAD001, can be administered at a dose of about 0.1-20 mg weekly, about 0.5-15 mg weekly, about 1-10 mg weekly, or about 3-7 mg weekly. In some embodiments, an mTOR inhibitor, e.g., RAD001, can be administered at a dose of 0.005-1.5 mg daily, 0.01-1 mg daily, 0.01-0.7 mg daily, 0.01-0.5 mg daily, or 0.1-0.5 mg daily. In some embodiments, an mTOR inhibitor, e.g., RAD001, can be administered at a dose of about 0.1-20 mg weekly, 0.5-15 mg weekly, 1-10 mg weekly, 3-7 mg weekly, or 5 mg weekly.

In a further aspect, the invention relates to methods for enhancing immune response, e.g., treating immunosenescence, comprising the step of administering an mTOR inhibitor that is not RAD001, in an amount that is bioequivalent to the specific amounts or doses described herein for RAD001.

In some embodiments, an mTOR inhibitor, e.g., a allosteric mTOR inhibitor, eg., e.g., RAD001, can be administered at a dose of about 0.005 mg daily, 0.006 mg daily, 0.007 mg daily, 0.008 mg daily, 0.009 mg daily, 0.01 mg daily, 0.02 mg daily, 0.03 mg daily, 0.04 mg daily, 0.05 mg daily, 0.06 mg daily, 0.07 mg daily, 0.08 mg daily, 0.09 mg daily, 0.1 mg daily, 0.2 mg daily, 0.3 mg daily, 0.4 mg daily, 0.5 mg daily, 0.6 mg daily, 0.7 mg daily, 0.8 mg daily, 0.9 mg daily, or 1.0 mg daily. In some embodiments, RAD001 can be administered at a dose of no greater than about 0.7 mg in a 24 hour period. In some embodiments, an mTOR inhibitor, e.g., an allosteric mTOR inhibitor, e.g., RAD001, can be administered at a dose of no greater than about 0.5 mg in a 24 hour period. In some embodiments, RAD001 can be administered at a dose of 0.5 mg or less daily. In some embodiments, RAD001 can be administered at a dose of 0.5 mg daily.

In a further aspect, the invention can utilize an mTOR inhibitor other than RAD001 in an amount that is bioequivalent to the specific amounts or doses specified for RAD001.

In some embodiments, an mTOR inhibitor, e.g., an allosteric mTOR inhibitor, e.g., RAD001, can be administered at a dose of 0.1 mg weekly, 0.2 mg weekly, 0.3 mg weekly, 0.4 mg weekly, 0.5 mg weekly, 0.6 mg weekly, 0.7 mg weekly, 0.8 mg weekly, 0.9 mg weekly, 1 mg weekly, 2 mg weekly, 3 mg weekly, 4 mg weekly, 5 mg weekly, 6 mg weekly, 7 mg weekly, 8 mg weekly, 9 mg weekly, 10 mg weekly, 11 mg weekly, 12 mg weekly, 13 mg weekly, 14 mg weekly, 15 mg weekly, 16 mg weekly, 17 mg weekly, 18 mg weekly, 19 mg weekly, or 20 mg weekly. In some embodiments, an mTOR inhibitor, e.g., an allosteric mTOR inhibitor, e.g., RAD001, is administered at a dose of 5 mg or less weekly. In some embodiments, an mTOR inhibitor, e.g., an allosteric mTOR inhibitor, e.g., RAD001, is administered at a dose of 5 mg weekly.

In some embodiments, the invention can utilize an mTOR inhibitor other than RAD001 in an amount that is bioequivalent to the specific amounts or doses specified for RAD001.

An mTOR inhibitor, e.g., an allosteric mTOR inhibitor, e.g., a rapalog, rapamycin, or RAD001, or a catalytic mTOR inhibitor, can be provided in a sustained release formulation. Any of the compositions or unit dosage forms described herein can be provided in a sustained release formulation. In some embodiments, a sustained release formulation will have lower bioavailability than an immediate release formulation. E.g., in embodiments, to attain a similar therapeutic effect of an immediate release formation a sustained release formulation will have from about 2 to about 5, about 2.5 to about 3.5, or about 3 times the amount of inhibitor provided in the immediate release formulation.

In an embodiment, immediate release forms, e.g., of RAD001, typically used for one administration per week, having 0.1 to 20, 0.5 to 10, 2.5 to 7.5, 3 to 6, or about 5, mgs per unit dosage form, are provided. For once per week administrations, these immediate release formulations correspond to sustained release forms, having, respectively, 0.3 to 60, 1.5 to 30, 7.5 to 22.5, 9 to 18, or about 15 mgs of an mTOR inhibitor, e.g., an allosteric mTOR inhibitor, e.g., rapamycin or RAD001. In embodiments both forms are administered on a once/week basis.

In an embodiment, immediate release forms, e.g., of RAD001, typically used for one administration per day, having 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs per unit dosage form, are provided. For once per day administrations, these immediate release forms correspond to sustained release forms, having, respectively, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of an mTOR inhibitor, e.g., an allosteric mTOR inhibitor, e.g., rapamycin or RAD001. For once per week administrations, these immediate release forms correspond to sustained release forms, having, respectively, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of an mTOR inhibitor, e.g., an allosteric mTOR inhibitor, e.g., rapamycin or RAD001.

In an embodiment, immediate release forms, e.g., of RAD001, typically used for one administration per day, having 0.01 to 1.0 mgs per unit dosage form, are provided. For once per day administrations, these immediate release forms correspond to sustained release forms, having, respectively, 0.03 to 3 mgs of an mTOR inhibitor, e.g., an allosteric mTOR inhibitor, e.g., rapamycin or RAD001. For once per week administrations, these immediate release forms correspond to sustained release forms, having, respectively, 0.2 to 20 mgs of an mTOR inhibitor, e.g., an allosteric mTOR inhibitor, e.g., rapamycin or RAD001.

In an embodiment, immediate release forms, e.g., of RAD001, typically used for one administration per week, having 0.5 to 5.0 mgs per unit dosage form, are provided. For once per week administrations, these immediate release forms correspond to sustained release forms, having, respectively, 1.5 to 15 mgs of an mTOR inhibitor, e.g., an allosteric mTOR inhibitor, e.g., rapamycin or RAD001.

As described above, one target of the mTOR pathway is the P70 S6 kinase. Thus, doses of mTOR inhibitors which are useful in the methods and compositions described herein are those which are sufficient to achieve no greater than 80% inhibition of P70 S6 kinase activity relative to the activity of the P70 S6 kinase in the absence of an mTOR inhibitor, e.g., as measured by an assay described herein, e.g., the Boulay assay. In a further aspect, the invention provides an amount of an mTOR inhibitor sufficient to achieve no greater than 38% inhibition of P70 S6 kinase activity relative to P70 S6 kinase activity in the absence of an mTOR inhibitor, e.g., as measured by an assay described herein, e.g., the Boulay assay. In one aspect the dose of mTOR inhibitor useful in the methods and compositions of the invention is sufficient to achieve, e.g., when administered to a human subject, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10% or less inhibition of P70 S6 kinase activity, e.g., as measured by an assay described herein, e.g., the Boulay assay.

In one aspect the dose of mTOR inhibitor useful in the methods and compositions of the invention is sufficient to achieve, e.g., when administered to a human subject, 90+/−5% (i.e., 85-95%), 89+/−5%, 88+/−5%, 87+/−5%, 86+/−5%, 85+/−5%, 84+/−5%, 83+/−5%, 82+/−5%, 81+/−5%, 80+/−5%, 79+/−5%, 78+/−5%, 77+/−5%, 76+/−5%, 75+/−5%, 74+/−5%, 73+/−5%, 72+/−5%, 71+/−5%, 70+/−5%, 69+/−5%, 68+/−5%, 67+/−5%, 66+/−5%, 65+/−5%, 64+/−5%, 63+/−5%, 62+/−5%, 61+/−5%, 60+/−5%, 59+/−5%, 58+/−5%, 57+/−5%, 56+/−5%, 55+/−5%, 54+/−5%, 54+/−5%, 53+/−5%, 52+/−5%, 51+/−5%, 50+/−5%, 49+/−5%, 48+/−5%, 47+/−5%, 46+/−5%, 45+/−5%, 44+/−5%, 43+/−5%, 42+/−5%, 41+/−5%, 40+/−5%, 39+/−5%, 38+/−5%, 37+/−5%, 36+/−5%, 35+/−5%, 34+/−5%, 33+/−5%, 32+/−5%, 31+/−5%, 30+/−5%, 29+/−5%, 28+/−5%, 27+/−5%, 26+/−5%, 25+/−5%, 24+/−5%, 23+/−5%, 22+/−5%, 21+/−5%, 20+/−5%, 19+/−5%, 18+/−5%, 17+/−5%, 16+/−5%, 15+/−5%, 14+/−5%, 13+/−5%, 12+/−5%, 11+/−5%, or 10+/−5%, inhibition of P70 S6 kinase activity, e.g., as measured by an assay described herein, e.g., the Boulay assay.

P70 S6 kinase activity in a subject may be measured using methods known in the art, such as, for example, according to the methods described in U.S. Pat. No. 7,727,950, by immunoblot analysis of phosphoP70 S6K levels and/or phosphoP70 S6 levels or by in vitro kinase activity assays.

In a further aspect, the invention relates to compositions comprising an mTOR inhibitor such as an mTOR inhibitor, e.g., an allosteric mTOR inhibitor, e.g., RAD001. Doses of an mTOR inhibitor, e.g., an allosteric mTOR inhibitor, e.g., RAD001, in such compositions can be in the range of about 30 pM to 4 nM. In one aspect, the dose of an mTOR inhibitor, e.g., an allosteric mTOR inhibitor, e.g., RAD001, is in the range of about 50 pM to 2 nM, about 100 pM to 1.5 nM, about 200 pM to 1 nM, or about 300 pM to 500 pM. In one aspect, the dose of RAD001 is in the range of 50 pM to 2 nM, 100 pM to 1.5 nM, 200 pM to 1 nM, or 300 pM to 500 pM. In a further aspect the dose of RAD001 is about 30 pM, 40 pM, 50 pM, 60 pM, 70 pM, 80 pM, 90 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1 nM, 1.5 nM, 2 nM, 2.5 nM, 3 nM, 3.5 nM, or 4 nM.

In a further aspect, the invention can utilize an mTOR inhibitor other than RAD001 in an amount that is bioequivalent to the specific amounts or doses specified for RAD001.

The invention further relates to methods comprising the administration of an mTOR inhibitor to a subject. Such methods may employ doses of the mTOR inhibitor RAD001 in the range of about 30 pM to 4 nM. In a further aspect, the dose of RAD001 can be in the range of about 50 pM to 2 nM, about 100 pM to 1.5 nM, about 200 pM to 1 nM, or about 300 pM to 500 pM. In one aspect, the dose of RAD001 is in the range of 50 pM to 2 nM, 100 pM to 1.5 nM, 200 pM to 1 nM, or 300 pM to 500 pM. In a further aspect the dose of RAD001 is about 30 pM, 40 pM, 50 pM, 60 pM, 70 pM, 80 pM, 90 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1 nM, 1.5 nM, 2 nM, 2.5 nM, 3 nM, 3.5 nM, or 4 nM.

In a further aspect, the methods of the invention can utilize an mTOR inhibitor other than RAD001 in an amount that is bioequivalent to the specific amounts or doses specified for RAD001.

As used herein, the term "about" in reference to a dose of mTOR inhibitor refers to up to a +/−10% variability in the amount of mTOR inhibitor, but can include no variability around the stated dose.

In some embodiments, the invention provides methods comprising administering to a subject an mTOR inhibitor, e.g., an allosteric inhibitor, e.g., RAD001, at a dosage within a target trough level. In some embodiments, the trough level is significantly lower than trough levels associated with dosing regimens used in organ transplant and cancer patients. In an embodiment mTOR inhibitor, e.g., RAD001, or rapamycin, is administered to result in a trough level that is less than ½, ¼, ¹⁄₁₀, or ¹⁄₂₀ of the trough level that results in immunosuppression or an anticancer effect. In an embodiment mTOR inhibitor, e.g., RAD001, or rapamycin, is administered to result in a trough level that is less than ½, ¼, ¹⁄₁₀, or ¹⁄₂₀ of the trough level provided on the FDA approved packaging insert for use in immunosuppression or an anticancer indications.

In an embodiment a method disclosed herein comprises administering to a subject an mTOR inhibitor, e.g., an allosteric inhibitor, e.g., RAD001, at a dosage that provides a target trough level of 0.1 to 3 ng/ml, 0.1 to 2 ng/ml, or 0.1 to 1 ng/ml.

In an embodiment a method disclosed herein comprises administering to a subject an mTOR inhibitor, e.g., an allosteric inhibitor, e.g., RAD001, at a dosage that provides a target trough level of 00.2 to 3 ng/ml, 0.2 to 2 ng/ml, or 0.2 to 1 ng/ml.

In an embodiment a method disclosed herein comprises administering to a subject an mTOR inhibitor, e.g. an, allosteric inhibitor, e.g., RAD001, at a dosage that provides a target trough level of 0.3 to 3 ng/ml, 0.3 to 2 ng/ml, or 0.3 to 1 ng/ml.

In an embodiment a method disclosed herein comprises administering to a subject an mTOR inhibitor, e.g., an allosteric inhibitor, e.g., RAD001, at a dosage that provides a target trough level of 0.4 to 3 ng/ml, 0.4 to 2 ng/ml, or 0.4 to 1 ng/ml.

In an embodiment a method disclosed herein comprises administering to a subject an mTOR inhibitor, e.g., an allosteric inhibitor, e.g., RAD001, at a dosage that provides a target trough level of 0.5 to 3 ng/ml, 0.5 to 2 ng/ml, or 0.5 to 1 ng/ml.

In an embodiment a method disclosed herein comprises administering to a subject an mTOR inhibitor, e.g., an allosteric inhibitor, e.g., RAD001, at a dosage that provides a target trough level of 1 to 3 ng/ml, or 1 to 2 ng/ml.

As used herein, the term "level" refers to the concentration of a drug in plasma just before the next dose, or the minimum drug concentration between two doses.

In some embodiments, a target trough level of RAD001 is in a range of between about 0.1 and 3 ng/ml. In an embodiment, the target trough level is below 3 ng/ml, e.g., is between 0.3 or less and 3 ng/ml. In an embodiment, the target trough level is below 3 ng/ml, e.g., is between 0.3 or less and 1 ng/ml. In some embodiments, a target trough level of RAD001 is in a range of between about 2.4 and 3. In some embodiments, a target trough level of RAD001 is in a range of between about 0.1 and 2.4 ng/ml. In some embodiments, a target trough level of RAD001 is in a range of between about 0.1 and 1.5 ng/ml. In some embodiments, a target trough level of RAD001 is in a range of between 0.1 and 3 ng/ml. In some embodiments, a target trough level of RAD001 is in a range of between 2.4 and 3 ng/ml. In some embodiments, a target trough level of RAD001 is in a range of between 0.1 and 2.4 ng/ml. In some embodiments, a target trough level of RAD001 is in a range of between 0.1 and 1.5 ng/ml. In some embodiments, a target trough level of RAD001 is 0.1 ng/ml. In some embodiments, a target trough level of RAD001 is 0.2 ng/ml. In some embodiments, a target trough level of RAD001 is 0.3 ng/ml. In some embodiments, a target trough level of RAD001 is 0.4 ng/ml. In some embodiments, a target trough level of RAD001 is 0.5 ng/ml. In some embodiments, a target trough level of RAD001 is 0.6 ng/ml. In some embodiments, a target trough level of RAD001 is 0.7 ng/ml. In some embodiments, a target trough level of RAD001 is 0.8 ng/ml. In some embodiments, a target trough level of RAD001 is 0.9 ng/ml. In some embodiments, a target trough level of RAD001 is 1.0 ng/ml. In some embodiments, a target trough level of RAD001 is 1.1 ng/ml. In some embodiments, a target trough level of RAD001 is 1.2 ng/ml. In some embodiments, a target trough level of RAD001 is 1.3 ng/ml. In some embodiments, a target trough level of RAD001 is 1.4 ng/ml. In some embodiments, a target trough level of RAD001 is 1.5 ng/ml. In some embodiments, a target trough level of RAD001 is less than 3 ng/ml. In some embodiments, a target trough level of RAD001 is less than 2.5 ng/ml. In some embodiments, a target trough level of RAD001 is less than 3 ng/ml, 2 ng/ml, 1.9 ng/ml, 1.8 ng/ml, 1.7 ng/ml, 1.6 ng/ml, 1.5 ng/ml, 1.4 ng/ml, 1.3 ng/ml, 1.2 ng/ml, 1.1 ng/ml, 1.0 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, or 0.1 ng/ml.

In a further aspect, the invention can utilize an mTOR inhibitor other than RAD001 in an amount that is associated with a target trough level that is bioequivalent to the specified target trough level for RAD001. In an embodiment, the target trough level for an mTOR inhibitor other than RAD001, is a level that gives the same level of mTOR inhibition (e.g., as measured by a method described herein, e.g., the inhibition of P70 S6K) as does a trough level of RAD001 described herein.

Disorders

Cancer

The methods described herein can be used with any cancer. In an embodiment, the cancer comprises a solid tumor. In an embodiment, the cancer is a hematological cancer. The cancer can be a carcinoma, a sarcoma, a myeloma, a leukemia, a lymphoma or a mixed type.

In some embodiments, the cancer is associated with elevated percentages of PD1+ T cells in the subject. In certain embodiments, the cancer is a cancer that generally responds to PD-1 targeted drugs, such as melanoma. In certain embodiments, the cancer is a cancer that generally responds to T-cell directed immunotherapies, such as renal cell carcinoma. In an embodiment the cancer is one in which can be treated by increasing the ration of PD-1 negative to PD-1 positive T cells.

Examples of cancers that can be treated with methods disclosed herein include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

Examples of solid tumors that can be treated with methods disclosed herein include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention.

Methods described herein can be used to treat any of the following cancers:

Digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer;

Endocrine cancers such as islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor;

Eye cancers such as intraocular melanoma; and retinoblastoma;

Musculoskeletal cancers such as Ewing's family of tumors; osteosarcoma/malignant fibrous histiocytoma of the bone; childhood rhabdomyosarcoma; soft tissue sarcoma including adult and childhood soft tissue sarcoma; clear cell sarcoma of tendon sheaths; and uterine sarcoma;

Breast cancer such as breast cancer including childhood and male breast cancer and pregnancy;

Neurologic cancers such as childhood brain stem glioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and childhood supratentorial primitive neuroectodermal tumors and pituitary tumor;

Genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor;

Germ cell cancers such as childhood extracranial germ cell tumor; extragonadal germ cell tumor; ovarian germ cell tumor; and testicular cancer;

Head and neck cancers such as lip and oral cavity cancer; oral cancer including childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer;

Lung cancer such as non-small cell lung cancer; and small cell lung cancer;

Respiratory cancers such as malignant mesothelioma, adult; malignant mesothelioma, childhood; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer;

Skin cancers such as Kaposi's sarcoma; Merkel cell carcinoma; melanoma; and childhood skin cancer;

AIDS-related malignancies;

Other childhood cancers, unusual cancers of childhood and cancers of unknown primary site;

and metastases of the aforementioned cancers can also be treated or prevented in accordance with the methods described herein.

Methods described herein can be used to treat a hematological cancer or malignancy or precancerous condition, e.g., a leukemia or a lymphoma. The cancer can be one associated with expression of a cancer associated antigen as described herein. Hematological cancers and malignancies include, one or more acute leukemias including, e.g., B-cell acute Lymphoid Leukemia ("BALL"), T-cell acute Lymphoid Leukemia ("TALL"), acute lymphoid leukemia (or acute lymphoblastic leukemia) (ALL), including adult and childhood acute lymphoid leukemia; acute myeloid leukemia, including adult and childhood acute myeloid leukemia; one or more chronic leukemias, e.g., chronic myelogenous leukemia (CIVIL), Chronic Lymphoid Leukemia (or chronic lymphocytic leukemia) (CLL). Additional cancers or hematologic conditions that can be treated with methods disclosed herein include, e.g., AIDS-related lymphoma, B cell prolymphocytic leukemia, blastic plasmacytoid dendritic cell neoplasm, Burkitt's lymphoma, chronic myeloproliferative disorders; cutaneous T-cell lymphoma, diffuse large B cell lymphoma, Follicular lymphoma, Hairy cell leukemia, Hodgkin's lymphoma (including adult and childhood Hogkin's lymphoma and Hodgkin's lymphoma during pregnancy), small cell- or a large cell-follicular lymphoma, malignant lymphoproliferative conditions, MALT lymphoma, mantle cell lymphoma, Marginal zone lymphoma, multiple myeloma, multiple myeloma/plasma cell neoplasm, myelodysplasia and myelodysplastic syndrome, myelodysplastic/myeloproliferative disorders, mycosis fungoides, non-Hodgkin's lymphoma (including adult and childhood non-Hodgkin's lymphoma and non-Hodkin's lymphoma during pregnancy), plasmablastic lymphoma, plasmacytoid dendritic cell neoplasm, Sezary syndrome, Waldenstrom macroglobulinemia, primary central system lymphoma, and "preleukemia" which are a diverse collection of hematological conditions united by ineffective production (or dysplasia) of myeloid blood cells, and the like. Further a disease associated with a cancer associated antigen as described herein expression include, but not limited to, e.g., atypical and/or non-classical cancers, malignancies, precancerous conditions or proliferative diseases associated with expression of a cancer associated antigen as described herein.

Pathogenic Infections

In another aspect, the methods provided herein can be used to treat infection by a pathogen in a subject. In some embodiments, the pathogen is a viral pathogen, e.g., a viral pathogen e.g. HIV, meningitis causing viruses, encephalitis causing viruses, Hepatitis A, Hepatitis B, Hepatitis C, rabies virus, polio virus, influenza virus, parainfluenza virus, adenovirus, rhinovirus, measles virus, mumps virus, rubella, pertussis, papilloma virus, yellow fever virus, respiratory syncytial virus, parvovirus, Norwalk virus, chikungunya virus, haemorrhagic fever viruses, dengue virus, and Herpes viruses, e.g., varicella, cytomegalovirus and Epstein-Barr virus. In some embodiments, the infection is a viral infection, such as a chronic viral infection. In some embodiments, a chronic viral infection is selected from Hepatitis A, Hepatitis B, Hepatitis C, Epstein Barr Virus, HIV, Cytomegalovirus, Herpes Simplex Virus 1, Herpes Simplex Virus 2, Human Papillomavirus, Adenovirus, and Kaposi's Sarcoma-Associated Herpesvirus. In some embodiments, a chronic viral infection comprises HIV.

For example, Lichterfeld and colleagues observed that HIV-specific CD8+ T-cells showed reduced telomere length and an increase in telomere length and telomerase activity upon inhibition of PD-1 (see e.g., Lichterfeld, M et al. (2008) Blood 112(9):3679-3687). In another example, PD-1 was significantly upregulated in hepatitis C (HVC)-specific CD8+ cytotoxic T lymphocytes (see e.g., Golden-Mason, L (2007) J. Virol. 81(17): 9249-9258).

In some embodiments, a viral infection comprises a viral acute lower respiratory tract infection. In some embodiments viral acute lower respiratory tract infection is caused by a rhinovirus, coronavirus, influenza virus, respiratory syncytial virus (RSV), adenovirus, and/or parainfluenza. In some embodiments, a viral acute lower respiratory tract infection is pnemonia. In some embodiments, a viral acute lower respiratory tract infection includes a lung abcess. In some embodiments, a viral acute lower respiratory tract infection includes bronchitis.

In some embodiments, the pathogen is a bacterial pathogen, e.g., a bacterial pathogen selected from *Meningococcus, Haemophilus, Pneumococcus, Staphylococcus, Streptococcus, Neisseria, Moraxella, Escherichia coli, Klebsiella, Pseudomonas, Enterobacter, Proteus, Serratia, Legionella, Salmonella, Shigella, Acinetobacer, Listeria, Chlamydia, Mycobacterium* among others.

In some embodiments, the pathogen is a parasitic pathogen, e.g., *Toxoplasma, Leishmania* and malaria, *T. cruzii*, Helminth, e.g., *Schistosoma*.

In some embodiments, the pathogen is a yeast or fungal pathogen, e.g., *Candida, Cryptococcus* or *Coccidioides*.

Senescence and Other Disorders

In another aspect, the methods provided herein can be used to treat senescence in a subject. As used herein, the term "senescence" is meant to include all types of aging. In some embodiments, senescence comprises immunosenescence. Immunosenescence includes reduced immune response to infection with age and results from thymic involution in T-cell lineages, resulting in decreased T cell production and export (see e.g., Shimatani, K et al. (2009) PNAS 106 (37):15807-15812). In some embodiments, there is an increase in population of a bona fide age-dependent CD4+ T cell population defined by a constitutive expression of PD-1, which is induced only transiently on activation in regular T cells and, therefore, reduced immune response to infection (see e.g., Shimatani, K et al. (2009) PNAS 106 (37):15807-15812). In some embodiments, there is in increase in population of CD8+ T cell population defined by increased expression of PD-1 upon receptor-mediated activation of CD8+ T cells (see e.g., Nunes, C et al. (2012) Clinical Cancer Research 18(3):678-687). In some embodiments, senescence comprises cellular senescence, in which a cell no longer divides. In some embodiments, age-related immunosenescence comprises decreased production of naive lymphocytes by hematopoietic stem cells (Chen, Science Signaling, ra75, 2009). Cellular senescence is correlated with the progressive shortening of telomeres that occurs with each cell division.

The term "age-related condition" refers to any disease, disorder, or pathology whose incidence in a population or severity in an individual correlates with the progression of age. More specifically, an age-related condition is a disease, disorder, or pathology whose incidence is at least 1.5 fold higher among human individuals greater than 60 years of age relative to human individuals between the ages of 30-40 and in a selected population of greater than 100,000 individuals. In one aspect, the invention relates to the treatment of conditions including, but not limited to sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes.

Antigens and Vaccines

The mTOR inhibitors, such as RAD001, described herein can be used in combination with an antigen to enhance an immune response to the antigen in a subject. The antigens selected for the methods and compositions of the invention are not a limitation on this invention. The antigen may be, without limitation, a whole cell, a virus, a protein, a protein subunit or fragment. Examples of viral antigens which may be enhanced by administration with an mTOR inhibitor, include, without limitation, those derived from and/or useful in treatment or prevention of HIV, meningitis and encephalitis-causing viruses, Hepatitis A, Hepatitis B, Hepatitis C, rabies virus, polio virus, influenza virus, measles virus, mumps virus, rubella, pertussis, papilloma virus, yellow fever virus, respiratory syncytial virus, parvovirus, chikungunya virus, haemorrhagic fever viruses, and Herpes viruses, particularly, varicella, cytomegalovirus and Epstein-Barr virus. Examples of bacterial and mycobacterial antigens include those derived from and/or useful against *meningococcus, haemophilus, pneumococcus, staphylococcus*, leprosy and tuberculosis among others. Examples of parasitic antigens include those derived from and/or useful against such infections as toxoplasmosis, leishmaniasis and malaria. Still other composition antigens include those derived from a protozoan, e.g., *T. cruzii*, or against a helminth, e.g., *Schistosoma*. Still other antigens useful in the methods described herein include those derived from yeast or fungus such as *Cryptococcus* or *Coccidioides*. Still other antigens useful in the methods described herein include those derived from pathologic tissues such as tumors.

In particular an mTOR inhibitor such as RAD001 can be used in combination with a vaccine against a viral or pathogenic agent, such as an influenza vaccine, pneumococcal vaccine, or HIV vaccine. More specifically, an mTOR inhibitor can be used as described herein to enhance the immune response to, or adjuvant a vaccine for any influenza strain, such as H1N1, H2N3, and B influenza subtypes.

It is further anticipated that an mTOR inhibitor can be used as an adjuvant in therapeutic vaccines for certain cancers and solid tumors, and infectious diseases including, without limitation, malaria, HIV, and influenza. Such a therapeutic vaccine is used in a manner similar to that disclosed above for its use as an adjuvant for vaccines containing antigens of a pathogenic microorganism or virus. Particularly where the tumor antigen by itself has been unsuccessful in activating a response to a particular cancer, the use of an mTOR inhibitor as an adjuvant in a cancer vaccine or therapeutic is encompassed by the present invention. Cancer vaccines typically include an antigen expressed on and isolated from a cancer cell or a cancer cell transfected with, and capable of expressing, a selected antigen. For example, any purified tumor antigen may be co-administered with an mTOR inhibitor such as RAD001 as described above for pathogenic vaccines. Identification of relevant cancer antigens will permit the development of such vaccines. Alternatively, other cancer therapeutics are designed using an antigen normally not expressed on a cancer cell. For example, a selected antigen may be transfected into the cancer cell and the transfected cell itself, expressing the antigen, is used as the vaccine or therapeutic.

The ability of an mTOR inhibitor to provide an adjuvant effect in a vaccine or to enhance an immune response to an antigen, such as a vaccine antigen (e.g., influenza) can be measured using methods well known in the art, such as, but not limited to an ELISA assay and a hemagglutination inhibition assay (See, e.g., Lee et al. Pediatr Infect Dis J. 2004 September; 23(9):852-6). Typically, the enhancement of an immune response to an antigen by an mTOR inhibitor can be determined by measuring titers of antibodies against the antigen in the subject, wherein an increase in the titer of antibodies directed against the particular antigen is indicative of the mTOR inhibitor having enhanced the immune response to the antigen.

When used as a vaccine adjuvant for a selected antigen, or when used according to the methods described herein, an mTOR inhibitor may be admixed as part of the antigen-containing composition itself. Such a composition is desirably a vaccine composition which contains a suitable carrier and, optionally, other desired components. Selection of appropriate carriers, e.g., phosphate buffered saline and the like, are well within the skill of those in the art. Similarly, one skilled in the art may readily select appropriate stabilizers, preservatives, and the like for inclusion in the composition. Any route of administration known in the art may be employed for the administration of an antigen or vaccine, e.g., subcutaneous, intraperitoneal, oral, intramuscular, intranasal and the like.

Alternatively, the immunostimulatory effect of an mTOR inhibitor may be obtained by administering the mTOR inhibitor separately from the vaccine composition. When separately administered, the mTOR inhibitor can be administered in a formulation as described hereinabove. The mTOR inhibitor may be administered contemporaneously with the vaccine composition, either simultaneously therewith, or before or after the vaccine antigen administration. If the mTOR inhibitor is administered before the vaccine composition, it is desirable to administer it one or more days before the vaccine. In one aspect, the mTOR inhibitor can be administered for a period of time prior to administration of the antigen. For example, the mTOR inhibitor can be administered for 1-7 days prior to administration of the vaccine, one week, two weeks, three weeks, four weeks, five weeks, or six weeks or more prior to administration of the antigen. In one aspect, the antigen is administered immediately following administration of the mTOR inhibitor. In another aspect, there can be a period of time between administration of the mTOR inhibitor and administration of the antigen. For example, the antigen may be administered 1-7 days following administration of the mTOR inhibitor, or can be administered one week, two weeks, three weeks or more following administration of the mTOR inhibitor. In one aspect, the mTOR inhibitor is administered to a subject for six weeks, followed by a two week period in which the subject is given neither mTOR inhibitor or antigen, followed by administration of the antigen. When the mTOR inhibitor is administered as a separate component from the vaccine, it is can be administered by the same route of administration as the vaccine antigen, or it may be administered by a different route, or any other route as selected by a physician. In a further aspect of the foregoing dosing schedules, administration of the mTOR inhibitor can continue after administration of the antigen. For example, whether administered prior to, or at the same time as the antigen, the mTOR inhibitor can continue to be administered on a weekly or daily dosing schedule as described herein for 1, 2, 3, 4, 5, 6, or 7 or more days following administration of the antigen. The mTOR inhibitor can continue to be administered for 1, 2, 3, 4, 5, or 6 weeks or more following administration of the antigen.

Other Methods Utilizing mTOR Inhibitors

In one aspect, the present invention relates to the use of low doses of an mTOR inhibitor in a method of enhancing an immune response to an antigen in a subject. In one aspect, the immune response to the antigen is enhanced by 1.2 fold when antigen exposure is combined with a low dose of an mTOR inhibitor. In a further aspect, the immune response to the antigen is enhanced by 0.5, 0.6, 0.7, 0.8, 0.9, 1.0, 1.1, 1.2, 1.3, 1.4, or 1.5 or greater when antigen exposure is combined with a low, immune enhancing, dose of an mTOR inhibitor as described herein. In a further aspect the mTOR inhibitor is an mTOR inhibitor described herein, e.g., RAD001, and is administered at a dose described herein, e.g., a dose of 0.005-1.5 mg daily, 0.01-1 mg daily, 0.01-0.7 mg daily, 0.01-0.5 mg daily, or 0.1-0.5 mg daily or 0.1-20 mg weekly, 0.5-15 mg weekly, 1-10 mg weekly, or 3-7 mg weekly. In one aspect, the mTOR inhibitor RAD001 is administered at a dose of 0.5 mg daily or 5 mg weekly. In each of the foregoing aspects, an mTOR inhibitor other than RAD001 can be administered at a bioequivalent dose.

In a further aspect, the invention relates to methods for enhancing the immune response to an antigen by administering an amount of an mTOR inhibitor sufficient to inhibit P70 S6 kinase by an amount described herein, e.g., by no greater than 80%. In a further aspect, the mTOR inhibitor is sufficient to inhibit P70 S6 kinase by no greater than 38%. In one aspect, the mTOR inhibitor is RAD001, rapamycin, a rapalog, or other mTOR inhibitor known in the art, such as Ridaforolimus, emsirolimus. In a further aspect the mTOR inhibitor may be a combination of two or more mTOR inhibitors. The method includes the steps of administering to a subject an antigen, such as, for example, a vaccine (e.g., influenza vaccine) and an mTOR inhibitor such as RAD001.

In one aspect, the antigen is a vaccine antigen, and can include, for example, influenza, pneumococcus, HIV, or other vaccine antigens. In particular, the vaccine antigen can be an influenza antigen such as H1N1, H2N3, and B influenza subtypes.

The present method of enhancing an immune response to an antigen encompasses a method in which the immune response to an antigen in a subject is increased. That is, where as a result of the inclusion of an mTOR inhibitor with administration of the antigen, there is an increase in protective immunity following exposure to the antigen, where protective immunity refers to the presence of sufficient antibody titers to protect against subsequent infection by the same antigen. In addition, an enhanced immune response to an antigen in response to treatment with an mTOR inhibitor can mean that in a population, there is an increase in the percentage of individuals that have protective immunity after exposure to an antigen such as a vaccine.

In one aspect, an indicator of a suppressed or impaired immune function/response is a reduced number of lymphocytes or reduced lymphocyte function, such as a reduced response to mitogenic stimulation. A human immune system can also be considered to be impaired when (1) the ratio of Th/Ts is less than about 1.0, (2) when the stimulation index to ConA is approximately 50% less than "normal" or (2) when the stimulation index to PHA is approximately 50% less than "normal" (See, e.g., EP0507872). A human immune system can also be considered impaired when antigen presentation and/or lymphocyte activation by macrophages and dendritic cells is below what is seen in cells derived from a healthy person less than 40 years of age, when the response of lymphocytes to activating signals is less than what is seen in lymphoctyes derived from a healthy person less than 40 years of age, when the secretion of inflammatory cytokines is above what is seen in a healthy person less than 40 years of age, when lymphopoiesis by hematopoietic stem cells is below that of hematopoietic stem cells from a person less than 40 years of age, or when the percentage of PD1+CD4+ and/or CD8+ T cells is above the percentage of PD1+CD4+ and/or CD8+ T cells in a person less than 40 years of age.

An impaired human immune response is frequently observed as a secondary effect of such conditions as trauma, for example, from an accident or from undergoing a major surgical procedure, from a debilitating disease, such as cancer or infection with the HIV virus (AIDS), or from malnutrition or old age. As a result of an impaired immune response, patients are unable to respond to and eliminate infectious agents, such as bacteria, viruses, and fungi, from their bodies.

In one aspect the method of enhancing an immune response in a subject also includes the step of first identifying a subject with an impaired immune response. A subject with an impaired immune response refers to a subject that is predicted not to get protective antibody titer levels following prophylactic vaccination, or in which a subject does not have a decrease in disease burden after therapeutic vaccination. Methods for determining antibody titers following vaccination and/or measuring disease burden are well known in the art and may be routinely performed by a physician or other medical professional.

For example, titer of an anti-influenza virus antibody can be measured by hemagglutination inhibition (HI) assay. The HI assay can be performed as described in Kendal, A P et al. (1982) *Concenpts and procedures for laboratory-based influenza surveillance*. Atlanta: Centers for Disease Control and Prevention B17-B35 and below. A constant amount of hemagglutinating antigen (HA) is added to each well of a microtiter plate. A test sample, e.g., serum of a patient, is added to the first well and serially diluted, e.g., two-fold, to desired dilution or number of wells. RBCs are added to each well. The plate is incubated for an amount of time sufficient for hemagglutination to occur, e.g., 1 hour. The plate is then observed for wells with agglutinated RBCs (indicating that there is insufficient antibody present to prevent hemagglutination) or unagglutinated RBCs (indicating that there is sufficient antibody present to prevent hemagglutination). The highest dilution of test sample required to prevent hemagglutination indicates the HI titer.

A subject can also be said to have an impaired immune response if the subject is a member of a population known to have decreased immune function such as the elderly, subjects undergoing immunosuppressive or chemotherapy treatment, asplenic subjects, immunocompromised subjects, or subjects having HIV/AIDS. That is, a subject can be predicted to have an impaired immune response based on their inclusion in a class of subjects typically associated with impaired immune function. Such individuals may be deemed to have impaired immune response without specific testing, or following confirmation of an impaired immune response using methods routine in the art. In addition a subject may be deemed to have an impaired immune response if that subject has a history of decreased immune function, such as a history of an inability to establish protective immunity after vaccination or exposure to an antigen.

Once a subject is identified as having an impaired immune response, the subject can be treated with an mTOR inhibitor in the context of vaccination and/or exposure to antigen as described herein.

In addition, in a further aspect, the invention relates to methods for treating immunosenescence in a subject by administering to the subject an amount of an mTOR inhibitor effective to increase the immune response to an antigen (e.g., a vaccine antigen) so that protective antibody titers or T cell response to the antigen are achieved. In one aspect, the invention provides a method for treating immunosenescence in a subject by administering low doses of an mTOR inhibitor such as RAD001. The mTOR inhibitor RAD001 can administered at a dose described herein, e.g., a dose of about 0.005-1.5 mg daily, about 0.01-1 mg daily, about 0.01-0.7 mg daily, about 0.01-0.5 mg daily, or about 0.1-0.5 mg daily or about 0.1-20 mg weekly, about 0.5-15 mg weekly, about 1-10 mg weekly, or about 3-7 mg weekly. In one aspect, RAD001 is administered at a dose of about 0.5 mg daily or 5 mg weekly. In a further embodiment of the foregoing, the mTOR inhibitor can be an inhibitor other than RAD001 administered at a dose that is bioequivalent to the doses of RAD001 indicated above. In a further aspect, the invention relates to methods of treating immunosenescence in a subject by administering an amount of an mTOR inhibitor sufficient to inhibit P70 S6 kinase by no greater than 80%. In a further aspect, the mTOR inhibitor is sufficient to inhibit P70 S6 kinase by no greater than 38%. In one aspect, the mTOR inhibitor is RAD001, rapamycin, a rapalog, or other mTOR inhibitor known in the art. In a further aspect the mTOR inhibitor may be a combination of two or more mTOR inhibitors.

Immunosenescence refers to a decrease in immune function associated with age resulting in impaired response to vaccination and infectious pathogens. It involves both the host's capacity to respond to infections and the development of long-term immune memory, especially by vaccination. This age-associated immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria. Immunosenescence is a multifactorial condition leading to many pathologically significant health problems in the aged population. Age-dependent biological changes such as depletion of hematopoietic stem cells, decline in the total number of phagocytes and NK cells and a decline in humoral immunity contribute to the onset of immunosenescence and may be used as indicators of the onset or presence of immunosenescence. In one aspect, immunosenescence can be measured in an individual by measuring telomere length in immune cells (See, e.g., U.S. Pat. No. 5,741,677). Immunosenescence can also be measured in an individual by measuring the number of naïve CD4 and/or CD8 T cells, by measuring T cell repertoire, by measuring percentage of PD1+CD4 and CD8 T cells, or by measuring the response to vaccination in a subject over the age of 65. In a further aspect, the invention relates to methods for the treatment of an age related condition in a subject by administering to the subject the mTOR inhibitor RAD001 at a dose of about 0.005-1.5 mg daily, about 0.01-1 mg daily, about 0.01-0.7 mg daily, about 0.01-0.5 mg daily, or about 0.1-0.5 mg daily or about 0.1-20 mg weekly, about 0.5-15 mg weekly, about 1-10 mg weekly, or about 3-7 mg weekly. In one aspect, the mTOR inhibitor is administered at a dose of about 0.5 mg daily or about 5 mg weekly. In one aspect the mTOR inhibitor can be an mTOR inhibitor other than RAD001 administered at a dose that is bioequivalent to the specified doses of RAD001. In a further aspect, the invention relates to a method of treating an age related condition in a subject by administering an amount of an mTOR inhibitor sufficient to inhibit P70 S6 kinase by no greater than 80%. In a further aspect, the mTOR inhibitor is sufficient to inhibit P70 S6 kinase by no greater than 38%. In one aspect, the mTOR inhibitor is RAD001, rapamycin, a rapalog, or other mTOR inhibitor known in the art. In a further aspect the mTOR inhibitor may be a combination of two or more mTOR inhibitors.

An age-related condition can be any disease, disorder, or pathology whose incidence in a population or severity in an individual correlates with the progression of age. More specifically, an age-related condition is a disease, disorder, or pathology whose incidence is at least 1.5 fold higher among human individuals greater than 60 years of age relative to human individuals between the ages of 30-40 and in a selected population of greater than 100,000 individuals. Age-related conditions relevant to the present invention include, but are not limited to sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy andsystolic and diastolic dysfunction, immunosenescence, cancer, and diabetes.

The treatment of an age-related condition using the mTOR inhibitors described herein may be complete, e.g., the total absence of an age-related condition or metabolic disorder. The prevention may also be partial, such that the likelihood of the occurrence of the age-related condition or metabolic disorder in a subject is less likely to occur than had the subject not received an mTOR inhibitor of the present disclosure. Methods for measuring the effectiveness of an mTOR inhibitor in the treatment of an age-related condition described herein are known in the art and examples of such methods may be found in U.S. Pat. No. 8,420,088.

Combination Treatments

In some embodiments, it may be advantageous to administer an mTOR inhibitor, e.g., an mTOR inhibitor described herein, at a low, immune enhancing, dose with one or more therapeutic agents (pharmaceutical combinations). For example, synergistic effects can occur with other immunostimulatory, anti-infective, anti-tumor or anti-proliferative agents, for example, mitotic inhibitors, alkylating agents, anti-metabolites, intercalating antibiotics, growth factor inhibitors (e.g., trastuzumab, panitumumab, cetuximab, gefitinib, erlotinib, lapatinib, sorafenib, etc.), cell cycle inhibitors, enzymes, topoisomerase inhibitors, biological response modifiers, antibodies, cytotoxics, bronchodilators, anti-hormones, anti-androgens, an anti-angiogenesis agent, kinase inhibitor, pan kinase inhibitor or growth factor inhibitor. Other suitable therapeutic agents are listed in the Physicians' Desk Reference. Where the compounds of the invention are administered in conjunction with other therapies, dosages of the co-administered compounds will of course vary depending on the type of co-drug employed, on the specific drug employed, on the condition being treated and so forth.

Accordingly, an mTOR inhibitor, e.g., an mTOR inhibitor described herein, may be used at low, immune enhancing, dose in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

An mTOR inhibitor, e.g., an mTOR inhibitor described herein, at low, immune enhancing, dose, and the at least one additional therapeutic agent can be administered simultaneously, in the same or in separate compositions, or sequentially. For sequential administration, the mTOR inhibitor can be administered first, and the additional agent can be administered second, or the order of administration can be reversed. In some embodiments, the mTOR inhibitor is administered as a pretreatment, e.g., 1 week, 2 weeks, 3 weeks, 4 weeks, 5 weeks, 6 weeks, 7 weeks, 8 weeks, 9 weeks, 10 weeks, 11 weeks, 12 weeks or more, before treatment with the at least one additional therapeutic agent.

In some embodiments, an mTOR inhibitor, e.g., an mTOR inhibitor described herein, is administered at low, immune enhancing, dose to a subject who has cancer, e.g., a cancer described herein. The subject may receive treatment with an additional therapeutic agent, such as an approved drug for that type of cancer, in combination with the mTOR inhibitor. For example, Table 1 below provides a list of various cancers and their approved treatments.

TABLE 1

| Cancers and Approved Treatment(s) | |
|---|---|
| Cancer | Treatment(s) |
| Acute Lymphoblastic Leukemia | Abitrexate (Methotrexate); Adriamycin PFS (Doxorubicin Hydrochloride); Adriamycin RDF (Doxorubicin Hydrochloride); Arranon (Nelarabine); Asparaginase *Erwinia chrysanthemi*; Cerubidine (Daunorubicin Hydrochloride); Clafen (Cyclophosphamide); Clofarabine; Clofarex (Clofarabine); Clolar (Clofarabine); Cyclophosphamide; Cytarabine; Cytosar-U (Cytarabine); Cytoxan (Cyclophosphamide); Dasatinib; Daunorubicin Hydrochloride; Doxorubicin Hydrochloride; Erwinaze (Asparaginase *Erwinia Chrysanthemi*); Folex (Methotrexate); Folex PFS (Methotrexate); Gleevec (Imatinib Mesylate); Iclusig (Ponatinib Hydrochloride); Imatinib Mesylate; Marqibo (Vincristine Sulfate Liposome); Mercaptopurine; |

TABLE 1-continued

Cancers and Approved Treatment(s)

| Cancer | Treatment(s) |
|---|---|
| | Methotrexate; Methotrexate LPF (Methorexate); Mexate (Methotrexate); Mexate-AQ (Methotrexate); Nelarabine; Neosar (Cyclophosphamide); Oncaspar (Pegaspargase); Pegaspargase; Purinethol (Mercaptopurine); Purixan (Mercaptopurine); Rubidomycin (Daunorubicin Hydrochloride); Sprycel (Dasatinib); Tarabine PFS (Cytarabine); Vincasar PFS (Vincristine Sulfate); Vincristine Sulfate; or Vincristine Sulfate Liposome. DRUG COMBINATIONS hyper-CVAD: Cyclophosphamide; Vincristine Sulfate; Doxorubicin Hydrochloride (Adriamycin); Dexamethasone. |
| Acute Myeloid Leukemia | Adriamycin PFS (Doxorubicin Hydrochloride); Adriamycin RDF (Doxorubicin Hydrochloride); Arsenic Trioxide; Cerubidine (Daunorubicin Hydrochloride); Clafen (Cyclophosphamide); Cyclophosphamide; Cytarabine; Cytosar-U (Cytarabine); Cytoxan (Cyclophosphamide); Daunorubicin Hydrochloride; Doxorubicin Hydrochloride; Neosar (Cyclophosphamide); Rubidomycin (Daunorubicin Hydrochloride); Tarabine PFS (Cytarabine); Trisenox (Arsenic Trioxide); Vincasar PFS (Vincristine Sulfate); or Vincristine Sulfate. DRUG COMBINATIONS ADE: Cytarabine; Daunorubicin Hydrochloride; and Etoposide. |
| AIDS-Related Kaposi Sarcoma | Dox-SL (Doxorubicin Hydrochloride Liposome); Doxil (Doxorubicin Hydrochloride Liposome); Doxorubicin Hydrochloride Liposome; Evacet (Doxorubicin Hydrochloride Liposome); Intron A (Recombinant Interferon Alfa-2b); LipoDox (Doxorubicin Hydrochloride Liposome); Paclitaxel; Recombinant Interferon Alfa-2b; Taxol (Paclitaxel); Velban (Vinblastine Sulfate); Velsar (Vinblastine Sulfate); or Vinblastine Sulfate. |
| Basal Cell Carcinoma | Adrucil (Fluorouracil); Aldara (Imiquimod); Efudex (Fluorouracil); Erivedge (Vismodegib); Fluoroplex (Fluorouracil); Fluorouracil; Imiquimod; or Vismodegib. |
| Bladder Cancer | Adriamycin PFS (Doxorubicin Hydrochloride); Adriamycin RDF (Doxorubicin Hydrochloride); Cisplatin; Doxorubicin Hydrochloride; Platinol (Cisplatin); or Platinol-AQ (Cisplatin). |
| Bone Cancer | Abitrexate (Methotrexate); Adriamycin PFS (Doxorubicin Hydrochloride); Adriamycin RDF (Doxorubicin Hydrochloride); Doxorubicin Hydrochloride; Folex (Methotrexate); Folex PFS (Methotrexate); Methotrexate; Methotrexate LPF (Methotrexate); Mexate (Methotrexate); or Mexate-AQ (Methotrexate). |
| Brain Tumor | Afinitor (Everolimus); Afinitor Disperz (Everolimus); Avastin (Bevacizumab); Bevacizumab; CeeNu (Lomustine); Everolimus; Lomustine; Methazolastone (Temozolomide); Temodar (Temozolomide); or Temozolomide. |
| Breast Cancer | Abitrexate (Methotrexate); Abraxane (Paclitaxel Albumin-stabilized Nanoparticle Formulation); Ado-Trastuzumab Emtansine; Adriamycin PFS (Doxorubicin Hydrochloride); Adriamycin RDF (Doxorubicin Hydrochloride); Adrucil (Fluorouracil); Afinitor (Everolimus); Anastrozole; Aredia (Pamidronate Disodium); Arimidex (Anastrozole); Aromasin (Exemestane); Capecitabine; Clafen (Cyclophosphamide); Cyclophosphamide; Cytoxan (Cyclophosphamide); Docetaxel; Doxorubicin Hydrochloride; Efudex (Fluorouracil); Ellence (Epirubicin Hydrochloride); Epirubicin Hydrochloride; Everolimus; Exemestane; Fareston (Toremifene); Faslodex (Fulvestrant); Femara (Letrozole); Fluoroplex (Fluorouracil); Fluorouracil; Folex (Methotrexate); Folex PFS (Methotrexate); Fulvestrant; Gemcitabine Hydrochloride; Gemzar (Gemcitabine Hydrochloride); Goserelin Acetate; Herceptin (Trastuzumab); Ixabepilone; Ixempra (Ixabepilone); Kadcyla (Ado-Trastuzumab Emtansine); Lapatinib Ditosylate; Letrozole; Megace (Megestrol Acetate); Megestrol Acetate; Methotrexate; Methotrexate LPF (Methotrexate); Mexate (Methotrexate); Mexate-AQ (Methotrexate); Neosar (Cyclophosphamide); Nolvadex (Tamoxifen Citrate); Novaldex (Tamoxifen Citrate); Paclitaxel; Paclitaxel Albumin-stabilized Nanoparticle Formulation; Pamidronate Disodium; Perjeta (Pertuzumab); Pertuzumab; Tamoxifen Citrate; Taxol (Paclitaxel); Taxotere (Docetaxel); Trastuzumab; Toremifene; Tykerb (Lapatinib Ditosylate); Xeloda (Capecitabine); or Zoladex (Goserelin Acetate). DRUG COMBINATIONS |

TABLE 1-continued

Cancers and Approved Treatment(s)

| Cancer | Treatment(s) |
|---|---|
| | AC: Doxorubicin Hydrochloride (Adriamycin) and Cyclophosphamide.<br>AC-T: Doxorubicin Hydrochloride (Adriamycin); Cyclophosphamide; and Paclitaxel (Taxol).<br>CAF: Cyclophosphamide; Doxorubicin Hydrochloride (Adriamycin); and Fluorouracil.<br>CMF: Cyclophosphamide; Methotrexate; and Fluorouracil.<br>FEC: Fluorouracil; Epirubicin Hydrochloride; and Cyclophosphamide.<br>TAC: Docetaxel (Taxotere); Doxorubicin Hydrochloride (Adriamycin); and Cyclophosphamide. |
| Cervical Cancer | Blenoxane (Bleomycin); Bleomycin; Cisplatin; Hycamtin (Topotecan Hydrochloride); Platinol (Cisplatin); Platinol-AQ (Cisplatin); or Topotecan Hydrochloride.<br>DRUG COMBINATIONS<br>Gemcitabine-Cisplatin: Gemcitabine Hydrochloride and Cisplatin. |
| Chronic Lymphocytic Leukemia | Alemtuzumab; Ambochlorin (Chlorambucil); Amboclorin (Chlorambucil); Arzerra (Ofatumumab); Bendamustine Hydrochloride; Campath (Alemtuzumab); Chlorambucil; Clafen (Cyclophosphamide); Cyclophosphamide; Cytoxan (Cyclophosphamide); Fludara (Fludarabine Phosphate); Fludarabine Phosphate; Gazyva (Obinutuzumab); Ibrutinib; Imbruvica (Ibrutinib); Leukeran (Chlorambucil); Linfolizin (Chlorambucil); Neosar (Cyclophosphamide); Obinutuzumab; Ofatumumab; or Treanda (Bendamustine Hydrochloride).<br>DRUG COMBINATIONS<br>CHLORAMBUCIL-PREDNISONE: Chlorambucil and Prednisone.<br>CVP: Cyclophosphamide; Vincristine Sulfate; and Prednisone. |
| Chronic Myelogenous Leukemia | Bosulif (Bosutinib); Bosutinib; Busulfan; Busulfex (Busulfan); Clafen; Cyclophosphamide; Cyclophosphamide; Cytarabine; Cytosar-U (Cytarabine); Cytoxan (Cyclophosphamide); Dasatinib; Gleevec (Imatinib Mesylate); Iclusig (Ponatinib Hydrochloride); Imatinib Mesylate; Myleran (Busulfan); Neosar (Cyclophosphamide); Nilotinib; Omacetaxine Mepesuccinate; Ponatinib Hydrochloride; Sprycel (Dasatinib); Synribo (Omacetaxine Mepesuccinate); Tarabine PFS (Cytarabine); or Tasigna (Nilotinib). |
| Colon Cancer | Adrucil (Fluorouracil); Avastin (Bevacizumab); Bevacizumab; Camptosar (Irinotecan Hydrochloride); Capecitabine; Cetuximab; Efudex (Fluorouracil); Eloxatin (Oxaliplatin); Erbitux (Cetuximab); Fluoroplex (Fluorouracil); Fluorouracil; Irinotecan Hydrochloride; Leucovorin Calcium; Oxaliplatin; Panitumumab; Regorafenib; Stivarga (Regorafenib); Vectibix (Panitumumab); Wellcovorin (Leucovorin Calcium); Xeloda (Capecitabine); Zaltrap (Ziv-Aflibercept); or Ziv-Aflibercept.<br>DRUG COMBINATIONS<br>CAPOX: Capecitabine and Oxaliplatin.<br>FOLFIRI: Leucovorin Calcium (Folinic Acid); Fluorouracil; and Irinotecan Hydrochloride.<br>FOLFIRI-BEVACIZUMAB: Leucovorin Calcium (Folinic Acid); Fluorouracil; Irinotecan Hydrochloride; and Bevacizumab.<br>FOLFIRI-CETUXIMAB: Leucovorin Calcium (Folinic Acid); Fluorouracil; Irinotecan Hydrochloride; and Cetuximab.<br>FOLFOX: Leucovorin Calcium (Folinic Acid); Fluorouracil; and Oxaliplatin.<br>XELOX: Capecitabine (Xeloda) and Oxaliplatin. |
| Endometrial Cancer | Megace (Megestrol Acetate) or Megestrol Acetate. |
| Gastric (Stomach) Cancer | Adriamycin PFS (Doxorubicin Hydrochloride); Adriamycin RDF (Doxorubicin Hydrochloride); Adrucil (Fluorouracil); Cyramza (Ramucirumab); Docetaxel; Doxorubicin Hydrochloride; Efudex (Fluorouracil); Fluoroplex (Fluorouracil); Fluorouracil; Herceptin (Trastuzumab); Mitomycin C; Mitozytrex (Mitomycin C); Mutamycin (Mitomycin C); Ramucirumab; Taxotere (Docetaxel); or Trastuzumab. |
| Gastrointestinal stromal tumors | Gleevec (Imatinib Mesylate); Imatinib Mesylate; Regorafenib; Stivarga (Regorafenib); Sunitinib Malate; Sutent (Sunitinib Malate) |
| Head and neck cancer | Abitrexate (Methotrexate); Adrucil (Fluorouracil); Blenoxane (Bleomycin); Bleomycin; Cetuximab; Cisplatin; Docetaxel; Efudex (Fluorouracil); Erbitux (Cetuximab); Fluoroplex (Fluorouracil); Fluorouracil; Folex (Methotrexate); Folex PFS |

TABLE 1-continued

Cancers and Approved Treatment(s)

| Cancer | Treatment(s) |
|---|---|
| | (Methotrexate); Methotrexate; Methotrexate LPF (Methotrexate); Mexate (Methotrexate); Mexate-AQ (Methotrexate); Platinol (Cisplatin); Platinol-AQ (Cisplatin); or Taxotere (Docetaxel). |
| Hodkin Lymphoma | Adcetris (Brentuximab Vedotin); Adriamycin PFS (Doxorubicin Hydrochloride); Adriamycin RDF (Doxorubicin Hydrochloride); Ambochlorin (Chlorambucil); Amboclorin (Chlorambucil); Blenoxane (Bleomycin); Bleomycin; Brentuximab Vedotin; Chlorambucil; Clafen (Cyclophosphamide); Cyclophosphamide; Cytoxan (Cyclophosphamide); Dacarbazine; Doxorubicin Hydrochloride; DTIC-Dome (Dacarbazine); Leukeran (Chlorambucil); Linfolizin (Chlorambucil); Lomustine; Matulane (Procarbazine Hydrochloride); Neosar (Cyclophosphamide); Procarbazine Hydrochloride; Velban (Vinblastine Sulfate); Velsar (Vinblastine Sulfate); Vinblastine Sulfate; Vincasar PFS (Vincristine Sulfate); or Vincristine Sulfate.<br>DRUG COMBINATIONS:<br>ABVD: Doxorubicin Hydrochloride (Adriamycin); Bleomycin; Vinblastine Sulfate; and Dacarbazine.<br>ABVE: Doxorubicin Hydrochloride (Adriamycin); Bleomycin; Vinblastine Sulfate; and Etoposide.<br>ABVE-PC: Doxorubicin Hydrochloride (Adriamycin); Bleomycin; Vinblastine Sulfate; Etoposide; Prednisone; and Cyclophosphamide.<br>BEACOPP: Bleomycin; Etoposide; Doxorubicin Hydrochloride (Adriamycin); Cyclophosphamide; Vincristine Sulfate (Oncovin); Procarbazine Hydrochloride; and Prednisone.<br>COPP: Cyclophosphamide; Vincristine Sulfate (Oncovin); Procarbazine Hydrochloride; and Prednisone.<br>COPP-ABV: Cyclophosphamide; Vincristine Sulfate (Oncovin); Procarbazine Hydrochloride; Prednisone; Doxorubicin Hydrochloride (Adriamycin); Bleomycin; and Vinblastine Sulfate.<br>ICE: Ifosfamide; Carboplatin; and Etoposide.<br>MOPP: Mechlorethamine Hydrochloride; Vincristine Sulfate (Oncovin); Procarbazine Hydrochloride; and Prednisone.<br>OEPA: Vincristine Sulfate (Oncovin); Etoposide; Prednisone; and Doxorubicin Hydrochloride (Adriamycin).<br>OPPA: Vincristine Sulfate (Oncovin); Procarbazine Hydrochloride; Prednisone; and Doxorubicin Hydrochloride (Adriamycin).<br>STANFORD V: Mechlorethamine Hydrochloride; Doxorubicin Hydrochloride; Vinblastine Sulfate; Vincristine Sulfate; Bleomycin; Etoposide; and Prednisone.<br>VAMP: Vincristine Sulfate; Doxorubicin Hydrochloride (Adriamycin); and Methotrexate; and Prednisone. |
| Kidney (Renal Cell) Cancer | Afinitor (Everolimus); Aldesleukin; Avastin (Bevacizumab); Axitinib; Bevacizumab; Everolimus; Inlyta (Axitinib); Nexavar (Sorafenib Tosylate); Pazopanib Hydrochloride; Proleukin (Aldesleukin); Sorafenib Tosylate; Sunitinib Malate; Sutent (Sunitinib Malate); Temsirolimus; Torisel (Temsirolimus); or Votrient (Pazopanib Hydrochloride). |
| Liver Cancer | Nexavar (Sorafenib Tosylate) or Sorafenib Tosylate. |
| Melanoma | Aldesleukin; Dabrafenib; Dacarbazine; DTIC-Dome (Dacarbazine); Intron A (Recombinant Interferon Alfa-2b); Ipilimumab; Mekinist (Trametinib); Peginterferon Alfa-2b; PEG-Intron (Peginterferon Alfa-2b); Proleukin (Aldesleukin); Recombinant Interferon Alfa-2b; Sylatron (Peginterferon Alfa-2b); Tafinlar (Dabrafenib); Trametinib; Vemurafenib; Yervoy (Ipilimumab); or Zelboraf (Vemurafenib). |
| Malignant Mesothelioma | Alimta (Pemetrexed Disodium); Cisplatin; Pemetrexed Disodium; Platinol (Cisplatin); or Platinol-AQ (Cisplatin). |
| Multiple myeloma | Aredia (Pamidronate Disodium); Bortezomib; Carfilzomib; Clafen (Cyclophosphamide); Cyclophosphamide; Cytoxan (Cyclophosphamide); Doxil (Doxorubicin Hydrochloride Liposome); Doxorubicin Hydrochloride Liposome; Dox-SL (Doxorubicin Hydrochloride Liposome); Evacet (Doxorubicin Hydrochloride Liposome); Kyprolis (Carfilzomib); Lenalidomide; LipoDox (Doxorubicin Hydrochloride Liposome); Mozobil (Plerixafor); Neosar (Cyclophosphamide); Pamidronate Disodium; Plerixafor; Pomalidomide (Pomalyst); Pomalyst; Revlimid (Lenalidomide); Synovir (Thalidomide); Thalidomide; |

TABLE 1-continued

Cancers and Approved Treatment(s)

| Cancer | Treatment(s) |
|---|---|
| | Thalomid (Thalidomide); Velcade (Bortezomib); Zoledronic Acid; Zometa (Zoledronic Acid) |
| Myeloproliferative Disorders | Adriamycin PFS (Doxorubicin Hydrochloride); Adriamycin RDF (Doxorubicin Hydrochloride); Arsenic Trioxide; Azacitidine; Cerubidine (Daunorubicin Hydrochloride); Clafen (Cyclophosphamide); Cyclophosphamide; Cytarabine; Cytosar-U (Cytarabine); Cytarabine; Cytoxan (Cyclophosphamide); Dacogen (Decitabine); Dasatinib; Daunorubicin Hydrochloride; Decitabine; Doxorubicin Hydrochloride; Gleevec (Imatinib Mesylate); Imatinib Mesylate; Jakafi (Ruxolitinib Phosphate); Lenalidomide; Mylosar (Azacitidine); Neosar (Cyclophosphamide); Nilotinib; Revlimid (Lenalidomide); Rubidomycin (Daunorubicin Hydrochloride); Ruxolitinib Phosphate; Sprycel (Dasatinib); Tarabine PFS (Cytarabine); Tasigna (Nilotinib); Trisenox (Arsenic Trioxide); Vidaza (Azacitidine); Vincasar PFS (Vincristine Sulfate); or Vincristine Sulfate.<br>DRUG COMBINATIONS<br>ADE: Cytarabine; Daunorubicin Hydrochloride; and Etoposide. |
| Neuroblastoma | Adriamycin PFS (Doxorubicin Hydrochloride); Adriamycin RDF (Doxorubicin Hydrochloride); Clafen (Cyclophosphamide); Cyclophosphamide; Cytoxan (Cyclophosphamide); Doxorubicin Hydrochloride; Neosar (Cyclophosphamide); Vincasar PFS (Vincristine Sulfate); or Vincristine Sulfate. |
| Non-Hodkin Lymphoma | Abitrexate (Methotrexate); Adcetris (Brentuximab Vedotin); Adriamycin PFS (Doxorubicin Hydrochloride); Adriamycin RDF (Doxorubicin Hydrochloride); Ambochlorin (Chlorambucil); Amboclorin (Chlorambucil); Arranon (Nelarabine); Bendamustine Hydrochloride; Bexxar (Tositumomab and Iodine I 131 Tositumomab); Blenoxane (Bleomycin); Bleomycin; Bortezomib; Brentuximab Vedotin; Chlorambucil; Clafen (Cyclophosphamide); Cyclophosphamide; Cytoxan (Cyclophosphamide); Denileukin Diftitox; DepoCyt (Liposomal Cytarabine); Doxorubicin Hydrochloride; DTIC-Dome (Dacarbazine); Folex (Methotrexate); Folex PFS (Methotrexate); Folotyn (Pralatrexate); Ibritumomab Tiuxetan; Ibrutinib; Imbruvica (Ibrutinib); Intron A (Recombinant Interferon Alfa-2b); Istodax (Romidepsin); Lenalidomide; Leukeran (Chlorambucil); Linfolizin (Chlorambucil); Liposomal Cytarabine; Matulane (Procarbazine Hydrochloride); Methotrexate; Methotrexate LPF (Methotrexate); Mexate (Methotrexate); Mexate-AQ (Methotrexate); Mozobil (Plerixafor); Nelarabine; Neosar (Cyclophosphamide); Ontak (Denileukin Diftitox); Plerixafor; Pralatrexate; Recombinant Interferon Alfa-2b; Revlimid (Lenalidomide); Rituxan (Rituximab); Rituximab; Romidepsin; Tositumomab and Iodine I 131 Tositumomab; Treanda (Bendamustine Hydrochloride); Velban (Vinblastine Sulfate); Velcade (Bortezomib); Velsar (Vinblastine Sulfate); Vinblastine Sulfate; Vincasar PFS (Vincristine Sulfate); Vincristine Sulfate; Vorinostat; Zevalin (Ibritumomab Tiuxetan); or Zolinza (Vorinostat).<br>DRUG COMBINATIONS<br>CHOP: Cyclophosphamide; Doxorubicin Hydrochloride (Hydroxydaunomycin); Vincristine Sulfate (Oncovin); and Prednisone.<br>COPP: Cyclophosphamide; Vincristine Sulfate (Oncovin); Procarbazine Hydrochloride; and Prednisone.<br>CVP: Cyclophosphamide; Vincristine Sulfate; and Prednisone.<br>EPOCH: Etoposide; Prednisone; Vincristine Sulfate (Oncovin); Cyclophosphamide; and Doxorubicin Hydrochloride (Hydroxydaunomycin).<br>Hyper-CVAD: Cyclophosphamide; Vincristine Sulfate; Doxorubicin Hydrochloride (Adriamycin); and Dexamethasone.<br>ICE: Ifosfamide; Carboplatin; and Etoposide.<br>R-CHOP: Rituximab; Cyclophosphamide; Doxorubicin Hydrochloride (Hydroxydaunomycin); Vincristine Sulfate (Oncovin); and Prednisone. |
| Non-Small Cell Lung Cancer | Abitrexate (Methotrexate); Abraxane (Paclitaxel Albumin-stabilized Nanoparticle Formulation); Afatinib Dimaleate; Alimta (Pemetrexed Disodium); Avastin (Bevacizumab); Bevacizumab; Carboplatin; Ceritinib; Cisplatin; Crizotinib; |

TABLE 1-continued

Cancers and Approved Treatment(s)

| Cancer | Treatment(s) |
|---|---|
| | Docetaxel; Erlotinib Hydrochloride; Folex (Methotrexate); Folex PFS (Methotrexate); Gefitinib; Gilotrif (Afatinib Dimaleate); Gemcitabine Hydrochloride; Gemzar (Gemcitabine Hydrochloride); Iressa (Gefitinib); Methotrexate; Methotrexate LPF (Methotrexate); Mexate (Methotrexate); Mexate-AQ (Methotrexate); Paclitaxel; Paclitaxel Albumin-stabilized Nanoparticle Formulation; Paraplat (Carboplatin); Paraplatin (Carboplatin); Pemetrexed Disodium; Platinol (Cisplatin); Platinol-AQ (Cisplatin); Tarceva (Erlotinib Hydrochloride); Taxol (Paclitaxel); Taxotere (Docetaxel); Xalkori (Crizotinib); or Zykadia (Ceritinib).<br>DRUG COMBINATIONS<br>CARBOPLATIN-TAXOL; Carboplatin and Paclitaxel (Taxol).<br>Gemcitabine-Cisplatin: Gemcitabine Hydrochloride and Cisplatin. |
| Ovarian Cancer | Adriamycin PFS (Doxorubicin Hydrochloride); Adriamycin RDF (Doxorubicin Hydrochloride); Carboplatin; Clafen (Cyclophosphamide); Cisplatin; Cyclophosphamide; Cytoxan (Cyclophosphamide); Doxorubicin Hydrochloride; Dox-SL (Doxorubicin Hydrochloride Liposome); DOXIL (Doxorubicin Hydrochloride Liposome); Doxorubicin Hydrochloride Liposome; Evacet (Doxorubicin Hydrochloride Liposome); Gemcitabine Hydrochloride; Gemzar (Gemcitabine Hydrochloride); Hycamtin (Topotecan Hydrochloride); LipoDox (Doxorubicin Hydrochloride Liposome); Neosar (Cyclophosphamide); Paclitaxel; Paraplat (Carboplatin); Paraplatin (Carboplatin); Platinol (Cisplatin); Platinol-AQ (Cisplatin); Taxol (Paclitaxel); or Topotecan Hydrochloride.<br>DRUG COMBINATIONS<br>BEP: Bleomycin; Etoposide; and Cisplatin (Platinol).<br>CARBOPLATIN-TAXOL: Carboplatin and Paclitaxel (Taxol).<br>Gemcitabine-Cisplatin: Gemcitabine Hydrochloride and Cisplatin. |
| Pancreatic cancer | Adrucil (Fluorouracil); Afinitor (Everolimus); Efudex (Fluorouracil); Erlotinib Hydrochloride; Everolimus; Fluoroplex (Fluorouracil); Fluorouracil; Gemcitabine Hydrochloride; Gemzar (Gemcitabine Hydrochloride); Mitomycin C; Mitozytrex (Mitomycin C); Mutamycin (Mitomycin C); Sunitinib Malate; Sutent (Sunitinib Malate); or Tarceva (Erlotinib Hydrochloride).<br>DRUG COMBINATIONS<br>GEMCITABINE-OXALIPLATIN: Gemcitabine Hydrochloride and Oxaliplatin. |
| Penile cancer | Blenoxane (Bleomycin); Bleomycin |
| Rectal Cancer | Adrucil (Fluorouracil); Avastin (Bevacizumab); Bevacizumab; Camptosar (Irinotecan Hydrochloride); Cetuximab; Efudex (Fluorouracil); Erbitux (Cetuximab); Fluoroplex (Fluorouracil); Fluorouracil; Irinotecan Hydrochloride; Panitumumab; Regorafenib; Stivarga (Regorafenib); Vectibix (Panitumumab); Zaltrap (Ziv-Aflibercept); or Ziv-Aflibercept.<br>DRUG COMBINATIONS<br>CAPOX: Capecitabine and Oxaliplatin.<br>FOLFIRI: Leucovorin Calcium (Folinic Acid); FluorouracilL; Irinotecan Hydrochloride.<br>FOLFIRI-BEVACIZUMAB: Leucovorin Calcium (Folinic Acid); Fluorouracil; Irinotecan Hydrochloride; and Bevacizumab.<br>FOLFIRI-CETUXIMAB: Leucovorin Calcium (Folinic Acid); Fluorouracil; Irinotecan Hydrochloride; and Cetuximab.<br>FOLFOX: Leucovorin Calcium (Folinic Acid); Fluorouracil; and Oxaliplatin.<br>XELOX: Capecitabine (Xeloda) and Oxaliplatin. |
| Renal Cell Carcinoma | Afinitor (Everolimus); Aldesleukin; Avastin (Bevacimub); Axitinib; Bevacizumab; Everolimus; Inlyta (Axitinib); Nexavar (Sorafenib Tosylate); Sunitinib Malate; Sutent (Sunitinib Malate); Temsirolimus; Torisel (Temsirolimus); Votrient (Pazopanib Hydrochloride) |
| Retinoblastoma | Clafen (Cyclophosphamide); Cyclophosphamide; Cytoxan (Cyclophosphamide); or Neosar (Cyclophosphamide). |
| Rhabdomyosarcoma | Cosmegen (Dactinomycin); Dactinomycin; Vincasar PFS (Vincristine Sulfate); or Vincristine Sulfate. |

TABLE 1-continued

Cancers and Approved Treatment(s)

| Cancer | Treatment(s) |
| --- | --- |
| Skin cancer (basal cell carcinoma) | Adrucil (Fluorouracil); Aldara (Imiquimod); Efudex (Fluorouracil); Erivedge (Vismodegib); Fluoroplex (Fluorouracil); Fluorouracil; Imiquimod; or Vismodegib. |
| Skin cancer (melanoma) | Aldesleukin; Dacarbazine; DTIC-Dome (Dacarbazine); Ipilimumab; Proleukin (Aldesleukin); Vemurafenib; Yervoy (Ipilimumab); or Zelboraf (Vemurafenib). |
| Small cell lung cancer | Abitrexate (Methotrexate); Etopophos (Etoposide Phosphate); Etoposide; Etoposide Phosphate; Folex (Methotrexate); Folex PFS (Methotrexate); Hycamtin (Topotecan Hydrochloride); Methotrexate; Methotrexate LPF (Methotrexate); Mexate (Methotrexate); Mexate-AQ (Methotrexate); Toposar (Etoposide); Topotecan Hydrochloride; or VePesid (Etoposide). |
| Soft tissue sarcoma | Adriamycin PFS (Doxorubicin Hydrochloride); Adriamycin RDF (Doxorubicin Hydrochloride); Cosmegen (Dactinomycin); Dactinomycin; orDoxorubicin Hydrochloride. |
| Testicular cancer | Blenoxane (Bleomycin); Bleomycin; Cisplatin; Cosmegen (Dactinomycin); Cyfos (Ifosfamide); Dactinomycin; Etopophos (Etoposide Phosphate); Etoposide; Etoposide Phosphate; Ifex (Ifosfamide); Ifosfamide; Ifosfamidum (Ifosfamide); Platinol (Cisplatin); Platinol-AQ (Cisplatin); Toposar (Etoposide;; Velban (Vinblastine Sulfate); Velsar (Vinblastine Sulfate); or VePesid (Etoposide); Vinblastine Sulfate. |
| Thyroid cancer | Adriamycin PFS (Doxorubicin Hydrochloride); Adriamycin RDF (Doxorubicin Hydrochloride); Cabozantinib-S-Malate; Caprelsa (Vandetanib); Cometriq (Cabozantinib-S-Malate); Doxorubicin Hydrochloride; Nexavar (Sorafenib Tosylate); or Sorafenib Tosylate; Vandetanib. |
| Vaginal cancer | Gardasil (Recombinant HPV Quadrivalent Vaccine); or Recombinant Human Papillomavirus (HPV) Quadrivalent Vaccine. |
| Vulvar cancer | Blenoxane (Bleomycin); Bleomycin; Gardasil (Recombinant HPV Quadrivalent Vaccine); or Recombinant Human Papillomavirus (HPV) Quadrivalent Vaccine. |
| Wilms Tumor or other childhood kidney cancers | Adriamycin PFS (Doxorubicin Hydrochloride); Adriamycin RDF (Doxorubicin Hydrochloride); Cosmegen (Dactinomycin); Dactinomycin; Doxorubicin Hydrochloride; Vincasar PFS (Vincristine Sulfate); or Vincristine Sulfate. |

In further aspects, an mTOR inhibitor, e.g., an mTOR inhibitor described herein, may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, an mTOR inhibitor described herein can be used in combination with a chemotherapeutic agent. Exemplary chemotherapeutic agents include an anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. No. 7,812,135, U.S. Pat. No. 8,388,967, U.S. Pat. No. 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, an mTOR inhibitor described herein is administered at a low, immune enhancing, dose to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor, e.g., an SHP-2 inhibitor described herein.

In one embodiment, a low, immune enhancing, dose of an mTOR inhibitor, e.g., an allosteric inhibitor, e.g., RAD001, or a catalytic inhibitor is administered in combination with a kinase inhibitor.

In one embodiment, the kinase inhibitor is an MNK inhibitor, e.g., a MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d] pyrimidine. The MNK inhibitor can be, e.g., a MNK1a, MNK1b, MNK2a and/or MNK2b inhibitor. In one embodiment, the kinase inhibitor is 4-amino-5-(4-fluoroanilino)-pyrazolo [3,4-d] pyrimidine.

In one embodiment, the kinase inhibitor is a CDK4 inhibitor selected from 7-cyclopentyl-N,N-dimethyl-2-((5-(piperazin-1-yl)pyridine-2-yl)amino)-7H-pyrrolo[2,3-d]pyrimidine-6-carboxamide (also referred to as LEE011); aloisine A; flavopiridol or HMR-1275, 2-(2-chlorophenyl)-5,7-dihydroxy-8-[(3 S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., a CDK4 inhibitor described herein, e.g., a CDK4/6 inhibitor, such as, e.g., 7-cyclopentyl-N,N-dimethyl-2-((5-(piperazin-1-yl)pyridine-2-yl)amino)-7H-pyrrolo[2,3-d]pyrimidine-6-carboxamide (also referred to as LEE011) or 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In one embodiment, the kinase inhibitor is a BTK inhibitor, e.g., selected from ibrutinib (PCI-32765); GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered.

In one embodiment, the kinase inhibitor is an mTOR inhibitor. MTOR inhibitors can be selected from the section elsewhere herein entitled mTOR Inhibitors. The dose referred to here is not the low, immune enhancing, dose of an mTOR inhibitor, but rather a dose sufficient to give an anti-cancer effect, and is higher than the low, immune enhancing, dose, described herein, e.g., a dose. Thus, in an embodiment, two different administrations of an mTOR inhibitor are given, a low, immune enhancing dose, e.g., to optimize immune effector cell function, and a higher dose given for an anticancer effect.

In one embodiment, the kinase inhibitor is an mTOR inhibitor, e.g., rapamycin, and the rapamycin is administered at a dose sufficient to give an anti-cancer effect, and higher than the low, immune enhancing, dose, described herein, e.g., a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of rapamycin are administered.

In one embodiment, the kinase inhibitor is an mTOR inhibitor, e.g., everolimus and the everolimus is administered at a dose sufficient to give an anti-cancer effect, and higher than the low, immune enhancing, dose, described herein, e.g., a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In another aspect, an mTOR inhibitor, e.g., an mTOR inhibitor described herein, can be administered at low, immune enhancing, dose in combination with an additional agent which inhibits one or more inhibitory molecules, e.g., PD1, PD-L1, CTLA4, TIM3, LAG3, VISTA, BTLA, TIGIT, LAIR1, CD160, 2B4 and TGFR beta. Inhibition of an inhibitory molecule, e.g., by inhibition at the DNA, RNA or protein level, can lead to increased immune function, as described herein. In embodiments, an inhibitory nucleic acid, e.g., an inhibitory nucleic acid, e.g., a dsRNA, e.g., an siRNA or shRNA, can be used to inhibit expression of an inhibitory molecule. In an embodiment the inhibitor is an shRNA. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

In an embodiment, an mTOR inhibitor can be used in low, immune enhancing, dose in combination with an inhibitor of PD1, e.g., an inhibitor of the interaction of PD1 and one of its natural ligands. In an embodiment, the mTOR inhibitor is administered first, e.g., the PD1 inhibitor is not administered until the level of PD1 positive T cells is reduced. In an embodiment, the mTOR inhibitor is administered at the same time as or after the PD1 inhibitor is administered.

PD1 is an inhibitory member of the CD28 family of receptors that also includes CD28, CTLA-4, ICOS, and BTLA. PD1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1. Antibodies, antibody fragments, and other inhibitors of PD1, PD-L1 and PD-L2 are available in the art and may be used combination with an mTOR inhibitor described herein. For example, nivolumab (also referred to as BMS-936558 or MDX1106; Bristol-Myers Squibb) is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. Pidilizumab (CT-011; Cure Tech) is a humanized IgG1k monoclonal antibody that binds to PD1Pidilizumab and other humanized anti-PD1 monoclonal antibodies are disclosed in WO2009/101611. Lambrolizumab (also referred to as MK03475; Merck) is a humanized IgG4 monoclonal antibody that binds to PD1. Lambrolizumab and other humanized anti-PD1 antibodies are disclosed in U.S. Pat. No. 8,354,509 and WO2009/114335. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.570 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD1 and B7-H1. Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, an mTOR inhibitor, e.g., an mTOR inhibitor described herein, is administered at low, immune enhancing, dose to a subject who has a viral infection, e.g., a viral infection described herein. The subject may receive treatment with an additional therapeutic agent, such as an approved drug for that type of viral infection, in combination with the mTOR inhibitor. Exemplary antiviral agents that may be used in the compositions and methods of the invention include, but are not limited to, Abacavir; Acyclovir; Adefovir; Amantadine; Amprenavir; Ampligen; Arbidol; Atazanavir; Atripla; Balavir; Boceprevirertet; Cidofovir; Combivir; Dolutegravir; Darunavir; Delavirdine; Didanosine; Docosanol; Edoxudine; Efavirenz; Emtricitabine; Enfuvirtide; Entecavir; Ecoliever; Famciclovir; Fomivirsen; Fosamprenavir; Foscarnet; Fosfonet; Ganciclovir; Ibacitabine; Imunovir; Idoxuridine; Imiquimod; Indinavir; Inosine; Interferon; Interferon type I; Interferon type II; Interferon type III; Lamivudine; Lopinavir; Loviride; Maraviroc; Moroxydine; Methisazone; Nelfinavir; Nevirapine; Nexavir; Nucleoside analogues; Oseltamivir (Tamiflu); Peginterferon alfa-2a; Penciclovir; Peramivir; Pleconaril; Podophyllotoxin; Raltegravir; Ribavirin; Rimantadine; Ritonavir; Pyramidine; Saquinavir; Sofosbuvir; Stavudine; Telaprevir; Tenofovir; Tenofovir disoproxil; Tipranavir; Trifluridine; Trizivir; Tromantadine; Truvada; traporved; Valaciclovir; Valganciclovir; Vicriviroc; Vidarabine; Viramidine; Zalcitabine; Zanamivir; and Zidovudine.

In an embodiment the method further comprises the administration of a low, immune enhancing, dose of an mTOR inhibitor in combination with anti-bacterial, anti-mycobacterial, anti-fungal or anti-parasitic or protozoal agents.

Pharmaceutical Compositions

In one aspect, the present invention relates to pharmaceutical compositions comprising an mTOR inhibitor, e.g., an mTOR inhibitor as described herein. In some embodiments, the mTOR inhibitor is formulated for administration in combination with another agent, e.g., as described herein.

In one aspect, the present invention relates to pharmaceutical compositions comprising an mTOR inhibitor as described herein, potentially in combination with an antigen such as a vaccine or vaccine antigen.

In general, compounds of the invention will be administered in therapeutically effective amounts as described above via any of the usual and acceptable modes known in the art, either singly or in combination with one or more therapeutic agents (e.g., a vaccine or other antigen).

The pharmaceutical formulations may be prepared using conventional dissolution and mixing procedures. For example, the bulk drug substance (e.g., an mTOR inhibitor or stabilized form of the compound (e.g., complex with a cyclodextrin derivative or other known complexation agent) is dissolved in a suitable solvent in the presence of one or more of the excipients described herein. The mTOR inhibitor is typically formulated into pharmaceutical dosage forms to provide an easily controllable dosage of the drug and to give the patient an elegant and easily handleable product.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Where an mTOR inhibitor is administered in combination with (either simultaneously with or separately from) another agent as described herein, in one aspect, both components can be administered by the same route (e.g., parenterally). Alternatively, another agent may be administered by a different route relative to the mTOR inhibitor. For example, an mTOR inhibitor may be administered orally and the other agent may be administered parenterally. Pharmaceutical compositions comprising an mTOR inhibitor in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Oral formulations can also comprise the active ingredient along with 20-60% Eudragit EPO, Hydroxypropyl cellulose EF, Hydroxypropyl methylcellulose, or Kollidon VA64, and up to 5% of pluronic F68, Cremophor EL, or Gelucire 44/14. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. In a further aspect, the mTOR inhibitors described herein may be administered via a microneedle patch. Microneedle based drug delivery is well known in the art (See, e.g., U.S. Pat. No. 8,162,901) and these technologies and methods may be adapted by one of skill in the art for administration of an mTOR inhibitor as described herein. Suitable formulations for topical application, e.g., to the skin and eyes, are preferably aqueous solutions, ointments, creams or gels well-known in the art. Such formulations may contain solubilizers, stabilizers, tonicity enhancing agents, buffers and preservatives.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The invention also provides for a pharmaceutical combinations, e.g. a kit, comprising a) a first agent which is an mTOR inhibitor as disclosed herein, in free form or in pharmaceutically acceptable salt form, and b) at least one additional agent. The kit can comprise instructions for its administration.

The term "pharmaceutical combination" as used herein means a product that results from the mixing or combining of more than one active ingredient and includes both fixed and non-fixed combinations of the active ingredients. The term "fixed combination" means that the active ingredients, e.g. an mTOR inhibitor and other agent, are both administered to a patient simultaneously in the form of a single entity or dosage. The term "non-fixed combination" means that the active ingredients, e.g. an mTOR inhibitor and other agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Sustained Release mTOR inhibitors, e.g., allosteric mTOR inhibitors or catalytic mTOR inhibitors, disclosed herein can be provided as pharmaceutical formulations in form of oral solid dosage forms comprising an mTOR inhibitor disclosed herein, e.g., rapamycin or RAD001, which satisfy product stability requirements and/or have favorable pharmacokinetic properties over the immediate release (IR) tablets, such as reduced average plasma peak concentrations, reduced inter- and intra-patient variability in the extent of drug absorption and in the plasma peak concentration, reduced $C_{max}/C_{min}$ ratio and/or reduced food effects. Provided pharmaceutical formulations may allow for more precise dose adjustment and/or reduce frequency of adverse events thus providing safer treatments for patients with an mTOR inhibitor disclosed herein, e.g., rapamycin or RAD001.

In some embodiments, the present disclosure provides stable extended release formulations of an mTOR inhibitor disclosed herein, e.g., rapamycin or RAD001, which are multi-particulate systems and may have functional layers and coatings.

The term "extended release, multi-particulate formulation as used herein refers to a formulation which enables release of an mTOR inhibitor disclosed herein, e.g., rapamycin or RAD001, over an extended period of time e.g. over at least 1, 2, 3, 4, 5 or 6 hours. The extended release formulation may contain matrices and coatings made of special excipients, e.g., as described herein, which are formulated in a manner as to make the active ingredient available over an extended period of time following ingestion.

The term "extended release" can be interchangeably used with the terms "sustained release" (SR) or "prolonged release". The term "extended release" relates to a pharmaceutical formulation that does not release active drug substance immediately after oral dosing but over an extended in accordance with the definition in the pharmacopoeias Ph. Eur. ($7^{th}$ edition) mongraph for tablets and capsules and USP general chapter <1151> for pharmaceutical dosage forms. The term "Immediate Release" (IR) as used herein refers to a pharmaceutical formulation which releases 85% of the active drug substance within less than 60 minutes in accordance with the definition of "Guidance for Industry: "Dissolution Testing of Immediate Release Solid Oral Dosage Forms" (FDA CDER, 1997). In some embodiments, the term "immediate release" means release of everolismus from tablets within the time of 30 minutes, e.g., as measured in the dissolution assay described herein.

Stable extended release formulations of an mTOR inhibitor disclosed herein, e.g., rapamycin or RAD001, can be characterized by an in-vitro release profile using assays known in the art, such as a dissolution assay as described herein: a dissolution vessel filled with 900 mL phosphate buffer pH 6.8 containing sodium dodecyl sulfate 0.2% at 37° C. and the dissolution is performed using a paddle method at 75 rpm according to USP by according to USP testing monograph 711, and Ph. Eur. testing monograph 2.9.3. respectively.

In some embodiments, stable extended release formulations of an mTOR inhibitor disclosed herein, e.g., rapamycin or RAD001, release the mTOR inhibitor in the in-vitro release assay according to following release specifications:

0.5 h: <45%, or <40, e.g., <30%
1 h: 20-80%, e.g., 30-60%
2 h: >50%, or >70%, e.g., >75%
3 h: >60%, or >65%, e.g., >85%, e.g., >90%.

In some embodiments, stable extended release formulations of an mTOR inhibitor disclosed herein, e.g., rapamycin or RAD001, release 50% of the mTOR inhibitor not earlier than 45, 60, 75, 90, 105 min or 120 min in the in-vitro dissolution assay.

In one embodiment, stable extended release formulations of an mTOR inhibitor disclosed herein, e.g., rapamycin or RAD001, comprise an mTOR inhibitor in a fast dissolving or disintegrating carrier matrix in combination with coatings wherein at least one of the coatings is an extended release coating. In another embodiment, stable extended release formulations of an mTOR inhibitor disclosed herein, e.g., rapamycin or RAD001, comprise an mTOR inhibitor in a non-disintegrating carrier matrix with extended release properties, which can be combined optionally with additional coatings.

In some embodiments, a carrier matrix comprises matrix formers, typically matrix forming polymers, and may contain additional excipients, such as fillers, e.g., lactose, mannitol, maltodextrine, pregelatinized starch, calcium phosphate, or microcrystallline cellulose, and disintegrants, e.g., corn starch, croscamellose, sodium starch glycolate, or crospovidone, antioxidants, e.g., butylhydroxy anisol, butylhydroxy toluol, ascorbyl palmitate, tocopherol, vitamin E polyethylene glycol succinate, and process enhancing agents, such as lubricants and glidants, e.g., colloidal silicon dioxide, talc, glyceryl monostearate, magnesium stearate, calcium stearate, or sodium stearyl fumarate. The term "matrix former" typically relates to a pharmaceutically inert material which provides physical stability, such as e.g., mechanical or binding stability.

Suitable matrix forming polymers used for fast dissolving or disintegrating carrier matrices are known in the art include for instance cellulose or starch, for instance microcrystalline cellulose ("MCC"), for example Avicel PH 101 (FMC BioPolymer), acacia, sodium alginate, gelatine, starch, pregelatinised starch, methylcellulose, hydroxypropyl methylcellulose ("HPMC"), hydroxypropylcellulose, hydroxyethylcellulose, polyethylene glycol or polyvinylpyrrolidone ("PVP"), carrageenan, such as Gelcarin GP 812 or combinations thereof.

Suitable matrix forming excipients for non-disintegrating carrier matrices with extended release properties are known in the art include for instance acacia, sodium alginate, gelatine, carboxmethylcellulose sodium, (or "CMC sodium"), methylcellulose, ethylcellulose and cellulose acetate or polyacrylates, e.g., ammonio methacrylate copolymers (Eudragit RS/RL), hydroxypropyl methylcellulose ("HPMC"), hydroxypropylcellulose, hydroxyethylcellulose, polyvinylacetate, polyethylene glycol or polyvinylpyrrolidone ("PVP"), e.g., carrageenan, such as Gelcarin GP 812, glyceryl monostearate, stearylalcohol, stearic acid, glyceryl behenate, Vitamin E polyethylen glycol succinate, or combinations thereof.

In one embodiment, the extended release coating is a layer formed with water insoluble, non-disintegrating polymers, controlling the release by permeation of the drug through this layer.

The extended release coating may also contain one or more of pore formers, plasticizers, and processing enhancing agents, such as lubricants and anti tacking agents. Suitable extended release coating forming polymers which enable diffusion controlled release are known in the art include for instance ethylcellulose and cellulose acetate or polyacrylates, e.g., ammonio methacrylate copolymers (Eudragit RS/RL), polyvinylacetate or combinations thereof. In a particular embodiment, the extended release coating forming polymer is ethylcellulose or cellulose acetate or polyacrylates, e.g., ammoniomethacrylate copolymer Type A (Eudragit RS) or ammonio-methacrylate copolymer Type B (Eudragit RL) or combinations thereof. Moreover, the extended release coating may include plasticizer, such as triacetine, triethyl citrate, dibutylsebacate, diethylsebacate, polyethylene glycol 3000, 4000 or 6000, acetyltriethylcitrate, acetyltributylcitrate, or diethylphthalate, and/or anti-tacking agents such Syloid 244 FP, talc, glyceryl monostearate, or titanium dioxide. In some embodiments, the amount of plasticizer may be between 5 to 40%, preferably 10 to 25%, relative to the amount of sustained release polymer.

In an embodiment, an extended release coating is a pore forming system which comprises a water insoluble coating forming polymer and a pore former. The term "pore former" relates to a readily soluble excipient which allows pores to be introduced or permeability of the coating to be increased, and a diffusion controlled release of the active ingredient. Suitable pore formers are known in the art include for instance hydroxypropylcellulose (HPC (e.g., Klucel™ EF, EXF, LF), or hydroxypropyl methylcellulose (HPMC, e.g., Methocel™ E3/E5, Pharmacoat 603™), polyethylen glycol (e.g., Macrogol 1500, 3500, 4000, 6000), poloxamer 188 (Pluronic F68™) or povidone (PVP, e.g., Kollidon K25/K30), a saccharide, e.g., a monosaccharide, such as dextrose, mannose, fructose, a disaccharide, such as sucrose or glucodifructose or combinations thereof. Preferably the pore former is hydroxypropylcellulose (HPC (Klucel™ EF, EXF, LF), or hydroxypropyl methylcellulose (HPMC, Methocel™ E3/E5, Pharmacoat 603™) polyethylen glycol (Macrogol 1500, 3500, 4000, 6000), poloxamer 188 (Pluronic F68™) or povidone (PVP, Kollidon K25/K30) or combinations thereof. In some embodiments, suitable amounts of pore formers included in coating are equal to ratios of coating polymer to pore former of e.g. 100:20 to 100:50, or 100:20 to 100:100, preferably ratios of 100:35 to 100:45, particularly ratios of 100:35 to 100:50 relative to the amount of coating forming polymer. In some embodiments, suitable amounts of coating forming polymers included are equal to percentages of polymer weight increase of e.g., 4% to 15%, 5% to 15%, preferably 5% to 12%, more preferably 6% to 12% weight of total weight of pharmaceutical formulation.

In another embodiment, a non-disintegrating extended release carrier matrix comprises matrix forming polymers which enable diffusion controlled release of the active ingredient by hydration of the polymer. The extended carrier matrix may contain further excipients, such as binders and or fillers and process enhancing agents, such as lubricants and glidants, etc.

The following exemplary matrix forming polymers may be used for diffusion controlled release: sodium alginate, polyacrylic acids (or "carbomers"), carboxmethylcellulose sodium, (or "CMC sodium"), methylcellulose, ethylcellulose and cellulose acetate or polyacrylates, e.g., ammonio methacrylate copolymers (Eudragit RS/RL), hydroxypropyl methylcellulose ("HPMC") of different viscosity grades (i.e., average polymer chain lengths) and combinations thereof, e.g., Methocel™ CR grades, hydroxypropyl cellulose, e.g. Klucel™ HF/MF, polyoxyethylene, e.g., Polyox™ or polyvinylpyrrolidone ("PVP"), e.g., PVP K60, K90, carrageenan, such as Viscarin™ GP-209/GP-379, or combinations thereof. Combining of matrix forming polymers allows adjusting the dissolution rate of the active ingredient according to the need.

In some embodiments, a non-disintegrating extended release matrix is formed with excipients, which enable release of the active ingredient by a controlled erosion. The erosion controlled matrices may contain lipophilic matrix formers, and also further excipients, such as fillers, disintegrants and process enhancing excipients, such as lubricants and glidants. Exemplary lipophilic matrix forming excipients related to this matrix type include lipophilic excipients, such as glyceryl monostearate, e.g., Cutina GMS, glyceryl behenate, e.g., Compritol 888 ATO, stearyl alcohol, stearic acid, hart fat, e.g., Gelucire™, or Vitamin E polyethylen glycol succinate, e.g., Speziol TPGS or combinations thereof.

Exemplary suitable binders, fillers or further excipients include, but are not limited to, mannitol, pregelatinized starch, microcrystalline cellulose, lactose, calcium phosphate, talc, titanium dioxide, triethylcitrate, Aerosil, antioxidants such as e.g., BHT, desiccants and disintegrant such as e.g., crospovidone or sodium starch glycolate, starch, or croscarmellose.

In an embodiment, a stable extended release formulation comprises an mTOR inhibitor disclosed herein, e.g., rapamycin or RAD001, in a fast dissolving/disintegrating matrix, e.g., in form of a solid dispersion as described herein, in combination with functional layers or coatings wherein at least one of the functional layer(s) or coating(s) has release controlling behavior enabling extended release of the active ingredient. In another embodiment, a stable extended release formulation comprises an mTOR inhibitor disclosed herein, e.g., rapamycin or RAD001, in the extended release matrix which, optionally, can further contain functional layers or coatings, such as protective or sustained release layers or coatings. In some embodiments, the coating, e.g., the extended release coating may have a thickness in the range of 10 to 100 µm, e.g., 10 to 50 µm (assessed by confocal RAMAN spectroscopy).

In some embodiments, the formulation of an mTOR inhibitor disclosed herein, e.g., rapamycin or RAD001, is in form of a multi-particulate delivery system. In some embodiments, a multi-particulate drug delivery system is an oral dosage form consisting of multiple, small discrete dose units. In such systems, the dosage form of the drug substances such as capsule, tablets, sachet or stickpack, may contain a plurality of subunits, typically consisting of tens to hundreds or even up to thousands of spherical particles with diameter of 0.05-2.00 mm. Formulations of the size 1.5-3 mm, e.g., minitablets, present another alternative. The dosage form may be designed to disintegrate rapidly in the stomach releasing the multi-particulates. Without wishing to be bound by a particular theory, it is thought that the multi-particulates are spread in the gastro-intestinal lumen and will be emptied gradually from the stomach releasing the drug substance in a controlled manner.

In one embodiment, the formulation of an mTOR inhibitor disclosed herein, e.g., rapamycin or RAD001, e.g., in form of multi-particulate delivery system, comprises an mTOR inhibitor as active ingredient, e.g., dissolved or dispersed in the core of the particle, (e.g., a bead, pellet, granule or minitablet), or in a layer surrounding an inert core of the particle. The active ingredient can be for instance be embedded in an extended release matrix, preferably comprising a hydrophilic or lipophilic matrix forming excipients, or embedded in a fast disintegrating and/or dissolving matrix in combination with functional layer(s) and top coating(s) wherein at least one of the functional layer(s) or top coating(s) comprises a coating forming polymer enabling diffusion controlled extended release of the active ingredient. Optionally, a protection layer for improving stability of the active ingredient separates the matrix containing the active substance from functional layers or top coatings, to ensure stability of the drug product.

In a another embodiment, the formulation of an mTOR inhibitor disclosed herein, e.g., rapamycin or RAD001, e.g., in form of a multi-particulate delivery system, comprises an mTOR inhibitor as active ingredient and an outer coating layer comprising an insoluble polymer and a soluble component as pore former, and optionally further functional layers. For the purpose of the present invention the terms "outer layer" is a layer located towards to the outside of a particle and may be coated with a further layer(s) or may be a top coating. The terms "outer layer", "coating layer" or "top coat" may be used interchangeably depending on the context in which the terms are used.

In one embodiment, the particles comprise one or several top coats enabling extended release of the active ingredient. Top coats typically are final layers with release controlling behavior, which are enclosing each particle of the multi-particulates separately.

In an embodiment, the formulation of an mTOR inhibitor disclosed herein, e.g., rapamycin or RAD001, comprises an outer layer or a top coating that controls the release by the diffusion of the drug through the coating layer which is permeable, optionally by the formation of pores in the insoluble polymer layer, or alternatively solely by the hydration of the insoluble polymer, or that controls the release by a combination of a pore former and hydration of the insoluble polymer. The polymer is insoluble independently from pH, and optionally contains water soluble pore former. The release rate is affected by the extent of pore formation after the pore former is dissolved. The insoluble coating polymer can be cellulose ethers such as ethylcellulose and cellulose acetate or polyacrylates, e.g., ammonio methacrylate copolymers (Eudragit RS/RL). Suitable pore formers include water soluble cellulose ethers, for instance hydroxypropylcellulose (HPC (Klucel™ EF, EXF, LF) or hydroxypropyl methylcellulose (HPMC, Methocel™ E3/E5, Pharmacoat 603™), polyethylen glycol (Macrogol 1500, 3500, 4000, 6000), poloxamer 188 (Pluronic F68™) or povidone (PVP, Kollidon K12, K25, K30). For instance, water soluble pore former can be mixed with insoluble polymer in a ratio of 2:1 to 1:10, e.g. 1:1 to 1:5, 1:3 or 1:5. In an embodiment, the pore former to insoluble polymer ratio is HPC, e.g Klucel™ EF, EXF, LF or HMPC 3 cP, e.g., Methocel™ E3, in a ratio of 1:1 to 1:4, e.g., about 1:1, 1:1.2, 1:1.5 or 1:2. Exemplary insoluble polymers include, but are not limited to ethylcellulose (EC, Aqualon EC N10™) in combination with a pore former. In some embodiments, without the use of a pore former, the combination of the insoluble polymers ammoniomethacrylate copolymer Type A (Eudragit RS) and ammonio-methacrylate copolymer Type B (Eudragit RL) may be at ratios of 1:2 to 9:1, preferably 1:1 to 4:1.

A sustained release top coat(s) may achieve release of majority of the active substance into the small intestine and allows protection of the active substance from stomach fluids and minimizes the exposure of the active substance to the mouth, esophagus and stomach.

In one embodiment, the formulation of an mTOR inhibitor disclosed herein, e.g., rapamycin or RAD001, comprise a drug substance containing matrix, e.g., fast disintegrating and/or dissolving matrix layer or in an extended release matrix layer, e.g., on a starter core such as beads, pellets or granules, which can consist of one or more components, and in which the active ingredient is dispersed or dissolved. For instance, amorphous or crystalline mTOR inhibitor, e.g., rapamycin or RAD001, can be dispersed or dissolved in the matrix in a ratio from 1:100 to 100:1 in the matrix, e.g., 1:50 to 5:1; or 1:50 to 1:1 by weight, or 1:5 to 2:3, or 1:10 to 1:5 by weight (as to the matrix former).

In an embodiment, the drug substance containing matrix is layered onto the surface of starter cores. The layer may be built by spraying a dispersion or solution of the matrix components and the drug substance on to particles of uniform, regular size and shape in a fluid bed process. Alternatively, powder mixtures of the matrix components can be layered using a rotating disk processor. Starter cores have an average particle size 0.1 to 2.5 mm. They can be single crystals, e.g., sucrose, or granular agglomerates manufactured by fluid bed granulation, a rotorgranulation, extrusion and spheronization, or a compaction process. In some embodiments, minitablets can be used as starter cores. In particular embodiments, the starter cores have a spherical shape and consist of inert material such as sucrose and starch (Sugar Spheres, Suglets™, Non-pareils), mannitol (e.g. MCells™), lactose (e.g., spray dried lactose) or microcrystalline cellulose (e.g., Cellets™).

In another embodiment, the drug substance containing matrix is incorporated in the cores of the particles. The matrix forming excipients, fillers, and other ingredients for enhancing the process are mixed together with the drug substance. The powder mixtures obtained can be formulated as particles by using wet extrusion or melt extrusion and subsequent spheronization, or by compacting the mixtures to minitablets. The matrices formed could be either fast disintegrating/dissolving matrices, or non-disintegrating matrices with extended release properties built with hydrophilic or lipophilic matrix forming excipients.

In an embodiment, multi-particulates consisting of a hydrophilic, non-disintegrating matrix which contains the drug substance or a solid dispersion thereof, are prepared by mixing the active ingredient, a filler, e.g., lactose, together with hydrophilic, hydrogel forming polymers with different viscosities, a glidant, and a lubricant. In some embodiments, the hydrophilic, hydrogel forming polymer may be, for example hydroxypropyl methylcellulose, with low viscosity grade of less than 20 mPas for a 2% by weight aqueous solution, e.g., Methocel E5, combined with hydroxypropyl methylcellulose grade with high viscosity of more than 100 mPas for a 2% by weight aqueous solution, e.g., Methocel K100. The powder mixture is then compressed on the tabletting machine to obtain minitablets. Alternatively, the powder mixture can be wetted with organic solvent, e.g., ethanol, and then extruded and spheronized for obtaining multi-particulates.

In another embodiment, multi-particulates consisting of a lipophilic, non-disintegrating matrix which contains the drug substance or a solid dispersion thereof are prepared by mixing the active ingredient, lipophilic, meltable, matrix forming excipients, and fillers. The mixture is processed by melting and mixing in an extruder. The obtained extudate strands are cut into particles and are optionally spheronized. The lipophilic excipients used are for example Vitamin E polyethylen glycol succinate (Vit E TPGS, e.g., Kolliphor TPGS Pharma from BASF) solely, or in combination with glycerol monostearate (GMS, e.g., Kolliwax GMS from-BASF) at ratios of 9:1 to 1:9.

In some embodiments, an extended release formulation of an mTOR inhibitor disclosed herein, e.g., rapamycin or RAD001, reduces the peak concentration ($C_{max}$) to concentration at 24 hours post-dose ($C_{24h}$) ratio after a single dose administration in 24 healthy subjects, as compared to an immediate release tablet, e.g., a rapamycin or RAD001 immediate release tablet available to patients (Final Market Image or "FMI" tablets). In some embodiments, the $C_{max}/C_{24h}$ ratio is decreased, e.g., as measured by pharmacokinetic model simulations. An advantage of a reduced $C_{max}/C_{min}$ ratio is that, with the appropriate dose based on the bioavailability of the mTOR inhibitor relative to an FMI formulation, the concentration of mTOR inhibitor may be maintained above the lower therapeutic range of drug (for sufficient efficacy) and at the same time distance away from the upper therapeutic range of drug (concentration region of toxicity). Thus, in some embodiments, an extended release formulation of an mTOR inhibitor disclosed herein, e.g., rapamycin or RAD001, is able to improve the safety profile of the mTOR inhibitor without affecting its efficacy. In an embodiment, a $C_{max}/C_{24h}$ (thus $C_{max}/C_{min}$) ratio in patients having been administered an extended release formulation of an mTOR inhibitor disclosed herein, e.g., rapamycin or RAD001, is <5 or <4, e.g. 3.5±1 or 3±0.5.

In an embodiment, an mTOR inhibitor disclosed herein, e.g., rapamycin or RAD001, is contained in a layer separate from the functional layer or top coat controlling the extended release properties of the formulation. Such layer may be made of any substance which is suitable for dispersing or dissolving the mTOR inhibitor. In an embodiment, the layer comprising the mTOR inhibitor is made of a hydrophilic carrier matrix. The carrier matrix may be embedding the active ingredient and protecting it against degradation. Suitable matrix formers include, but are not limited to, hydrophilic polymers, e.g. HPMC type 2910 or type 2280, HPC, HEC, MEC, MHEC, povidone, which can be dissolved or rapidly dispersed in water. In one embodiment, the matrix layer is in form of a solid dispersion, for instance as described in WO97/03654 or WO03/028705, the entire contents of each of which are incorporated herein by reference.

In an embodiment, the fast dissolving/disintegrating carrier matrix for an mTOR inhibitor disclosed herein, e.g., rapamycin or RAD001, is in form of a solid dispersion. In some embodiments, the solid dispersion comprises a carrier, e.g., a water-soluble polymer, for example one or a mixture of the following polymers may be used:

hydroxypropylmethylcellulose (HPMC), e.g., Hypromellose type 2910, which is available as Methocel™ E from Dow Chemicals or Pharmacoat™ from Shin Etsu. Good results may be obtained using HPMC with a low apparent viscosity, e.g., below 100 cps as measured at 20° C. for a 2% by weight aqueous solution, e.g. below 50 cps, preferably below 20 cps, for example HPMC 3 cps;

polyvinylpyrrolidone (povidone, PVP), e.g., PVP K25, K30 or PVP K12. PVP is available commercially, for example, as Kollidon® from the BASF company or as Plasdone® from ISP company. A PVP having an average molecular weight between about 8,000 and about 50,000 Daltons is preferred, e.g., PVP K30;

hydroxypropylcellulose (HPC), e.g., Klucel EF/LF/J For a derivative thereof. Examples of HPC derivatives include those having low dynamic viscosity in aqueous media, e.g., water, e.g. below about 400 cps as measured in a 5% aqueous solution at 25° C. Preferred HPC derivatives an average molecular weight below about 200,000 Daltons, e.g., between 80,000 and 140,000 Daltons. Examples of HPC available commercially include Klucel® LF, Klucel® EF and Klucel® JF from the Hercules Aqualon company; and Nisso® HPC-L available from Nippon Soda Ltd;

a polyethylene glycol (PEG). Examples include PEGs having an average molecular weight between 1000 and 9000 Daltons, e.g. between about 1800 and 7000, for example PEG 2000, PEG 4000, or PEG 6000 (Handbook of Pharmaceutical Excipients, p. 355-361);

a saturated polyglycolised glyceride, available for example, as Gelucire®, e.g., Gelucire® 44/14, 53/10, 50/13, 42/12, or 35/10 from the Gattefossé company; or a cyclodextrin, for example a β-cyclodextrin or an α-cyclodextrin. Examples of suitable β-cyclodextrins include, but are not limited to, methyl-β-cyclodextrin; dimethyl-β-cyclodextrin; hydroxypropyl-β-cyclodextrin; glycosyl-β-cyclodextrin; maltosyl-β-cyclodextrin; sulfo-β-cyclodextrin; a sulfo-alkylethers of β-cyclodextrin, e.g. sulfo-$C_{1-4}$-alkyl ethers. Examples of α-cyclodextrins include, but are not limited to, glucosyl-α-cyclodextrin and maltosyl-α-cyclodextrin.

In one embodiment, an mTOR inhibitor-containing layer contains antioxidant in a ratio of 1:1000 to 1:1 related to the amount of drug substance. The antioxidant may also be present in other functional layers, e.g., at concentration of 0.1 to 10%, preferably 0.1 to 1%. Suitable antioxdants include, but are not limited to, butyl hydroxyl toluol, butyl hydroxy anisol, ascorbyl palmitate, tocopherol, vitamin E polyethylene glycol succinate. In a particular embodiment, the antioxidant is butyl hydroxyl toluol.

In one embodiment, a protection layer separates the layer containing the active substance from other functional layers, such as e.g., the top coating, to enhance stability of the of the drug product. The drug substance is stabilized by excluding any direct contact with the top coating. The protection layer also acts as diffusion barrier preventing any components in the top coating, e.g., polymer by-products or plasticizers, which can migrate through the layers, from getting in direct contact with the active. Beside the polymers, which are used also as matrix formers (e.g., the matrix formers described above), high content, of inorganic pigments or anti-tacking agents such as talc and/or titanium dioxide, e.g., 10 to 100%, e.g., 20 to 50%, relative to the applied amount of polymer, contribute to the barrier function. The protection layer thickness can be adjusted to gain optimized drug product stability.

In another embodiment, the mTOR inhibitor, e.g., rapamycin or RAD001, is directly embedded in the extended release carrier matrix.

In some embodiments, a formulation comprising an mTOR inhibitor disclosed herein, e.g., rapamycin or RAD001, contains strongly hygroscopic excipients, which are able to bind water moisture enclosed in the formulation working as an internal desiccant. Adsorbents such as e.g., crospovidone, croscarmellose sodium, sodium starch glycolate, or starch can be used. For example, in some embodiments, crospovidone is used as tablet disintegrant, e.g., at 2% to 25% crospovidone. The adsorbent, e.g., crospovidone, may be part of the powder mixtures used for wet and melt extrusion, part of the powder blend for compressing the minitablets, part of powder blend for tabletting the multi-particulates, and/or directly added to the multi-particulates in a sachet or capsule filling process.

In one aspect, an mTOR inhibitor disclosed herein, e.g., rapamycin or RAD001, is present in a particle (e.g., 0.1 to 0.5 mm), bead, pellet (e.g., 0.2 to 2 mm) or mini-tablet (e.g., 1.5 to 3 mm), with a low water moisture content of less than 5% in total, e.g., less than 3% or less than 2.5% in total.

In some embodiments, a pharmaceutical compositions, e.g., a multi-particulate delivery system of an mTOR inhibitor disclosed herein, e.g., rapamycin or RAD001, can be formulated into a drug product such as e.g., capsules (e.g., HPMC or Hart Gelatine capsules), or filled into sachets or stick-packs, or formulated as tablets which release the particles upon disintegration.

In some embodiments, the primary packaging, such as sachets, stickpacks, blisters or bottles may include an water sorbing ingredient, e.g., silica gel, which reduces or stabilizes the water moisture content of the drug product during shelf life storage and/or in during in-use time.

Provided formulations may comprise and/or release multiple pellets, granules or minitablets.

In some embodiments, provided formulations, e.g., multi-particulates formulations, can be prepared by extruding and spheronizing a mixture of the matrix forming excipients together with the drug substance with the aid of heat or wetting liquids, or by compacting minitablets with drug containing mixtures, or by layering the drug containing matrix layer onto cores in a fluid bed or rotogranulation process.

In some embodiments, the layer containing the active substance can be prepared by spraying a spray dispersion with organic solvents in which the hydrophilic components and the active substance are dispersed or dissolved onto the core material, while concurrently the solvents are continuously removed by the aid of heated, dry air. By this process a matrix layer surrounding the cores is formed, e.g., the layer formed is a solid dispersion of the active in polymers such as e.g., HPMC, HPC, HEC.

In one aspect, a provided pharmaceutical formulation may be prepared as follows: An organic feed mixture for spraying in which the hydrophilic polymer is dispersed in colloidal manner and an mTOR inhibitor disclosed herein, e.g., rapamycin or RAD001, is dispersed or dissolved, which precipitate together as a uniform, smooth layer of solid dispersion upon removal of the solvent in such a way that they can be coated with modified release coats. In some embodiments, the obtained drug containing multi-particulates can be coated with additional functional layers and top coatings. A spray dispersion containing coating polymers, lubricants, anti tack agents, pore formers and plastisizers, which are dissolved, dispersed and suspended in organic solvents and mixtures thereof, is sprayed onto the drug containing multi-particulates. During processing the multi-particulates are kept continuously in a controlled motion or fluidization, while dry, heated process gas is applied to the product bed for evaporating the solvents from the surface of the multi-particulates, where the film layer is formed at a defined temperature. The film layer thickness can be controlled by the amount of coating dispersion sprayed. Final drying is applied for minimizing the residual solvent content in the layered and coated multi-particulates.

In another aspect, an mTOR inhibitor disclosed herein, e.g., rapamycin or RAD001, may be formulated as part of a high drug load part of an extended release formulation. In some embodiments, the formulation further comprises a surfactant. The term "surfactant" can be used interchangeably with a "wetting agent" or "detergent" and refers to a non-ionic, ionic, anionic, cationic or amphoteric surfactant, e.g., a non-ionic, ionic, anionic, or amphoteric surfactant. Examples of suitable surfactants/wetting agents include, but are not limited to, polyoxyethylene-polyoxypropylene co-polymers and block co-polymers known, for example, under the trademarks Pluronic or Poloxamer (e.g. poloxamer 188 (Pluronic F68), polyoxyethylene, sorbitan fatty acid esters including mono and tri lauryl, palmityl, stearyl and oleyl esters of the type known under the trade name Tween, polyoxyethylene fatty acid esters including polyoxyethylene stearic acid esters of the type known under the trade name Myrj, polyoxyethylene alkyl ethers known under the trade mark Brij, sodium alkyl sulfates like Soldium lauryl sulphate (SDS) and sulfonates, and sodium alkyl aryl sulfonates, water soluble tocopheryl polyethylene glycol succinic acid esters (TPGS), polyglycerol fatty acid esters, alkylene polyol ethers or esters, polyethylene glycol glyceryl fatty acid esters, sterols and derivatives thereof, trans-esterified, polyoxyethylated caprylic-capric acid glycerides, sugar fatty acid esters, PEG sterol ethers, phospholipids, salts of fatty acids, fatty acid sulfates and sulfonates, salts of fatty acids, fatty acid sulfates and sulfonates, medium or long-chain alkyl, e.g., $C_6$-$C_{18}$, ammonium salts, bile acid or salt thereof; for example cholic acid, glycolic acid or a salt, e.g., sodium cholate and polyoxyethylene mono esters of a saturated $C_{10}$ to $C_{22}$ fatty acid. In a particular embodiment the surfactant is polyoxyethylene-polyoxypropylene co-polymer or block co-polymer, or a water soluble tocopheryl polyethylene glycol succinic acid ester, e.g., a water soluble tocopheryl polyethylene glycol succinic acid ester, e.g., Vitamin E polyethylene glycol 1000 succinate (TPGS). In another embodiment the surfactant in the present pharmaceutical formulation is polyoxyethylene-polyoxypropylene co-polymer, e.g., poloxamer 188. In yet another embodiment, the pharmaceutical formulation comprises the surfactant sodium alkyl sulfate, e.g., sodium lauryl sulfate.

The surfactant or wetting agent may be present in a formulation in a ratio to mTOR inhibitor, e.g., rapamycin or RAD001, from 10:1 to 1:200 by weight, e.g., 1:1 to 1:100 by weight, 1:2 to 1:8 by weight, 1:4 to 1:6 by weight.

In some embodiments, the mTOR inhibitor, e.g., rapamycin or RAD001, is in a high drug load containing first layer, and a surfactant in a second layer, wherein the second layer is beneath the first layer, optionally with additional extended release coating. In some such embodiments, the surfactant is not poloxamer 188 and TPGS. In some embodiments, the surfactant or wetting agent in a second layer can form a protection layer which separates the active ingredient containing layer from the coating covering the formulation. The coating covering the formulation may be an extended release coating.

Other Embodiments

The invention further provides T cell preparations of T cells treated with a low, immune enhancing, dose of mTOR inhibitor, as described herein, e.g., for use in treating a subject with a disease, e.g., a lymphoproliferative disease. In some embodiments, the T cells are recovered from a subject that has been administered a low, immune enhancing, dose of mTOR inhibitor, as described herein. Suitable methods of recovering T cells from a subject are known in the art, and include isolation from peripheral blood or bone marrow by filtration, affinity chromatography, or magnetic labelling and separation. In other embodiments, the T cells recovered from a subject are treated with a low, immune enhancing, dose of mTOR inhibitor as described herein in vitro, e.g., in cell culture. In one embodiment, the T cell preparation is obtained from a subject with a lymphoproliferative disease before the subject receives a bone marrow or stem cell transplant, and the T cell preparation is delivered to the subject after the bone marrow or stem cell transplant. The T cell preparation can increase or improve the effect of the bone marrow or stem cell transplant, e.g., increasing anti-cancer cell immune function and recovery of the immune system. The lymphoproliferative disease can be a leukemia or a lymphoma, e.g., chronic myelogenous leukemia (CML), acute myeloid leukemia (AML), Burkitt's lymphoma, diffuse large cell lymphoma, follicular lymphoma, hairy cell lymphoma, mantle cell lymphoma, myelodysplastic syndromes, and non-Hodgkin's lymphoma.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Effects of mTOR Inhibition on Immunosenescence in the Elderly

One of the pathways most clearly linked to aging is the mTOR pathway. The mTOR inhibitor rapamycin has been shown to extend lifespan in mice and improve a variety of aging-related conditions in old mice (Harrison, D E et al. (2009) Nature 460:392-395; Wilkinson J E et al. (2012) Aging Cell 11:675-682; and Flynn, J M et al. (2013) Aging Cell 12:851-862). Thus, these findings indicate that mTOR inhibitors may have beneficial effects on aging and aging-related conditions in humans.

An age-related phenotype that can be studied in a short clinical trial timeframe is immunosenescence. Immunosenescence is the decline in immune function that occurs in the elderly, leading to an increased susceptibility to infection and a decreased response to vaccination, including influenza vaccination. The decline in immune function with age is due to an accumulation of immune defects, including a decrease in the ability of hematopoietic stem cells (HSCs) to generate naïve lymphocytes, and an increase in the numbers of exhausted PD-1 positive lymphocytes that have defective responses to antigenic stimulation (Boraschi, D et al. (2013) Sci. Transl. Med. 5:185ps8; Lages, C S et al. (2010) Aging Cell 9:785-798; and Shimatani, K et al., (2009) Proc. Natl. Acad. Sci. USA 106:15807-15812). Studies in elderly mice showed that 6 weeks of treatment with the mTOR inhibitor rapamycin rejuvenated HSC function leading to increased production of naïve lymphocytes, improved response to influenza vaccination, and extended lifespan (Chen, C et al. (2009) Sci. Signal. 2:ra75).

To assess the effects of mTOR inhibition on human aging-related phenotypes and whether the mTOR inhibitor RAD001 ameliorates immunosenescence, the response to influenza vaccine in elderly volunteers receiving RAD001 or placebo was evaluated. The findings presented herein suggest that RAD001 enhanced the response to influenza vaccine in elderly volunteers at doses that were well tolerated. RAD001 also reduced the percentage of programmed death (PD)-1 positive CD4 and CD8 T lymphocytes that accumulate with age. These results show that mTOR inhibition has beneficial effects on immunosenescence in elderly volunteers.

As described herein, a 6 week treatment with the mTOR inhibitor RAD001, an analog of rapamycin, improved the response to influenza vaccination in elderly human volunteers.

Methods

Study Population

Elderly volunteers >=65 years of age without unstable underlying medical diseases were enrolled at 9 sites in New Zealand and Australia. Exclusion criteria at screening included hemoglobin <9.0 g/dL, white blood cell count <3,500/mm$^3$, neutrophil count <2,000/mm$^3$, or platelet count <125,000/mm$^3$, uncontrolled diabetes, unstable ischemic heart disease, clinically significant underlying pulmonary disease, history of an immunodeficiency or receiving immunosuppressive therapy, history of coagulopathy or medical condition requiring long-term anticoagulation, estimated glomerular filtration rate <30 ml/min, presence of severe uncontrolled hypercholesterolemia (>350 mg/dL, 9.1 mmol/L) or hypertriglyceridemia (>500 mg/dL, 5.6 mmol/L).

Baseline demographics between the treatment arms were similar (Table 2). Of the 218 subjects enrolled, 211 completed the study. Seven subjects withdrew from the study. Five subjects withdrew due to adverse events (AEs), one subject withdrew consent, and one subject left the study as a result of a protocol violation.

TABLE 2

Demographic and Baseline characteristics of the Study Patients

| Population | | RAD001 0.5 mg daily N = 53 | RAD001 5 mg weekly N = 53 | RAD001 20 mg weekly N = 53 | Placebo pooled N = 59 | Total N = 218 |
|---|---|---|---|---|---|---|
| Age (Years) | Mean (SD) | 70.8 (5.0) | 72.0 (5.3) | 71.4 (5.2) | 71.1 (5.1) | 71.3 (5.2) |
| Gender | Male-n (%) | 34 (64%) | 27 (51%) | 32 (60%) | 31 (53%) | 124 (57%) |
| BMI* (kg/m2) | Mean (SD) | 27.4 (4.2) | 28.8 (5.0) | 28.0 (4.1) | 28.0 (4.2) | 28.0 (4.4) |

TABLE 2-continued

Demographic and Baseline characteristics of the Study Patients

| Population | | RAD001 0.5 mg daily N = 53 | RAD001 5 mg weekly N = 53 | RAD001 20 mg weekly N = 53 | Placebo pooled N = 59 | Total N = 218 |
|---|---|---|---|---|---|---|
| Race-n (%) | Caucasian | 48 (91%) | 50 (94%) | 46 (87%) | 54 (92%) | 198 (91%) |
| | Other | 5 (9%) | 3 (6%) | 7 (13%) | 5 (8%) | 20 (9%) |

*The body-mass index is weight in kilograms divided by the square of the height in meters Study Design and Conduct From December 2011 to April 2012, 218 elderly volunteers were enrolled in a randomized, observer-blind, placebo-controlled trial. The subjects were randomized to treatment arms using a validated automated randomization system with a ratio of RAD001 to placebo of 5:2 in each treatment arm. The treatment arms were:

RAD001 0.5 mg daily or placebo
RAD001 5 mg weekly or placebo
RAD001 20 mg weekly or placebo The trial was observer-blind because the placebo in the RAD001 0.5 mg daily and 20 mg weekly cohorts differed slightly from the RAD001 tablets in those cohorts. The study personnel evaluating the subjects did not see the study medication and therefore were fully blinded. The treatment duration for all cohorts was 6 weeks during which time subjects underwent safety evaluations in the clinic every 2 weeks. After subjects had been dosed for 4 weeks, RAD001 steady state levels were measured pre-dose and at one hour post dose. After completing the 6 week course of study drug, subjects were given a 2 week drug free break to reverse any possible RAD001-induced immunosuppression, and then were given a 2012 seasonal influenza vaccination (Agrippal®, Novartis Vaccines and Diagnostics, Siena, Italy) containing the strains H1N1 A/California/07/2009, H3N2 A/Victoria/210/2009, B/Brisbane/60/2008. Four weeks after influenza vaccination, subjects had serum collected for influenza titer measurements. Antibody titers to the 3 influenza vaccine strains as well as to 2 heterologous strains (A/H1N1 strain A/New Jersy/8/76 and A/H3N2 strain A/Victoria/361/11) were measured by standard hemagglutination inhibition assay (Kendal, A P et al. (1982) *Concepts and procedures for laboratory-based influenza surveillance. Atlanta: Centers for Disease Control and Prevention* B17-B35). Levels of IgG and IgM specific for the A/H1N1/California/07/2009 were measured in serum samples taken before and 4 weeks after influenza vaccination as described previously (Spensieri, F. et al. (2013) *Proc. Natl. Acad. Sci. USA* 110:14330-14335). Results were expressed as fluorescence intensity.

All subjects provided written informed consent. The study was conducted in accordance with the principals of Good Clinical Practice and was approved by the appropriate ethics committees and regulatory agencies.

Safety

Adverse event assessment and blood collection for hematologic and biochemical safety assessments were performed during study visits. Adverse event information was also collected in diaries that subjects filled out at home during the 6 weeks they were on study drug. Data on all adverse events were collected from the time of informed consent until 30 days after the last study visit. Events were classified by the investigators as mild, moderate or severe.

Statistical Analysis

The primary analysis of geometric mean titer ratios was done using a normal Bayesian regression model with non-informative priors. This model was fitted to each antibody titer on the log scale. The primary outcome in each model was the Day 84 measurement. The Day 63 measurement was included in the outcome vector. The model fitted using SAS 9.2 proc mixed with the prior statement. The covariance structure of the matrix was considered as unstructured (option type=UN). A flat prior was used. For the secondary analysis of seroconversion rates, logistic regression was used.

The intention to treat population was defined as all subjects who received at least one full dose of study drug and who had no major protocol deviations impacting efficacy data. 199 out of the total of 218 subjects enrolled in the study were in the intention to treat population.

Immunophenotyping

Peripheral blood mononuclear cells were isolated from whole blood collected at 3 time points: baseline; after 6 weeks of study drug treatment; and at the end of study when subjects had been off study drug for 6 weeks and 4 weeks after influenza vaccination. Seventy-six PBMC subsets were analyzed by flow cytometry using 8-color immunophenotyping panels at the Human Immune Monitoring Center at Stanford University, CA, USA as described previously (Maecker, H T et al. (2012) *Nat Rev Immunol.* 12:191-200). Seventy-six PBMC subsets were analyzed by flow cytometry using 8-color lyophilized immunophenotyping panels (BD Lyoplate, BD Biosciences, San Diego, Calif.). PBMC samples with viability >80% and yield of $2 \times 10^6$ cells or greater were included in the analysis.

Relative changes of the immunophenotypes from baseline to Week 6 of study drug treatment and from baseline to the end of study (Week 12) were calculated for each of the RAD001 dosing cohorts. Student T test was conducted to examine if the relative change of the immunophenotypes from baseline to the two blood sampling time points was significantly different from zero, respectively, within each dosing group after adjusting for placebo effect. Missing data imputation in treatment effect analysis was not conducted. Therefore if a patient has a missing phenotype data at baseline, this patient was not be included in the analysis for this phenotype. If a patient had a missing phenotype data at 6 or 12 weeks, then this patient did not contribute to the analysis of this phenotype for the affected timepoint.

608 tests in 76 phenotypes under 3 dosing groups were conducted to compare the treatment effect against the placebo effect. Stratified false discovery rate (FDR) control methodology was implemented to control the occurrence of false positives associated with multiple testing yet provide considerably better power. The cell type group was taken as the stratification factor and conducted FDR (q-value) calculation within each stratum respectively. All null-hypotheses were rejected at 0.05 significance level with corresponding q-value ≤0.1. The multiple testing adjustment strategy with rejecting at 0.05 significance level and corresponding q<0.1 ensured that less than 10% of the findings are false.

In a second analysis, the immunophenotype changes between pooled treatment and placebo groups, where all three RAD001 dosing groups were combined. To determine which immunophenotype changes differed between the treated and placebo groups, within-patient cell count ratios for each measured phenotype were calculated between baseline and Week 6 of study drug treatment and between baseline and the end of study (Week 12). The ratios were log transformed, and analyzed by analysis of covariance at each time point in order to detect a difference between the pooled treatment and placebo groups. 152 tests in 76 phenotypes were performed to compare the pooled treatment effect against the placebo effect. Stratified false discovery rate (FDR) control methodology was implemented to control the occurrence of false positives associated with multiple testing yet provide considerably better power (Benjamini, Y. et al. (1995) *J. Roy. Statist.* 57:289-300; and Sun, L. et al. (2006) *Genet. Epidemiol.* 30:519-530). The cell type group was taken as the stratification factor and FDR (q-value) calculation was conducted within each stratum respectively. All null-hypotheses at 0.05 significance level and q-value less than 20% were rejected. This can be interpreted as rejecting only those hypotheses with P values less than 0.05 and less than 20% probability that the each observed significant result is due to multiple testing.

Results

In general, RAD001 was well tolerated, particularly the 0.5 mg daily and 5 mg weekly dosing regimens. No deaths occurred during the study. Three subjects experienced four serious adverse events (SAEs) that were assessed as unrelated to RAD001. The 4 SAEs were retinal hemorrhage of the left eye with subsequent blindness in a subject with normal platelet counts who had completed a 6 week course of 5 mg weekly RAD001 6 weeks previously; severe back pain in a subject treated with placebo and severe gastroenteritis in a subject treated with placebo. A list of treatment-related adverse events (AEs) with an incidence >2% in any treatment group is provided in Table 3. The most common RAD001-related AE was mouth ulcer that, in the majority of cases, was of mild severity. Overall, subjects who received RAD001 had a similar incidence of severe AEs as those treated with placebo. Only one severe AE was assessed as related to RAD001 mouth ulcers in a subject treated with 20 mg weekly RAD001.

TABLE 3

Incidence of treatment-related AEs >2% in any treatment group by preferred term

| | RAD001 0.5 mg daily N = 53 n (%) | RAD001 5 mg weekly N = 53 n (%) | RAD001 20 mg weekly N = 53 n (%) | Placebo, pooled N = 59 n (%) | Total N = 218 n (%) |
|---|---|---|---|---|---|
| Total AE(s) | 35 | 46 | 109 | 21 | 211 |
| Patients with AE(s) | 22 (41.5%) | 20 (37.7%) | 27 (50.9%) | 12 (20.3%) | 81 (37.2%) |
| Mouth ulceration | 6 (11.3%) | 2 (3.8%) | 9 (17.0%) | 3 (5.1%) | 20 (9.2%) |
| Headache | 0 | 2 (3.8%) | 9 (17.0%) | 1 (1.7%) | 12 (5.5%) |
| Blood cholesterol increased | 2 (3.8%) | 2 (3.8%) | 2 (3.8%) | 0 | 6 (2.8%) |
| Diarrhea | 1 (1.9%) | 4 (7.5%) | 1 (1.9%) | 0 | 6 (2.8%) |
| Dyspepsia | 0 | 3 (5.7%) | 2 (3.8%) | 1 (1.7%) | 6 (2.8%) |
| Fatigue | 0 | 2 (3.8%) | 4 (7.5%) | 0 | 6 (2.8%) |
| Low density lipoprotein increased | 2 (3.8%) | 1 (1.9%) | 2 (3.8%) | 0 | 5 (2.3%) |
| Tongue ulceration | 3 (5.7%) | 1 (1.9%) | 0 | 1 (1.7%) | 5 (2.3%) |
| Insomnia | 1 (1.9%) | 2 (3.8%) | 1 (1.9%) | 0 | 4 (1.8%) |
| Dry mouth | 0 | 0 | 2 (3.8%) | 1 (1.7%) | 3 (1.4%) |
| Neutropenia | 0 | 0 | 3 (5.7%) | 0 | 3 (1.4%) |
| Oral pain | 0 | 2 (3.8%) | 1 (1.9%) | 0 | 3 (1.4%) |
| Pruritus | 0 | 2 (3.8%) | 1 (1.9%) | 0 | 3 (1.4%) |
| Conjunctivitis | 0 | 2 (3.8%) | 0 | 0 | 2 (0.9%) |
| Erythema | 0 | 2 (3.8%) | 0 | 0 | 2 (0.9%) |
| Limb discomfort | 0 | 2 (3.8%) | 0 | 0 | 2 (0.9%) |
| Mucosal inflammation | 0 | 0 | 2 (3.8%) | 0 | 2 (0.9%) |
| Paresthesia oral | 2 (3.8%) | 0 | 0 | 0 | 2 (0.9%) |
| Stomatitis | 0 | 0 | 2 (3.8%) | 0 | 2 (0.9%) |
| Thrombocytopenia | 0 | 0 | 2 (3.8%) | 0 | 2 (0.9%) |
| Urinary tract infection | 0 | 0 | 2 (3.8%) | 0 | 2 (0.9%) |

The ability of RAD001 to improve immune function in elderly volunteers was evaluated by measuring the serologic response to the 2012 seasonal influenza vaccine. The hemagglutination inhibition (HI) geometric mean titers (GMT) to each of the 3 influenza vaccine strains at baseline and 4 weeks after influenza vaccination are provided in Table 4. The primary analysis variable was the HI GMT ratio (4 weeks post vaccination/baseline). The study was powered to be able to demonstrate that in at least 2 out of 3 influenza vaccine strains there was 1) a ≥1.2-fold GMT increase relative to placebo; and 2) a posterior probability no lower than 80% that the placebo-corrected GMT ratio exceeded 1. This endpoint was chosen because a 1.2-fold increase in the influenza GMT ratio induced by the MF-59 vaccine adjuvant was associated with a decrease in influenza illness (Iob, A et al. (2005) *Epidemiol Infect* 133:687-693).

TABLE 4

HI GMTs for each influenza vaccine strain at baseline and at 4 weeks after influenza vaccination

| Influenza Vaccine Strain | | Time | RAD001 0.5 mg daily N = 50 | RAD001 5 mg weekly N = 49 | RAD001 20 mg weekly N = 49 | Placebo N = 55 |
|---|---|---|---|---|---|---|
| A/H1N1 | GMT (CV %) | Baseline | 102.8 (186.9) | 84.2 (236.4) | 90.1 (188.4) | 103.2 (219.7) |
| | | Week 4 | 190.2 (236.9) | 198.73(195.6) | 129.7 (175.9) | 169.4 (259.8) |
| | GMT ratio (CV %) | | 2.6 (302.5) | 2.5 (214.3) | 1.8 (201.5) | 2.0 (132.7) |
| A/H3N2 | GMT (CV %) | Baseline | 106.8 (168.2) | 126.04 (162.6) | 137.1 (211.5) | 131.7 (162.3) |
| | | Week 4 | 194.4 (129.1) | 223.0 (118.8) | 223.0 (163.6) | 184.3 (153.2) |
| | GMT ratio (CV %) | | 2.1 (152.6) | 2.0 (189.2) | 2.1 (277.3) | 1.6 (153.6) |
| B | GMT (CV %) | Baseline | 44.2 (96.6) | 64.8 (87.3) | 58.0 (156.0) | 57.0 (112.6) |
| | | Week 4 | 98.4 (94.8) | 117.3 (99.9) | 99.2 (124.1) | 114.6 (136.7) |
| | GMT ratio (CV %) | | 2.5 (111.2) | 2.2 (112.8) | 2.1 (126.5) | 2.2 (109.2) |

Baseline indicates 2 weeks prior to influenza vaccination
Week 4 indicates 4 weeks after influenza vaccination
N is number of subjects per cohort
GMT is geometric mean titer
GMT ratio is the GMT at week 4 post vaccination/GMT at baseline
CV % indicates coefficient of variation In the intent-to-treat (ITT) population, the low, immune enhancing, dose RAD001 (0.5 mg daily or 5 mg weekly) cohorts but not higher dose (20 mg weekly) cohort met the primary endpoint of the study (FIG. 1A). This demonstrates that there is a distinct immunomodulatory mechanism of RAD001 at the lower doses, and that at the higher dose the known immunosuppressive effects of mTOR inhibition may come into play. Furthermore, the results suggest a trend toward improved immune function in the elderly after low, immune enhancing, dose RAD001 treatment.

Figure 1B:
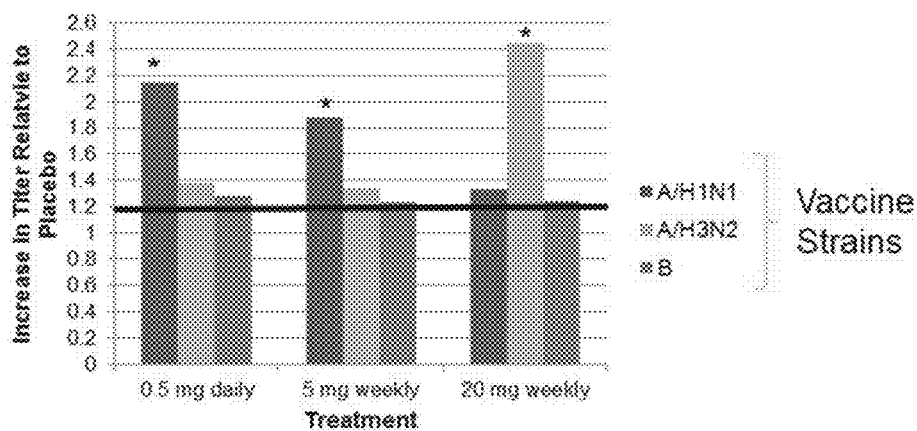

In a subgroup analysis, the subset of subjects with low baseline influenza titers (≤1:40) experienced a greater RAD001-associated increase in titers than did the ITT population (FIG. 1B). These data show that RAD001 is particularly effective at enhancing the influenza vaccine response of subjects who did not have protective (>1:40) titers at baseline, and therefore were at highest risk of influenza illness.

Figure 2:
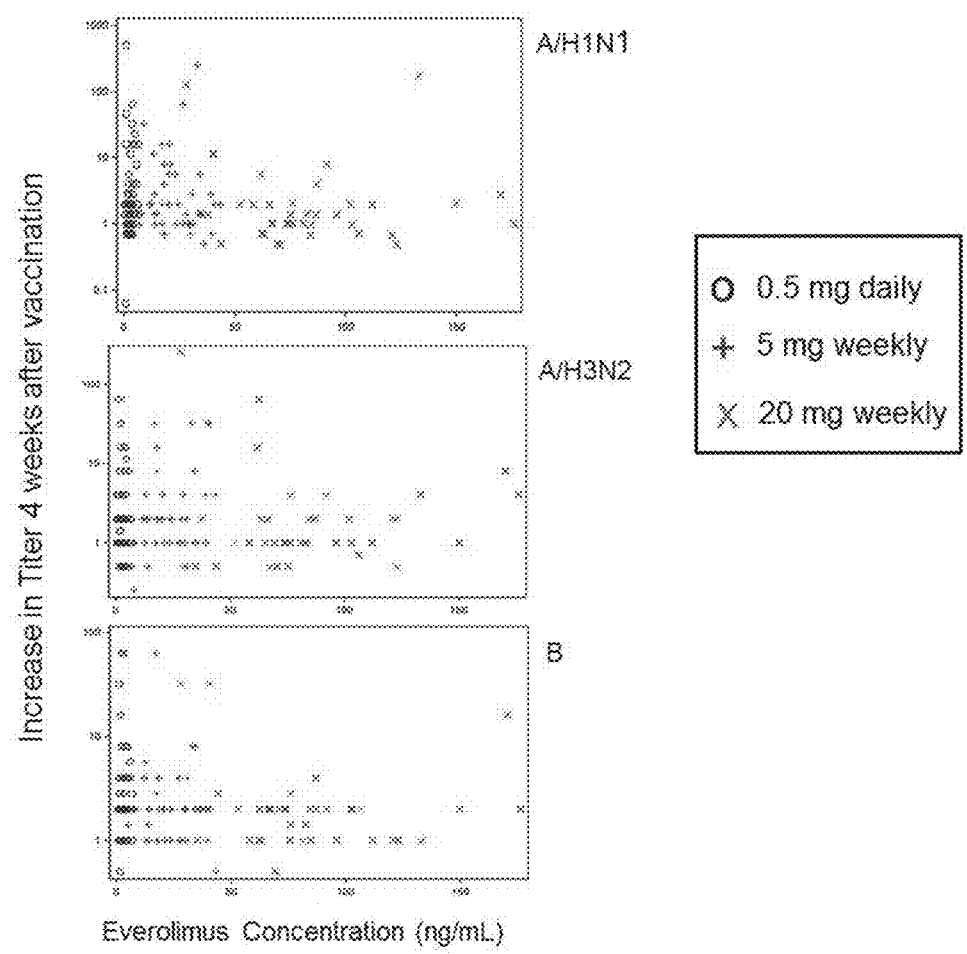
FIG. 2 shows a scatter plot of RAD001 concentration versus fold increase in geometric mean titer to each influenza vaccine strain 4 weeks after vaccination. RAD001 concentrations (1 hour post dose) were measured after subjects had been dosed for 4 weeks. All subjects who had pharmacokinetic measurements were included in the analysis set. The fold increase in geometric mean titers at 4 weeks post vaccination relative to baseline is shown on the y axis.

Scatter plots of RAD001 concentration versus increase in titer to each influenza vaccine strain show an inverse exposure/response relationship (FIG. 2). Modeling and simulation based on mTOR mediated phosphorylation of S6 kinase (S6K) predicts that the 20 mg weekly dosing regimen inhibits mTOR-mediated S6K activity almost completely, the 5 mg weekly dosing regimen inhibits S6K activity by over 50%, and the 0.5 mg daily dosing regiment inhibits S6K phosphorylation by approximately 38% during the dosing interval (Tanaka, C et al. (2008) *J. Clin. Oncol* 26:1596-1602). Thus, partial mTOR inhibition, e.g., mTOR-mediated S6K phosphorylation, with low, immune enhancing, dose RAD001 may be as, if not more effective, than near complete mTOR inhibition with high dose RAD001 at enhancing the immune response of the elderly.

Rates of seroconversion 4 weeks after influenza vaccination were also evaluated. Seroconversion was defined as the change from a negative pre-vaccination titer (i.e., HI titer <1:10) to post-vaccination HI titer≥1:40 or at least 4-fold increase from a non-negative (≥1:10) pre-vaccination HI titer. In the intention-to-treat population, seroconversion rates for the H3N2 and B strains were increased in the RAD001 as compared to the placebo cohorts although the increases did not meet statistical significance (Table 5). In the subpopulation of subjects with baseline influenza titers <=1:40, RAD001 treatment also increased the rates of seroconversion to the H3N2 and B strains, and these results reached statistical significance for the B strain in the 0.5 mg daily dosing cohort. These data further show that RAD001 enhanced the serologic response to influenza vaccination in the elderly.

TABLE 5

Percent of subjects with seroconversion to influenza 4 weeks after vaccination

| | Placebo N = 54 | 0.5 mg N = 48 | 5 mg N = 49 | 20 mg N = 48 |
|---|---|---|---|---|
| | Intention to Treat Population | | | |
| H1N1 | 24 | 27 | 27 | 17 |
| H3N2 | 17 | 27 | 24 | 25 |
| B | 17 | 27 | 22 | 19 |
| | Subjects with Baseline Titers <=40 | | | |
| H1N1 | 40 | 42 | 45 | 36 |
| H3N2 | 42 | 64 | 53 | 71 |
| B | 16 | 40* | 33 | 28 |

*Odds ratio for seroconversion between RAD001 and Placebo significantly different than 1 (two-sided p-value < 0.05 obtained by logistic regression with treatment as fixed effect)

Figure 3:
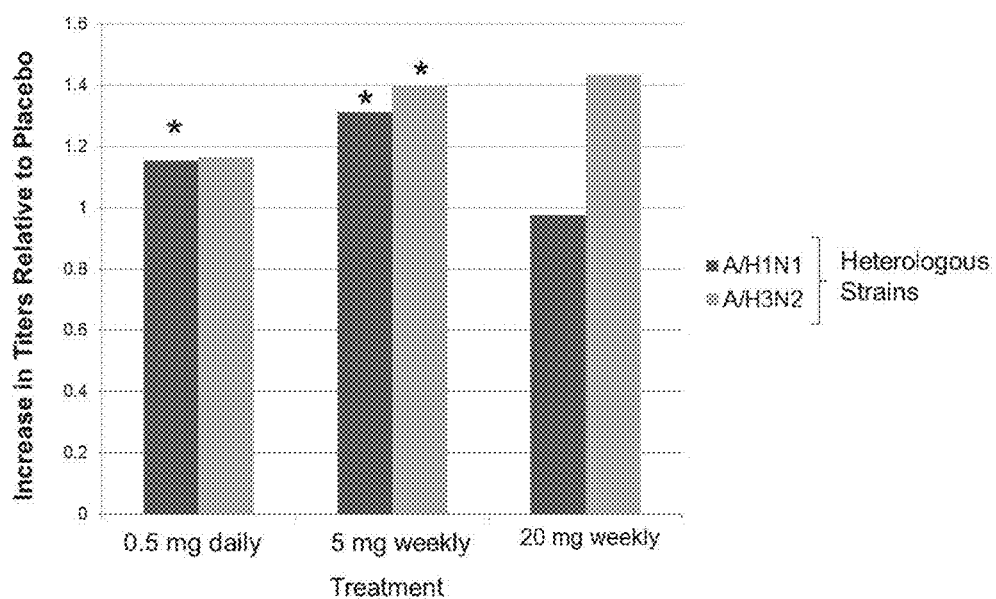
FIG. 3 is a graphic representation showing increase in titers to heterologous influenza strains as compared to placebo. The increase above baseline in influenza geometric mean titers to 2 heterologous influenza strains (A/H1N1 strain A/New Jersey/8/76 and A/H3N2 strain A/Victoria/361/11) not contained in the influenza vaccine relative to the increase in the placebo cohort 4 weeks after vaccination is shown for each of the RAD001 dosing cohorts in the intention to treat population. * indicates increase in titer relative to placebo exceeds 1 with a posterior probability of at least 80%.

Current seasonal influenza vaccines often provide inadequate protection against continuously emerging strains of influenza that present as variants of previously circulating viruses. However, mice vaccinated against influenza in the presence of the mTOR inhibitor rapamycin, as compared to placebo, developed a broader serologic response to influenza. The broader serologic response included antibodies to conserved epitopes expressed by multiple subtypes of influenza that provided protection against infection with heterologous strains of influenza not contained in the vaccine (Keating, R et al. (2013) *Nat Immunology* 14:2166-2178). To determine if RAD001 broadened the serologic response to influenza in the elderly volunteers, HI titers to 2 heterologous strains of influenza not contained in the influenza vaccine (A/H1N1 strain A/New Jersey/8/76 and A/H3N2 strain A/Victoria/361/11) were measured. The increase in the HI GMT ratios for the heterologous strains was higher in the RAD001 as compared to placebo cohorts (FIG. 3). In addition, seroconversion rates for the heterologous strains were higher in the RAD001 as compared to placebo cohorts. The increase in seroconversion rates in the 5 and 20 mg weekly RAD001 dosing cohorts was statistically significant for the H3N2 heterologous strain (Table 6). The H3N2 seroconversion rate for the pooled RAD001 cohorts was 39% versus 20% for the placebo cohort (p=0.007). The results presented herein suggest that mTOR inhibition broadens the serologic response of elderly volunteers to influenza vaccination, and increases antibody titers to heterologous strains of influenza not contained in the seasonal influenza vaccine.

Figure 4A:
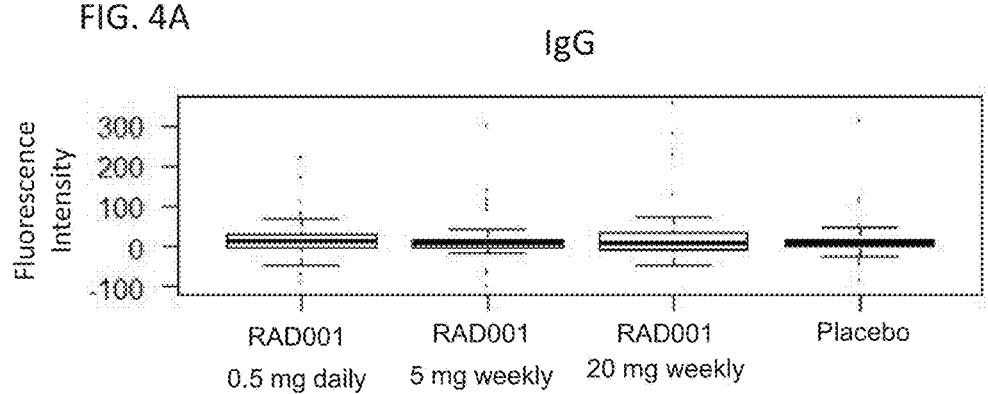
FIGS. 4A and 4B are graphic representations of IgG and IgM levels before and after influenza vaccination. Levels of anti-A/H1N1/California/07/2009 influenza IgG and IgM were measured in serum obtained from subjects before and 4 weeks post influenza vaccination. No significant difference in the change from baseline to 4 weeks post vaccination in anti-H1N1 influenza IgG and IgM levels were detected between the RAD001 and placebo cohorts (all p values >0.05 by Kruskal-Wallis rank sum test).
Figure 4B:
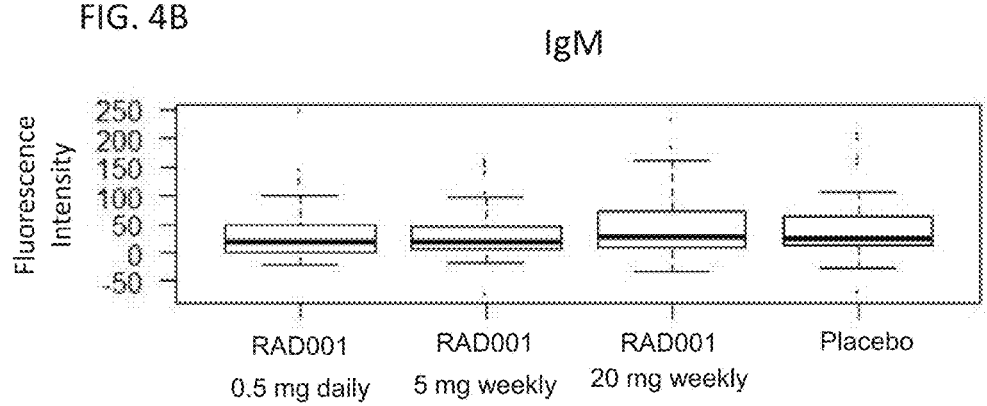

Broadened serologic response to heterologous strains of influenza in mice treated with rapamycin has been associated with an inhibition of class switching in B cells and an increase in anti-influenza IgM levels (Keating, R. et al. (2013) *Nat Immunol* 14:2166-2178). However, inhibition of class switching may not be involved in the broadened serologic response in humans treated with RAD001 because the post-vaccination anti-influenza IgM and IgG levels did not differ between RAD001 and placebo treated cohorts (FIGS. 4A and 4B, respectively).

TABLE 6

Percentage of subjects who seroconvert to heterologous strains of influenza 4 weeks after seasonal influenza vaccination

|  | Placebo, pooled | RAD001 0.5 mg daily | RAD001 5 mg weekly | RAD001 20 mg weekly |
|---|---|---|---|---|
| A/H1N1 strain: A/NewJersey/8/76 | 7% | 17% | 16% | 8% |
| A/H3N2 strain: A/Victoria/361/11 | 20% | 38% | 39%* | 40%* |

*Odds ratio for seroconversion between RAD001 and Placebo significantly different than 1 (two-sided p-value < 0.05 obtained by logistic regression with treatment as fixed effect)

Figure 5A:
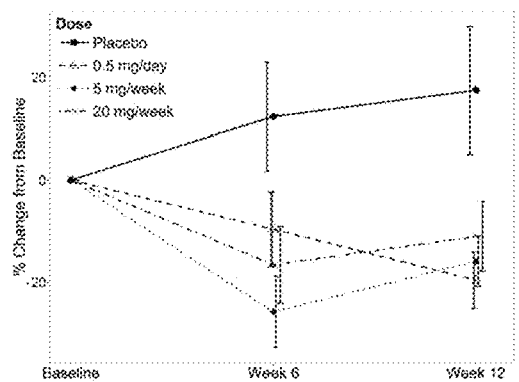
FIGS. 5A, 5B, and 5C are graphic representations of the decrease in percent of PD-1-positive CD4 and CD8 and increase in PD-1-negative CD4 T cells after RAD001 treatment. The percent of PD-1-positive CD4, CD8 and PD-1-negative CD4 T cells was determined by FACS analysis of PBMC samples at baseline, after 6 weeks of study drug treatment (Week 6) and 6 weeks after study drug discontinuation and 4 weeks after influenza vaccination (Week 12).
Figure 5B:
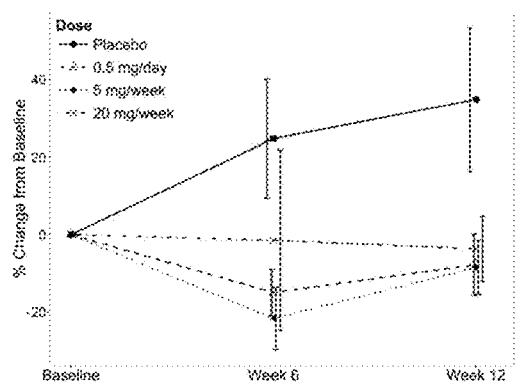
Figure 5C:
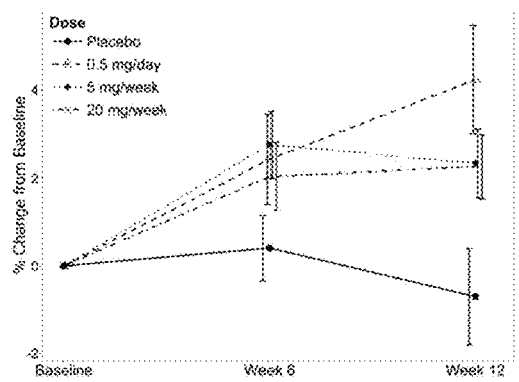

To address the mechanism by which RAD001 enhanced immune function in elderly volunteers, immunophenotyping was performed on PBMC samples obtained from subjects at baseline, after 6 weeks of study drug treatment and 4 weeks after influenza vaccination (6 weeks after study drug discontinuation). Although the percentage of most PBMC subsets did not differ between the RAD001 and placebo cohorts, the percentage of PD-1 positive CD4 and CD8 cells was lower in the RAD001 as compared to placebo cohorts (FIGS. 5A, 5B, and 5C). PD-1 positive CD4 and CD8 cells accumulate with age and have defective responses to antigen stimulation because PD-1 inhibits T cell receptor-induced T cell proliferation, cytokine production and cytolytic function (Lages, C S et al. (2010) *Aging Cell* 9:785-798). There was an increase in percentage of PD-1 positive T cells over time in the placebo cohort. At week 12 (4 weeks post-vaccination) this increase may have been due to influenza vaccination since influenza virus has been shown to increase PD-1 positive T cells (Erikson, J J et al. (2012) JCI 122:2967-2982). However the percentage of CD4 PD-1 positive T cells decreased from baseline at week 6 and 12 in all RAD001 cohorts (FIG. 5A). The percentage of CD8 PD-1 positive cells also decreased from baseline at both week 6 and 12 in the two lower dose RAD001 cohorts (FIG. 5B). The percentage of PD-1 negative CD4 T cells was evaluated and increased in the RAD001 cohorts as compared to the placebo cohorts (FIG. 5C).

Figure 6A:
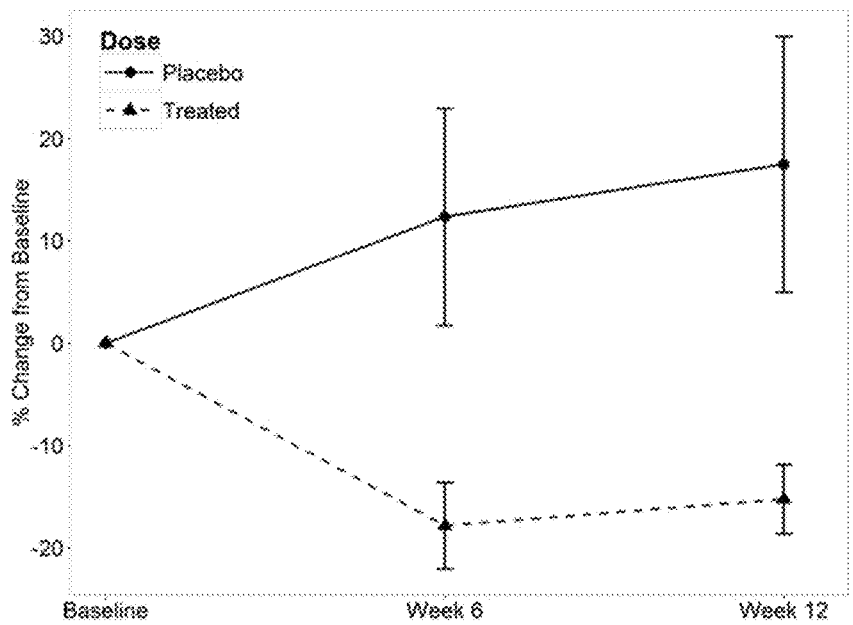
FIGS. 6A and 6B are graphic representations of the decrease in percent of PD-1-positive CD4 and CD8 and increase in PD-1-negative CD4 T cells after RAD001 treatment adjusted for differences in baseline PD-1 expression. The percent of PD-1-positive CD4, CD8 and PD-1-negative CD4 T cells was determined by FACS analysis of PBMC samples at baseline, after 6 weeks of study drug treatment (Week 6) and 6 weeks after study drug discontinuation and 4 weeks after influenza vaccination (Week 12).
Figure 6B:
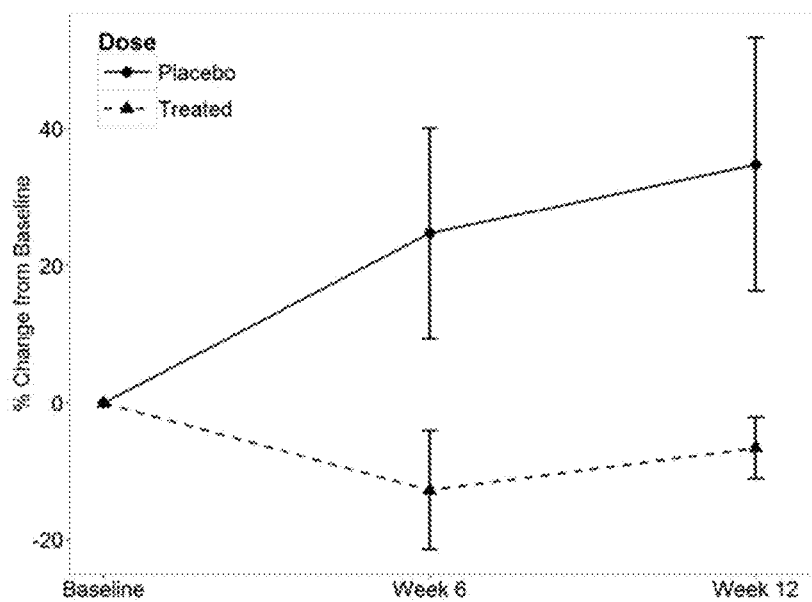

Under more stringent statistical analysis, where the results from the RAD001 cohorts were pooled and adjusted for differences in baseline PD-1 expression, there was a statistically significant decrease of 30.2% in PD-1 positive CD4 T cells at week 6 in the pooled RAD cohort (n=84) compared to placebo cohort (n=25) with p=0.03 (q=0.13) (FIG. 6A). The decrease in PD-1 positive CD4 T cells at week 12 in the pooled RAD as compared to the placebo cohort is 32.7% with p=0.05 (q=0.19). FIG. 6B shows a statistically significant decrease of 37.4% in PD-1 positive CD8 T cells at week 6 in the pooled RAD001 cohort (n=84) compared to placebo cohort (n=25) with p=0.008 (q=0.07). The decrease in PD-1 positive CD8 T cells at week 12 in the pooled RAD001 as compared to the placebo cohort is 41.4% with p=0.066 (q=0.21). Thus, the results from FIGS. 5 and 6 together suggest that the RAD001-associated decrease in the percentage of PD-1 positive CD4 and CD8 T cells may contribute to enhanced immune function.

Conclusion

In conclusion, the data presented herein show that the mTOR inhibitor RAD001 ameliorates the age-related decline in immunological function of the human elderly as assessed by response to influenza vaccination, and that this amelioration is obtained with an acceptable risk/benefit balance. In a study of elderly mice, 6 weeks treatment with the mTOR inhibitor rapamycin not only enhanced the response to influenza vaccination but also extended lifespan, suggesting that amelioration of immunosenescence may be a marker of a more broad effect on aging-related phenotypes.

Since RAD001 dosing was discontinued 2 weeks prior to vaccination, the immune enhancing effects of RAD001 may be mediated by changes in a relevant cell population that persists after discontinuation of drug treatment. The results presented herein show that RAD001 decreased the percentage of exhausted PD-1 positive CD4 and CD8 T cells as compared to placebo. PD-1 expression is induced by TCR signaling and remains high in the setting of persistent antigen stimulation including chronic viral infection. While not wishing to be bound by theory, is possible that RAD001 reduced chronic immune activation in elderly volunteers and thereby led to a decrease in PD-1 expression. RAD001 may also directly inhibit PD-1 expression as has been reported for the immunophilin cyclosporine A (Oestreich, K J et al. (2008) *J Immunol.* 181:4832-4839). A RAD001-induced reduction in the percentage of PD-1 positive T cells is likely to improve the quality of T cell responses. This is consistent with previous studies showing that mTOR inhibition improved the quality of memory CD8 T cell response to vaccination in mice and primates (Araki, K et al. (2009) *Nature* 460:108-112). In aged mice, mTOR inhibition has also been shown to increase the number of hematopoietic stem cells, leading to increased production of naïve lymphocytes (Chen, C et al. (2009) *Sci Signal* 2:ra75). Although significant differences in the percentages of naïve lymphocytes in the RAD001 versus placebo cohorts were not detected in this example, this possible mechanism may be further investigated.

The mechanism by which RAD001 broadened the serologic response to heterologous strains of influenza may be further investigated. Rapamycin has also been shown to inhibit class switching in B cells after influenza vaccination. As a result, a unique repertoire of anti-influenza antibodies was generated that promoted cross-strain protection against lethal infection with influenza virus subtypes not contained in the influenza vaccine (Keating, R et al. (2013) *Nat Immunol.* 14:2166-2178). The results described herein did not show that RAD001 altered B cell class switching in the elderly subjects who had discontinued RAD001 2 weeks prior to influenza vaccination. Although the underlying mechanism requires further elucidation, the increased serologic response to heterologous influenza strains described herein may confer enhanced protection to influenza illness in years when there is a poor match between the seasonal vaccine and circulating strains of influenza in the community.

The effect of RAD001 on influenza antibody titers was comparable to the effect of the MF59 vaccine adjuvant that is approved to enhance the response of the elderly to influenza vaccination (Podda, A (2001) *Vaccine* 19:2673-2680). Therefore, RAD001-driven enhancement of the antibody response to influenza vaccination may translate into clinical benefit as demonstrated with MF59-adjuvanted influenza vaccine in the elderly (Job, A et al. (2005) *Epidemiol Infect.* 133:687-693). However, RAD001 is also used to suppress the immune response of organ transplant patients. These seemingly paradoxical findings raise the possibility that the immunomodulatory effects of mTOR inhibitors may be dose and/or antigen-dependent (Ferrer, I R et al. (2010) *J Immunol.* 185:2004-2008). A trend toward an inverse RAD001 exposure/vaccination response relationship was seen herein. It is possible that complete mTOR inhibition suppresses immune function through the normal cyclophilin-rapamycin mechanism, whereas partial mTOR inhibition, at least in the elderly, enhances immune function due to a distinct aging-related phenotype inhibition. Of interest, mTOR activity is increased in a variety of tissues including hematopoietic stem cells in aging animal models (Chen C. et al. (2009) *Sci Signal* 2:ra75 and Barns, M. et al. (2014) *Int J Biochem Cell Biol.* 53:174-185). Thus, turning down mTOR activity to levels seen in young tissue, as opposed to more complete suppression of mTOR activity, may be of clinical benefit in aging indications.

The safety profile of mTOR inhibitors such as RAD001 in the treatment of aging-related indications has been of concern. The toxicity of RAD001 at doses used in oncology or organ transplant indications includes rates of stomatitis, diarrhea, nausea, cytopenias, hyperlipidemia, and hyperglycemia that would be unacceptable for many aging-related indications. However, these AEs are related to the trough levels of RAD001 in blood. Therefore the RAD001 dosing regimens used in this study were chosen to minimize trough levels. The average RAD001 trough levels of the 0.5 mg daily, 5 mg weekly and 20 mg weekly dosing cohorts were 0.9 ng/ml, below 0.3 ng/ml (the lower limit of quantification), and 0.7 ng/ml, respectively. These trough levels are significantly lower than the trough levels associated with dosing regimens used in organ transplant and cancer patients. In addition, the limited 6 week course of treatment decreased the risk of adverse events. These findings suggest that the dosing regimens used in this study may have an acceptable risk/benefit for some conditions of the elderly. Nonetheless, significant numbers of subjects in the experiments described herein developed mouth ulcers even when dosed as low as 0.5 mg daily. Therefore the safety profile of low, immune enhancing, dose RAD001 warrants further study. Development of mTOR inhibitors with cleaner safety profiles than currently available rapalogs may provide better therapeutic options in the future for aging-associated conditions.

Example 2: Enhancement of Immune Response to Vaccine in Elderly Subjects

Immune function declines in the elderly, leading to an increase incidence of infection and a decreased response to vaccination. As a first step in determining if mTOR inhibition has anti-aging effects in humans, a randomized placebo-controlled trial was conducted to determine if the mTOR inhibitor RAD001 reverses the aging-related decline in immune function as assessed by response to vaccination in elderly volunteers. In all cases, appropriate patent consents were obtained and the study was approved by national health authorities.

The following 3 dosing regimens of RAD001 were used in the study:
20 mg weekly (trough level: 0.7 ng/ml)
5 mg weekly (trough level was below detection limits)
0.5 mg daily (trough level: 0.9 ng/ml)

These dosing regimens were chosen because they have lower trough levels than the doses of RAD001 approved for transplant and oncology indications. Trough level is the lowest level of a drug in the body. The trough level of RAD001 associated with the 10 mg daily oncology dosing regimen is approximately 20 ng/ml. The trough level associated with the 0.75-1.5 mg bid transplant dosing regimen is approximately 3 ng/ml. In contrast, the trough level associated with the dosing regimens used in our immunization study were 3-20 fold lower.

Since RAD001-related AEs are associated with trough levels, the 3 dosing regimens were predicted to have adequate safety for normal volunteers. In addition, the 3 doses were predicted to give a range of mTOR inhibition. P70 S6 Kinase (P70 S6K) is a downstream target that is phosphorylated by mTOR. Levels of P70 S6K phosphorylation serve as a measure of mTOR activity. Based on modeling and simulation of P70 S6K phosphorylation data obtained in preclinical and clinical studies of RAD001, 20 mg weekly was predicted to almost fully inhibit mTOR activity for a full week, whereas 5 mg weekly and 0.5 mg daily were predicted to partially inhibit mTOR activity.

Elderly volunteers >=65 years of age were randomized to one of the 3 RAD001 treatment groups (50 subjects per arm) or placebo (20 subjects per arm). Subjects were treated with study drug for 6 weeks, given a 2 week break, and then received influenza (Aggrippal, Novartis) and pneumoccal (Pneumovax 23, Merck), vaccinations. Response to influenza vaccination was assessed by measuring the geometric mean titers (GMTs) by hemagglutination inhibition assay to the 3 influenza strains (H1N1, H3N2 and B influenza subtypes) in the influenza vaccine 4 weeks after vaccination. The primary endpoints of the study were (1) safety and tolerability and (2) a 1.2 fold increase in influenza titers as compared to placebo in 2/3 of the influenza vaccine strains 4 weeks after vaccination. This endpoint was chosen because a 1.2 fold increase in influenza titers is associated with a decrease in influenza illness post vaccination, and therefore is clinically relevant. The 5 mg weekly and 0.5 mg daily doses were well tolerated and unlike the 20 mg weekly dose, met the GMT primary endpoint (FIG. 1A). Not only did RAD001 improve the response to influenza vaccination, it also improved the response to pneumococcal vaccination as compared to placebo in elderly volunteers. The pneumococcal vaccine contains antigens from 23 pneumococcal serotypes. Antibody titers to 7 of the serotypes were measured in our subjects. Antibody titers to 6/7 serotypes were increased in all 3 RAD cohorts compared to placebo.

The combined influenza and pneumococcal titer data suggest that partial (less than 80-100%) mTOR inhibition is more effective at reversing the aging-related decline in immune function than more complete mTOR inhibition.

Example 3: Low Dose mTOR Inhibition Increases Energy and Exercise

Figure 7:
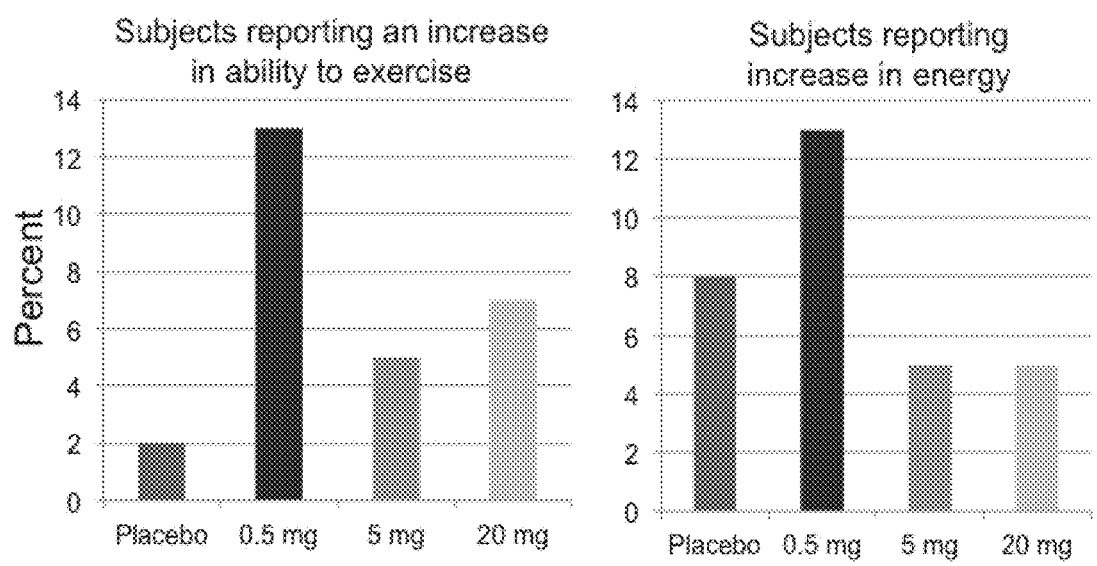
FIG. 7 depicts increases in exercise and energy in elderly subjects in response to RAD001.

In preclinical models, mTOR inhibition with the rapalog rapamycin increases spontaneous physical activity in old mice (Wilkinson et al. Rapamycin slows aging in mice. (2012) Aging Cell; 11:675-82). Of interest, subjects in the 0.5 mg daily dosing cohort described in Example 2 also reported increased energy and exercise ability as compared to placebo in questionnaires administered one year after dosing (FIG. 7). These data suggest that partial mTOR inhibition with rapalogs may have beneficial effects on aging-related morbidity beyond just immune function.

Example 4: P70 S6 Kinase Inhibition with RAD001

Figure 8A:
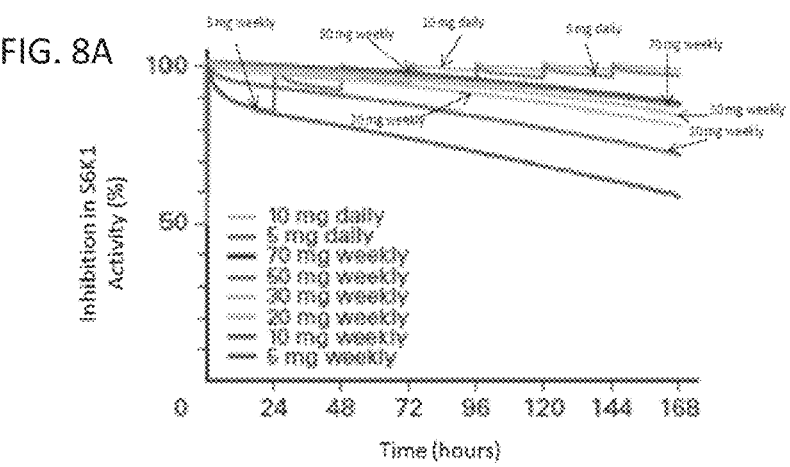
FIGS. 8A and 8B depict the predicted effect of RAD001 on P70 S6K activity in cells.
Figure 8B:
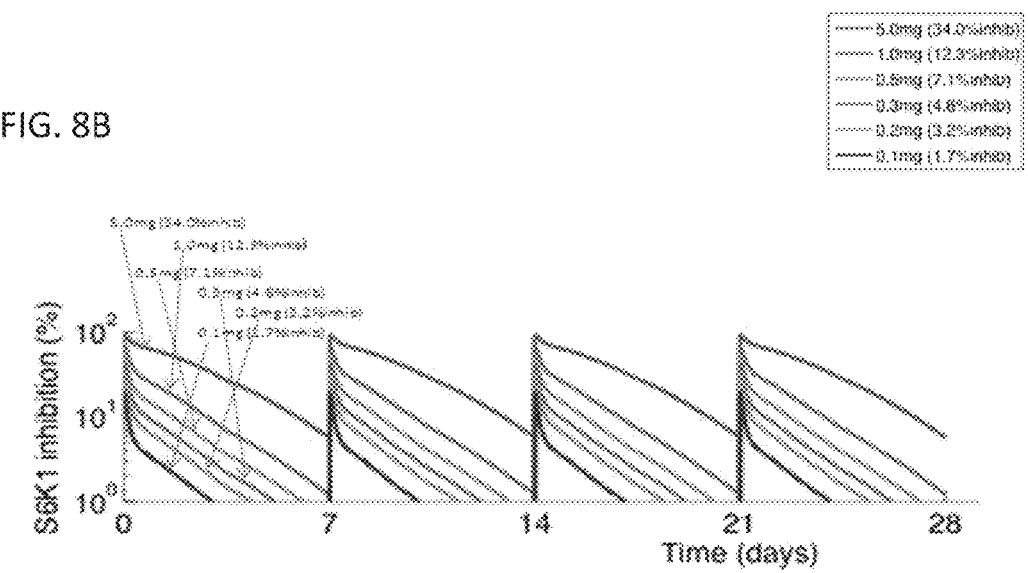

Modeling and simulation were performed to predict daily and weekly dose ranges of RAD001 that are predicted to partially inhibit mTOR activity. As noted above, P70 S6K is phosphorylated by mTOR and is the downstream target of mTOR that is most closely linked to aging because knockout of P70 S6K increases lifespan. Therefore modeling was done of doses of RAD001 that partially inhibit P70 S6K activity. Weekly dosing in the range of >=0.1 mg and <20 mg are predicted to achieve partial inhibition of P70 S6K activity (FIGS. 8A and 8B).

For daily dosing, concentrations of RAD001 from 30 pM to 4 nM partially inhibited P70 S6K activity in cell lines (Table 7). These serum concentrations are predicted to be achieved with doses of RAD001>=0.005 mg to <1.5 mg daily.

TABLE 7

Percent inhibition of P70 S6K activity in HeLa cells in vitro

| RAD001 concentration | 0 | 6 pM | 32 pM | 160 pM | 800 pM | 4 nM | 20 nM |
|---|---|---|---|---|---|---|---|
| % P70 S6K inhibition | 0 | 0 | 18 | 16 | 62 | 90 | 95 |

Conclusion

Methods of treating aging-related morbidity, or generally enhancing an immune response, with doses of mTOR inhibitors that only partially inhibit P70 S6K. The efficacy of partial mTOR inhibition with low doses of RAD001 in aging indications is an unexpected finding. RAD001 dose ranges between >=0.1 mg to <20 mg weekly and >=0.005 mg to <1.5 mg daily will achieve partial mTOR inhibition and therefore are expected to have efficacy in aging-related morbidity or in the enhancement of the immune response.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

Other embodiments are within the following claims.

What is claimed is:

1. A method of promoting an immune response in an immunosenescent human subject, comprising administering to the immunosenescent human subject a low, immune enhancing, dose of about 0.1 mg of RAD001, orally and once daily, thereby enhancing or promoting an immune response in the immunosenescent human subject.

2. The method of claim 1, wherein the immunosenescent human subject is immunocompromised.

3. The method of claim 1, wherein the immunosenescent human subject has an infectious disease.

4. The method of claim 1, wherein the immunosenescent human subject has an impaired immune response.

5. The method of claim 1, comprising treating the immunosenescent human subject for an age related condition.

6. The method of claim 5, wherein the age related condition is selected from the group consisting of sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability, cognitive decline, memory impairment, tendon stiffness, heart dysfunction, cancer, obesity, and diabetes.

7. A method of evaluating an immunosenescent human subject for treatment with a low, immune enhancing, dose of RAD001 to promote or enhance an immune response to an influenza vaccine or antigen, comprising:
   establishing a reference baseline or pre-immunization level of anti-influenza antibody,
   measuring a baseline or pre-immunization level of anti-influenza antibody in the immunosenescent human subject, and
   comparing the baseline or pre-immunization level of anti-influenza antibody in the immunosenescent human subject to the reference value,
   wherein a baseline or pre-immunization level of anti-influenza antibody in the immunosenescent human subject less than the reference value is predictive of a greater RAD001 associated increase in antibody titer for the influenza antigen,
   and wherein the immunosenescent human subject, once evaluated, is then treated with a low, immune enhancing dose of RAD001,
   wherein treatment comprises administering a dose of about 0.1 mg of RAD001, orally and once daily.

8. A composition comprising
   (a) a vaccine antigen; and
   (b) about 0.1 mg of RAD001.

9. The method of claim 6, wherein the aging-related mobility disability is frailty.

10. The method of claim 6, wherein the dementia is age-related dementia.

11. The method of claim 6, wherein the heart dysfunction is cardiac hypertrophy or systolic or diastolic dysfunction.

* * * * *